United States Patent
Combrink et al.

(10) Patent No.: US 7,250,413 B2
(45) Date of Patent: Jul. 31, 2007

(54) C-25 CARBAMATE RIFAMYCIN DERIVATIVES WITH ACTIVITY AGAINST DRUG-RESISTANT MICROBES

(75) Inventors: Keith Combrink, Fort Worth, TX (US); Susan Harran, Dallas, TX (US); Daniel Denton, Irving, TX (US); Zhenkun Ma, Dallas, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 175 days.

(21) Appl. No.: 11/114,384

(22) Filed: Apr. 26, 2005

(65) Prior Publication Data

US 2005/0256096 A1 Nov. 17, 2005

Related U.S. Application Data

(60) Provisional application No. 60/565,497, filed on Apr. 26, 2004.

(51) Int. Cl.
*C07D 498/08* (2006.01)
*C07D 519/00* (2006.01)
*A61K 31/4709* (2006.01)
*A61K 31/496* (2006.01)
*A61P 31/04* (2006.01)

(52) U.S. Cl. ............... 514/232.8; 514/235.2; 540/456

(58) Field of Classification Search ........ 540/456; 514/232.8, 235.2
See application file for complete search history.

(56) References Cited

U.S. PATENT DOCUMENTS

| 4,188,321 A | 2/1980 | Maggi et al. |
| 5,786,350 A | 7/1998 | Occelli et al. |

FOREIGN PATENT DOCUMENTS

| WO | WO-01/051456 A2 | 7/2001 |
| WO | WO-03/045319 A2 | 6/2003 |

OTHER PUBLICATIONS

Brufani, M., et al.; "Rifamycins: An Insight into Biological Activity Based on Structural Investigations"; J. Mol. Biol. 1974, vol. 87, pp. 409-435.
Farr, B. M.; "Rifamycins"; Principles and Practice of Infectious Diseases; Mandell, G. L., Bennett, J. E., Dolin, R., Eds.; Churchhill Livingstone: Philadelphia, pp. 348-361, 2000.
Ince, D. et al.; "Mechanisms and Frequency of Resistance to Premafloxacin in *Staphylococcus aureus*: Novel Mutations Suggest Novel Drug-Target Interactions"; Antimicrobial Agents and Chemotherapy, Dec. 2000, vol. 44, No. 12, pp. 3344-3350.
Kim, Y. H., et al; "New Synthesis of a-Oximino-a-Haloketones: Reactions of a-haloketones with Alkyl Thionitrites", Tet. Lett., vol. 22(25), pp. 2371-2372, 1981.
Kocevar, M., et al.; "Simple Procedure for the Synthesis of Pyridinecarbhydroximoyl Chlorides and Bromides", Syn. Comm., vol. 18(12), pp. 1427-1432, 1988.
Kump, W., et al.; "Zur Kenntnis von Rifamycin-S.-Reaktionen des Ansaringes"; Helv. Chim. Acta., 1973, vol. 56(7), pp. 2323-2347.
Wehrli, W., et al. "CGP 4832, A New Semisynthetic Rifamycin Derivative Highly Active Against Some Gram-Negative Bacteria"; The Journal of Antibiotics, vol. 40(12), pp. 1733-1739, 1987.
Zamponi, G. W., et al.; "Unique Structure-Activity Relationship for 4-Isoxazolyl-1, 4-dihydropyridines" J. Med. Chem., vol. 46(1), pp. 87-96, 2003.

*Primary Examiner*—Bruck Kifle
(74) *Attorney, Agent, or Firm*—Jackson Walker L.L.P.

(57) ABSTRACT

Compounds of the current invention relate to rifamycin derivatives having antimicrobial activities, including activities against drug-resistant microorganisms. More specifically, compounds of the current invention relate to C-25 carbamate derivatives of rifamycin having another functional group or pharmacophore covalently attached to this position through a carbamate linkage. The resulting compounds exert their antimicrobial activity through a dual-function mechanism and therefore exhibit reduced frequency of resistance.

18 Claims, 11 Drawing Sheets

SCHEME 1

SCHEME 2

SCHEME 3

SCHEME 4

SCHEMES 5a AND 5b

SCHEME 6

SCHEME 7

SCHEMES 8a AND 8b

Scheme 8a

Scheme 8b

C-25 CARBAMATE RIFAMYCIN DERIVATIVES WITH ACTIVITY AGAINST DRUG-RESISTANT MICROBES

RELATED APPLICATIONS

This application claims priority to U.S. Provisional Patent Application, Ser. No. 60/565,497, entitled "C-25 Carbamate Rifamycin Derivatives with Activity against DRUG-Resistant Microbes" filed on Apr. 26, 2004, having Combrink et al., listed as the inventors, the entire content of which is hereby incorporated by reference.

BACKGROUND OF THE INVENTION

This invention relates to novel rifamycin derivatives having antimicrobial activity, compositions containing the compounds, and methods for treatment and prevention of microbial infections. The compounds of the current invention are potent antibacterial agents active against certain drug-resistant, and particularly rifamycin-resistant pathogens.

Rifamycins are natural products with potent antimicrobial activity. Examples of the naturally-occurring rifamycins are rifamycin B, rifamycin O, rifamycin R, rifamycin U, rifamycin S, rifamycin SV and rifamycin Y (Brufani et al., 1974). The therapeutic applications of the naturally-occurring rifamycins are limited due to their poor oral bioavailability, weak activity against Gram-negative pathogens and low distribution into the infected tissues. Significant efforts have been made toward to identifying semi-synthetic rifamycin derivatives to address the deficiencies. As a result, many semi-synthetic rifamycin derivatives with improved spectrums and pharmacological profiles have been identified. Among the semi-synthetic compounds, rifampin, rifabutin and rifapetine have been developed into therapeutic agents and are widely used for the treatment of tuberculosis and other microbial infections (Farr, Rifamycins).

One of the major problems associated with the rifamycin class of antimicrobial agents is the rapid development of microbial resistance. Compounds of the current invention are designed to address the rifamycin resistance problem by covalently attaching another functional group to the C-25 position of rifamycin scaffold that provides an additional binding interaction with RNA polymerase or interacts to an additional enzyme target.

Reference is made to U.S. Pat. No. 4,188,321 that describes a series of C-25 desacetyl derivatives and Wehrli, Zimmerman et al., 1987, that discloses a series of C-25 rifamycin derivatives modified through an ester linkage. The compounds of the current invention are rifamycin derivatives having stable C-25 carbamate functionality, which are novel.

Reference is made to Kump and Bickel, 1973, which describes preparation of a propionate and pivalate esters at C-25. Reference is made to U.S. Pat. No. 5,786,350 that discloses a series of C-36 derivatives of rifamycins, including derivatives formed by linking the C-3 carboxy group of a fluoroquinolone to the C-36 position of rifamycins through a chemically and metabolically liable ester group. Compounds of the current invention link an antibiotic to the C-25 position of rifamycins through a chemically and metabolically stable carbamate linker.

Reference is also made to International Patent Application Publication No. WO 03/045319 A2 which discloses rifamycin derivatives formed by linking rifamycin and a therapeutic drug and the use of these derivatives as vehicles for delivering the therapeutic drug. However, the aforementioned reference failed to demonstrate by specific examples that any drug is introduced to the C-25 position of a rifamycin molecule. Derivatives in which the C-25 acetate is replaced by a carbamate linkage are not described and no examples for the preparation of such examples are known.

SUMMARY

One aspect of the current invention is a compound having a Formula I:

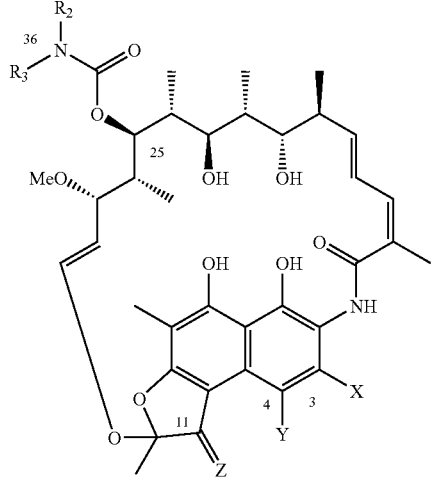

Formula I or its corresponding quinone form Formula II:

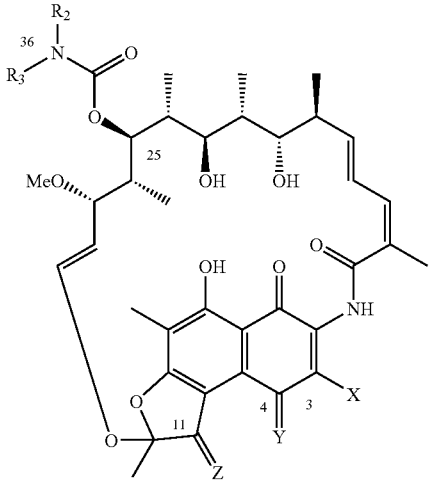

Formula II or its salts, hydrates, prodrugs or mixtures thereof. In these Formulas, $-NR_2R_3$ is a new attachment point for the rifamycin class of antibiotics in which $R_2$ and $R_3$ can be a wide variety of substituents including those containing a second antibacterial pharmacophore.

A preferred X in the above structures comprises: $-H$, $-NR_{11}R_{12}$, $-CH_2-NR_{11}R_{12}$, $-CH=NNR_{11}R_{12}$, $-SR_{13}$ or $-L_3-Q_3$, wherein $L_3$ is a linker attached to $Q_3$, and $Q_3$ represents an antibacterial pharmacophore. $R_{11}$ and $R_{12}$ independently represent hydrogen, $(C_1-C_6)$alkyl, or substituted $(C_1-C_6)$alkyl. Alternatively, $R_{11}$ and $R_{12}$, together with the nitrogen atom to which they are attached, can form a 4- to 8-membered heterocyclic ring, optionally containing one additional heteroatom selected from oxygen, nitrogen and sulfur, wherein one of the carbon or nitrogen atoms is optionally substituted by a $(C_1-C_6)$alkyl or substituted $(C_1-C_6)$alkyl. $R_{13}$ represents $(C_1-C_6)$alkyl or substituted $(C_1-C_6)$alkyl.

A preferred Y in the above Formula I comprises: —$OR_1$, wherein $R_1$ represents hydrogen, $(C_1-C_6)$alkyl, substituted $(C_1-C_6)$alkyl, —$CH_2COOH$, or —$CH_2CONR_{11}R_{12}$. $R_{11}$ and $R_{12}$ are defined as above.

A preferred Y in the above Formula II represents =O.

A preferred Z encompasses =O, =NH, or =$NOR_{14}$. $R_{14}$ is —H, alkyl, aryl, heteroaryl or -$L_{11}$-$Q_{11}$, wherein $L_{11}$ is a linker attached to $Q_{11}$ and $Q_{11}$ represents an antibacterial pharmacophore.

A preferred $R_2$ and $R_3$ in the above structures are independently selected from hydrogen, $(C_1-C_6)$alkyl, $(C_1-C_6)$alkenyl, $(C_1-C_6)$alkynyl, aryl, or heteroaryl. These groups optionally can be further substituted. $R_2$ and $R_3$ can also independently represent -$L_{25}$-$Q_{25}$. Alternatively, $R_2$ and $R_3$, together with the nitrogen to which they are attached, can form a 4- to 8-membered heterocyclic ring containing one or two additional heteroatoms, wherein the carbon or nitrogen atoms of the ring are optionally substituted with hydrogen, $(C_1-C_6)$alkyl, $(C_1-C_6)$alkylamino, di$(C_1-C_6)$alkylamino, hydroxyl, $(C_1-C_6)$alkoxy, or -$L_{25}$-$Q_{25}$. $L_{25}$ is a linker attached to $Q_{25}$ and $Q_{25}$ represents another antibacterial pharmacophore.

In the above Formulas I and II, X and Y together may form heterocyclic ring structures having Formula III, IV, V or VI:

Formula III–VI

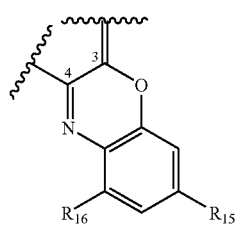

III

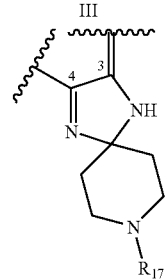

IV

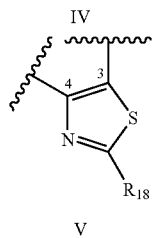

V

-continued

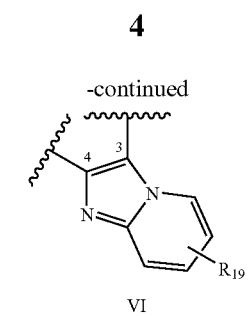

VI

For clarity, structures III-VI are illustrated to show a portion of the original structure of Formulas I and II. In particular, structures III-VI show the C-3 and C-4 positions of the rifamycin of Formulas I and II. In these structures, $R_{15}$ is a group of the formula —$NR_{20}R_{21}$. $R_{16}$ is hydrogen, $(C_1-C_6)$alkyl, OH or $NH_2$. $R_{17}$, $R_{20}$, and $R_{21}$ independently are $(C_1-C_6)$alkyl, $(C_1-C_6)$alkenyl, $(C_1-C_6)$alkynyl, or $(C_3-C_8)$cycloalkyl. Alternatively, $R_{20}$ and $R_{21}$, together with the nitrogen to which they are attached, may form a 4-8 membered heterocyclic ring containing one or two additional heteroatoms, wherein the nitrogen atoms are optionally substituted with hydrogen, $(C_1-C_6)$alkyl, $(C_1-C_6)$alkenyl, $(C_1-C_6)$alkynyl, or $(C_3-C_8)$cycloalkyl. $R_{18}$ is $(C_1-C_6)$alkyl, $(C_1-C_6)$alkenyl, $(C_1-C_6)$alkynyl, $(C_3-C_8)$cycloalkyl, $(C_1-C_5)$alkylheterocycle, or —$NR_{20}R_{21}$. $R_{19}$ is $(C_1-C_6)$alkyl, $(C_1-C_6)$ alkenyl, $(C_1-C_6)$alkynyl, $(C_3-C_8)$cycloalkylene, or —$NR_{20}R_{21}$.

$L_3$, $L_{11}$ and $L_{25}$ may be the same or different and represent any combination of 1 to 5 of the following structures: $(C_1-C_6)$alkylene, $(C_1-C_6)$alkenylene, $(C_1-C_6)$alkynylene, $(C_3-C_8)$cycloalkylene, heterocycle structure containing 1 to 3 heteroatoms, arylene and heteroarylene, wherein the group is optionally interrupted by 1 to 3 heteroatoms selected from N, O and S, and wherein the carbon or nitrogen atoms of the linker group are optionally substituted by 1 to 3 substituents selected from $(C_1-C_6)$alkyl, heterocycloalkyl, amino, $(C_1-C_6)$alkylamino, di$(C_1-C_6)$alkylamino, hydroxyl, or $(C_1-C_6)$alkoxy. All of these groups optionally can be further substituted.

Preferred sets of linkers $L_3$, $L_{11}$, and $L_{25}$ may independently be absent or a linker formed by any combination of 0-3 structures shown in FIG. 1.

$Q_3$, $Q_{11}$ and $Q_{25}$ are a pharmacophore, therapeutic drug, or antibacterial agent. $Q_3$, $Q_{11}$ and $Q_{25}$ independently can be a quinolone, an oxazolidinone, a macrolide, an aminoglycoside, a tetracycline or any structure associated with an antibacterial agent. Preferably, $Q_3$, $Q_{11}$ and $Q_{25}$ independently can be a quinolone, a macrolide, or an oxazolidinone core.

A preferred $Q_3$, $Q_{11}$ or $Q_{25}$ pharmacophore comprises Formula VI, Formula VII, or Formula VIII:

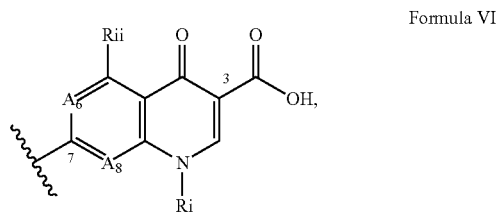

Formula VI

Formula VII

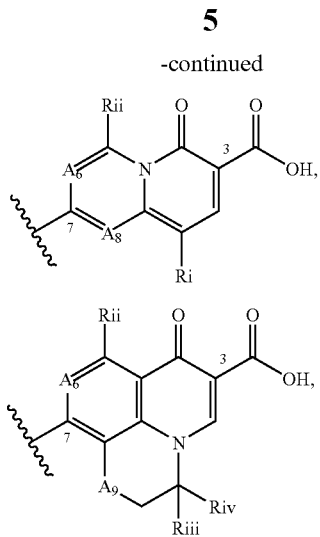

Formula VIII wherein Ri comprises: $(C_1-C_6)$alkyl, $(C_3-C_6)$cycloalkyl, substituted $(C_3-C_6)$cycloalkyl, aryl, substituted aryl, heteroaryl, or substituted heteroaryl; Rii comprises hydrogen, halogen, amino, nitro or methyl; and Riii and Riv independently comprise hydrogen or $(C_1-C_6)$alkyl. Alternatively, Riii and Riv, together with the carbon atom to which they are attached, form a 3- to 6-membered carbocyclic ring. $A_6$ represents C—H, C—F, or N. $A_8$ represents C—H, C—F, C—Cl, C-Me, C—OMe, C—OCH$_2$F, C—OCHF$_2$, or N. $A_9$ represents CH$_2$, O or S. The preferred quinolone pharmacophores shown in Formulas VI, VII, and VIII are covalently coupled or bonded to the linker $L_3$, $L_{11}$ or $L_{25}$, which in turn is covalently coupled or bonded to rifamycin through the $C_7$ carbon of the quinolone core structure. Preferred sets of linkers are any combination of from one to three structures shown in FIG. 1, where the left side of the linker is attached to rifamycin molecule through a C—N, C—O or C—C bond and the right side of the linker is attached to the quinolone molecule through a C—N, C—O or C—C bond. A more preferred $Q_3$, $Q_{11}$ and $Q_{25}$ pharmacophore may comprise any of the structures related to quinolones shown in FIG. 2.

Another preferred $Q_3$, $Q_{11}$ and $Q_{25}$ pharmacophore comprises any of the structural formulas related to the macrolide antibiotics, as shown below:

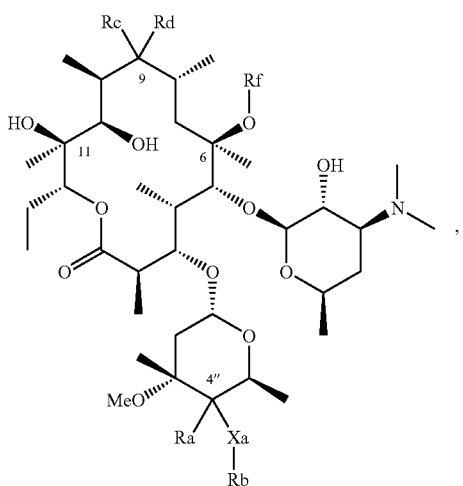

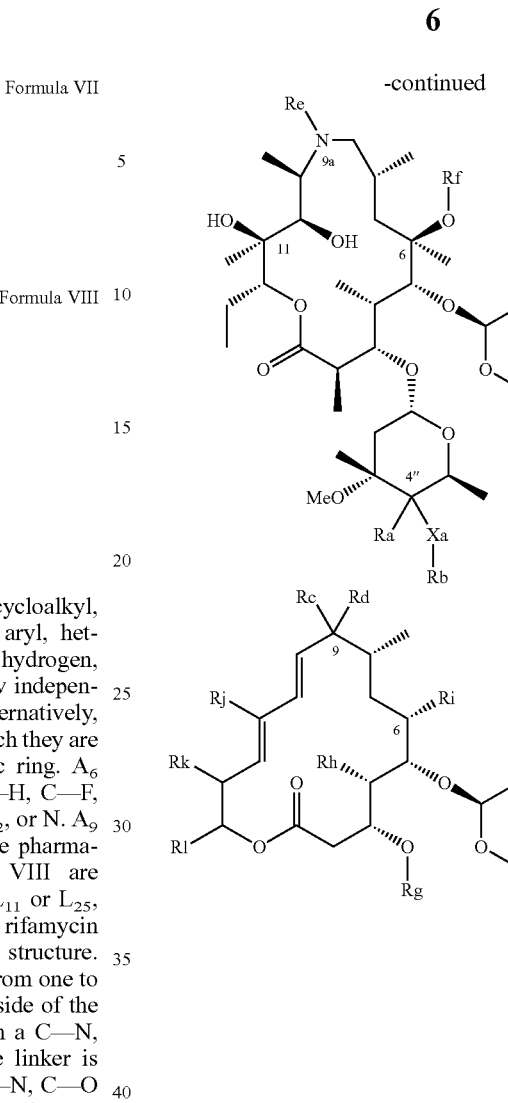

wherein, Ra is hydrogen or hydroxyl. Xa is —O—, —NH—, or —CH$_2$NH—. Rb is -Xb-Rx, wherein Xb is absent or is any combination of from one to three structures shown in FIG. 1, where the left side of the linker is attached to the rifamycin molecule through a C—N, C—O or C—C bond, and the right side of the linker is attached to the macrolide core trough a C—N, C—O or C—C bond. Rx comprises $(C_1-C_6)$alkyl, substituted $(C_1-C_6)$alkyl, aryl, substituted aryl, heteroaryl, substituted heteroaryl, or a rifamycin pharmacophore. One of Rc and Rd is a hydrogen atom and the other is selected from hydroxyl, amino-, alkylamino, dialkylamino, or —NH-Xb-Rx. Alternatively, Rc and Rd, together with the carbon atom to which they are attached, form C=O or C=N—O-Xb-Rx. Re is $(C_1-C_6)$alkyl, substituted $(C_1-C_6)$alkyl, or -Xb-Rx. Rf is hydrogen, $(C_1-C_6)$alkyl, or substituted $(C_1-C_6)$alkyl. Rg is hydrogen, acetyl or propionyl group. Rh is methyl or methoxyl group. Ri is —CH$_2$CHO, —CH$_2$CH=N—O-Xb-Rx, —CH$_2$CH$_2$—NH-Xb-Rx. Rj is hydrogen or methyl. Rk is hydrogen or —CH$_2$—O-sugar. $R_1$ is methyl or ethyl. A specific set of pharmacophores are represented in the structural formulas shown in FIG. 3. The preferred therapeutic macrolide pharmacophore, as shown in the three formulas above, are covalently coupled to the linker or directly to the rifamycin pharmacophore through C-4", C-6, C-9, or C-9a of the macrolide. Preferred sets of linkers ("Xb") are any combination of from one to three structures shown in FIG. 1, where the left side of the linker is attached to the rifamycin molecule through a C—N, C—O or C—C bond and the right side of the linker is attached to the macrolide molecule through a C—N, C—O or C—C bond.

Another preferred $Q_3$, $Q_{11}$ and $Q_{25}$ pharmacophore comprises any of the structural formulas related to the oxazolidinone antibiotics, as shown below:

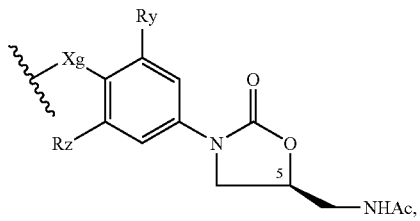

wherein Ry and Rz are independently selected from H or F and Xg is $L_3$, $L_{11}$ or $L_{25}$. The preferred oxazolidinone pharmacophore as shown in the formula above is covalently coupled or bonded to the linker $L_3$, $L_{11}$ or $L_{25}$ which in turn is covalently coupled or bonded to the rifamycin molecule. Preferred sets of linkers are any combination of from one to three structures shown in FIG. 1, where the left side of the linker is attached to the rifamycin molecule through a C—N, C—O or C—C bond and the right side of the linker is attached to the oxazolidinone molecule through a C—N, C—O or C—C bond.

Another aspect of the current invention comprises a method of treating a microbial infection in a subject; wherein the subject is any species of the animal kingdom. The microbial infection can be caused by a bacterium or microorganism. The term "subject" refers more specifically to human and animals, wherein the animals can be used for: pets (e.g. cats, dogs, etc.); work (e.g. horses, cows, etc.); food (chicken, fish, lambs, pigs, etc); and all others known in the art. The method comprises administering an effective amount of one or more compounds of the present invention to the subject suffering from a microbial infection.

DETAILED DESCRIPTION

Figure 1:
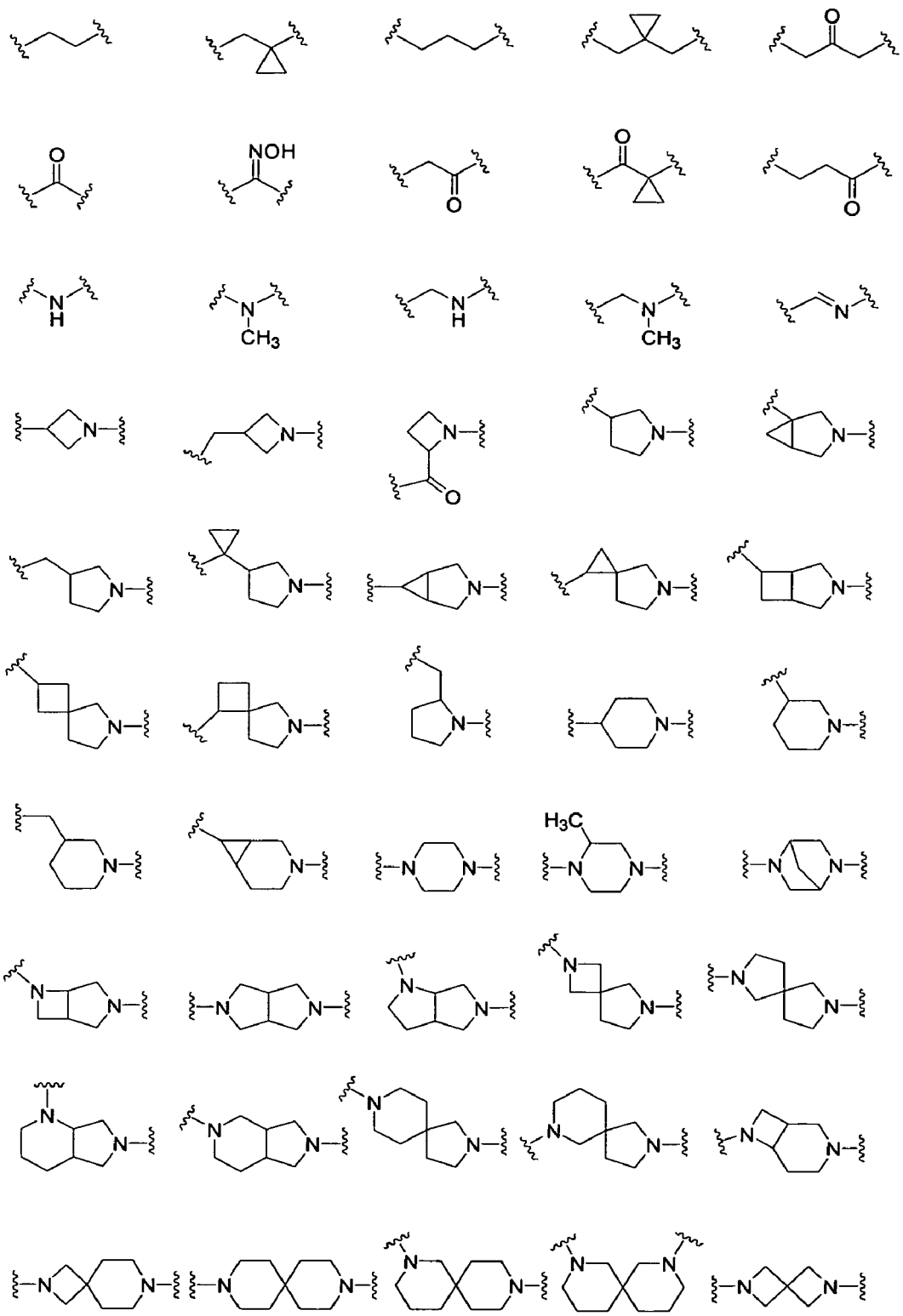
FIG. 1 shows a group of linkers, which are preferred structures for $L_3$, $L_{11}$ and $L_{25}$.

Terms:

The term "alkenyl," as used herein, refers to a monovalent straight or branched chain group containing at least one carbon-carbon double bond. The alkenyl groups of this invention can be optionally substituted.

The term "alkenylene," as used herein, refers to a bivalent straight or branched chain group containing at least one carbon-carbon double bond. The alkenylene groups of this invention can be optionally substituted.

The term "alkyl," as used herein, refers to a monovalent, saturated, straight or branched chain hydrocarbon group. Examples of alkyl group include methyl, ethyl, propyl, iso-propyl, n-butyl, iso-butyl, tert-butyl, neo-pentyl, and n-hexyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, isobutylene, and n-hexylene. The alkylene groups of this invention can be optionally substituted.

The term "alkylamino," as used herein, refers to an amino group (—$NH_2$), wherein one hydrogen atom is replaced by an alkyl group. Examples of alkylamino include methylamino, ethylamino, propylamino, and isopropylamino.

The term "alkylthio," as used herein, refers to an alkyl group, as defined herein, attached to the parent molecular group through a sulfur atom. Examples of alkylthio include methylthio, ethylthio, propylthio, and isopropylthio.

The term "alkoxy," as used herein, refers to an alkyl group, as previously defined, attached to the parent molecular group through an oxygen atom. Examples of alkoxy include methoxy, ethoxy, propoxy, iso-propoxy, n-butoxy, tert-butoxy, neo-pentoxy and n-hexoxy. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "alkynylene," as used herein, refers to a bivalent straight or branched chain group of two to six carbon atoms containing at least one carbon-carbon triple bond. Examples of alkynylene include ethynylene, propynylene, and butynylene. The alkynylene groups of this invention can be optionally substituted The term "aprotic solvent," as used herein, refers to a solvent that is relatively inert to protonic activity, i.e., not acting as a proton donor. Examples include hexane, toluene, dichloromethane, ethylene dichloride, chloroform, tetrahydrofuran, N-methylpyrrolidinone, and diethyl ether.

The term "aryl" as used herein refers to a monovalent carbocyclic aromatic group such as phenyl, naphthyl, and anthracenyl, which can be optionally substituted.

The term "arylene" as used herein refers to bivalent carbocyclic aromatic groups which can be optionally substituted.

The term "benzyl," as used herein, refers to —$CH_2C_6H_5$.

The term "benzyloxy," as used herein, refers to a benzyl group, as defined herein, attached to the parent molecular group through an oxygen atom.

The term "carboxaldehyde," as used herein, refers to —CHO.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "formyl," as used herein, refers to —CH(=O).

The term "halogen," as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur, and nitrogen, wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, and -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydroxyl," as used herein, refers to —OH.

The term "protecting group", as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (Greene and Wuts, 1991).

The term "pharmaceutically acceptable prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use.

The term "pharmaceutically acceptable salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts include salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

The term "pharmaceutically acceptable carrier," as used herein, refers to a non-toxic, inert solid, semi-solid or liquid filler, diluent, encapsulating material or formulation auxiliary of any type. Some examples of materials which can serve as pharmaceutically acceptable carriers include carbohydrates such as lactose, glucose and sucrose; starches such as corn starch and potato starch; cellulose and its derivatives such as sodium carboxymethyl cellulose, ethyl cellulose and cellulose acetate; glycols; such a propylene glycol; esters such as ethyl oleate and ethyl laureate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically, bucally, or as an oral, or nasal spray.

The term "pharmacophore" as used herein, represent a structure that is the key part of a molecule exhibiting certain pharmacological function.

The term "prodrug," as used herein, represents compounds which can be transformed in vivo to the active parent compounds defined herein.

The term "rifamycin moiety," as used herein, comprises both its phenolic and quinone forms.

The term "substituted aryl" as used herein refers to an aryl group as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refers to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

Abbreviations:

Abbreviations as used herein have the meanings known by one skilled in the art. Specifically, Ac represents acetyl group, AOC represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxylmethyl group, NMP represents N-methylpyrrolidinone, Ph represents phenyl group, Pr represents propyl group, TEA represents triethylamine, TFA represents trifluoroacetic acid, THF represents tetrahydrofuran, TMS, trimethylsilyl group, and Ts represents p-toluenesulfonyl group.

Broadly, one aspect of the present invention comprises a compound having a Formula I:

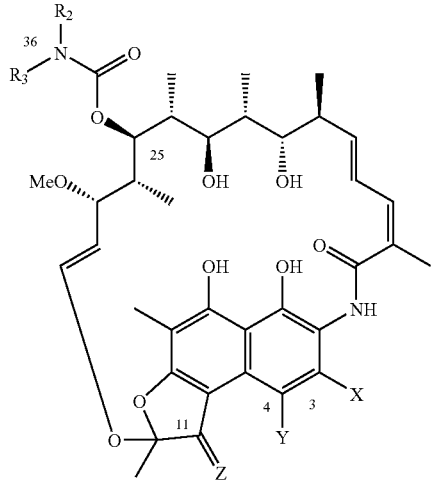

Formula I or its corresponding quinone form having a Formula II:

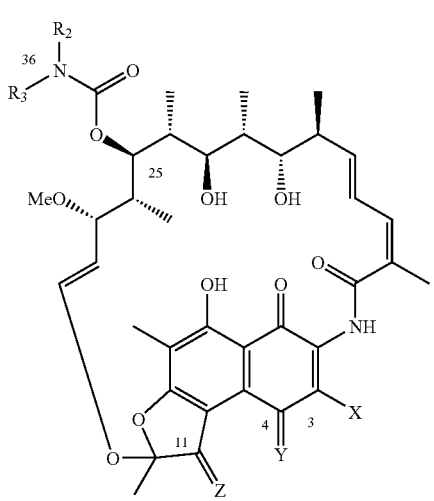

Formula II or its salts, hydrates, prodrugs or mixtures thereof;

wherein,

X is hydrogen, $-NR_{11}R_{12}$, $-CH_2NR_{11}R_{12}$, $-C=NNR_{11}R_{12}$, $-SR_{13}$, or $-L_3-Q_3$, wherein $L_3$ is any combination of 1 to 5 of the following structures: $(C_1-C_6)$alkylene, $(C_1-C_6)$alkenylene, $(C_1-C_6)$alkynylene, $(C_3-C_8)$cycloalkylene, heterocycle having 1 to 3 heteroatoms, arylene, and heteroarylene, wherein $L_3$ optionally has any combination of 1 to 3 heteroatoms selected from N, O, and S, and wherein the carbon or nitrogen atoms of $L_3$ are optionally substituted by any combination of 1 to 3 substituents selected from $(C_1-C_6)$alkyl, heterocycloalkyl, amino, $(C_1-C_6)$alkylamino, di$(C_1-C_6)$alkylamino, hydroxyl, and $(C_1-C_6)$alkoxy, wherein $R_{11}$ and $R_{12}$ independently are hydrogen, $(C_1-C_6)$alkyl, or substituted $(C_1-C_6)$alkyl, or $R_{11}$ and $R_{12}$, together with the nitrogen atom to which they are attached, form a 4- to 8-membered heterocyclic ring, optionally containing a second heteroatom selected from oxygen, nitrogen and sulfur, wherein one of the carbon or nitrogen atoms of the heterocyclic ring is optionally substituted by $(C_1-C_6)$alkyl or substituted $(C_1-C_6)$alkyl, and wherein $R_{13}$ is $(C_1-C_6)$alkyl or substituted $(C_1-C_6)$alkyl;

Y is $OR_1$, when the compound is the Formula I, wherein $R_1$ is hydrogen, $(C_1-C_6)$alkyl, substituted $(C_1-C_6)$alkyl, $-CH_2COOH$, or $-CH_2CONR_{11}R_{12}$, or Y is $=O$, when the compound is the Formula II; or X and Y, together with C-3 and C-4 of the Formula I or Formula II, join together to form a heterocyclic ring as depicted in any of Formulas III, IV, V and VI:

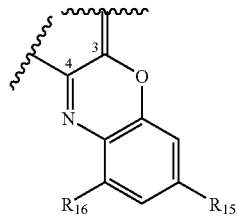

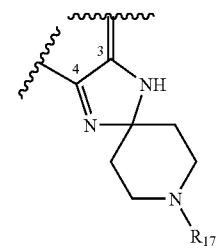

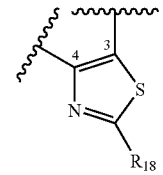

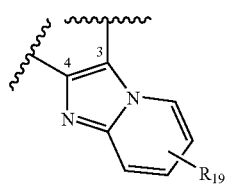

wherein $R_{15}$ is $-NR_{20}R_{21}$, $R_{16}$ is hydrogen, $(C_1-C_6)$alkyl, OH or $NH_2$, $R_{17}$ is hydrogen, $(C_1-C_6)$alkyl, $(C_1-C_6)$alkenyl, $(C_1-C_6)$alkynyl, $(C_3-C_8)$cycloalkyl, aryl, heteroaryl, or heterocycloalkyl, $R_{18}$ is $(C_1-C_6)$alkyl, $(C_1-C_6)$alkenyl, $(C_1-C_6)$alkynyl, $(C_3-C_8)$cycloalkyl, aryl, heteroaryl, $-NR_{20}R_{20}$, or heterocycloalkyl, $R_{19}$ is $(C_1-C_6)$alkyl or $-NR_{20}R_{21}$, $R_{20}$ and $R_{21}$, independently are alkyl, cycloalkyl, aryl, or heteroaryl, or $R_{20}$ and $R_{21}$, together with the nitrogen atom to which they are attached, form a 4-8 membered heterocyclic ring containing one or two heteroatoms optionally substituted with hydrogen, $(C_1-C_6)$alkyl, $(C_1-C_6)$alkenyl, $(C_1-C_6)$alkynyl, $(C_3-C_8)$cycloalkyl;

Z is $=O$, $=NH$ or $=NOR_{14}$, wherein $R_{14}$ is $-H$, alkyl, aryl, heteroaryl or $-L_{11}-Q_{11}$, wherein $L_{11}$ is any combination of 1 to 5 of the following structures: $(C_1-C_6)$alkylene, $(C_1-C_6)$alkenylene, $(C_1-C_6)$alkynylene, $(C_3-C_8)$cycloalkylene, heterocycle containing 1 to 3 heteroatoms, arylene, and heteroarylene, wherein $L_{11}$ optionally has any combination of 1 to 3 heteroatoms selected from N, O and S, and wherein the carbon or nitrogen atoms of $L_{11}$ are optionally substituted by any combination of 1 to 3 substituents selected from $(C_1-C_6)$alkyl, heterocycloalkyl, amino, $(C_1-C_6)$alkylamino, di$(C_1-C_6)$alkylamino, hydroxyl, and $(C_1-C_6)$alkoxy;

$R_2$ and $R_3$ independently are hydrogen, $(C_1-C_6)$alkyl, $(C_1-C_6)$alkenyl, $(C_1-C_6)$alkynyl, aryl, heteroaryl or $-L_{25}-Q_{25}$, wherein $L_{25}$ is any combination of 1 to 5 of the following structures: $(C_1-C_6)$alkylene, $(C_1-C_6)$alkenylene, $(C_1-C_6)$alkynylene, $(C_3-C_8)$cycloalkylene, heterocycle containing 1 to 3 heteroatoms, arylene, and heteroarylene, wherein $L_{25}$ optionally has any combination of 1 to 3 heteroatoms selected from N, O and S, and wherein the carbon or nitrogen atoms of $L_{25}$ are optionally substituted by any combination of 1 to 3 substituents selected from $(C_1-C_6)$alkyl, heterocycloalkyl, amino, $(C_1-C_6)$alkylamino, di$(C_1-C_6)$alkylamino, hydroxyl, and $(C_1-C_6)$alkoxy, or $R_2$ and $R_3$, together with the nitrogen atom to which they are attached, form a 4- to 8-membered heterocyclic ring containing one or two heteroatoms, wherein the carbon or nitrogen atoms of the ring are optionally substituted with one or more of hydrogen, $(C_1-C_6)$alkyl, $(C_1-C_6)$alkylamino, di$(C_1-C_6)$alkylamino, hydroxyl, and $(C_1-C_6)$alkoxy; and $Q_3$, $Q_{11}$ and $Q_{25}$ are a pharmacophore, therapeutic drug, or antibacterial agent comprising a quinolone, a macrolide, an oxazolidinone, an aminoglycoside, a tetracycline or any antibacterial pharmacophore.

Compositions:

The compounds of the current invention are rifamycin derivatives of Formula I and Formula II, which have been labeled at the $C_3$, $C_4$, $C_{11}$, $C_{25}$ and $C_{36}$ positions for illustration purposes. Formula I and Formula II are different in their oxidation states and can be transformed from one to the other by utilizing an oxidation or reduction reaction. In one aspect, compounds of the current invention contain many asymmetric and geometric centers. In some cases, one or more of the asymmetric or geometric centers can be converted to their opposite configurations. These stereoisomers of rifamycin are within the scope of the present invention.

EXAMPLE 1

These examples are intended for illustration purposes only and are not intended to limit the scope of this invention.

A compound having a structure of Formula I:

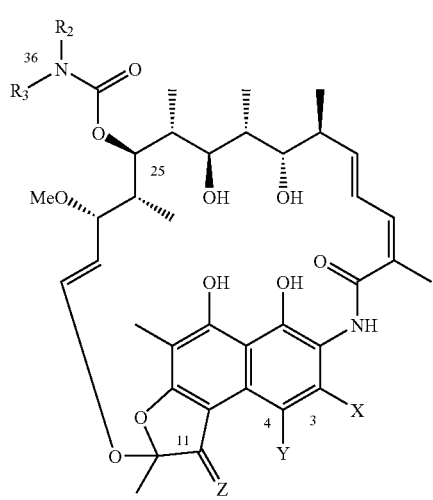

Formula I or its quinone form Formula II:

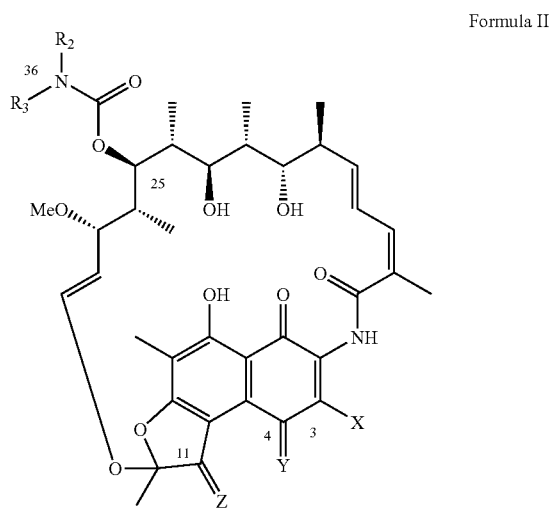

Formula II

In these structures, X represents a hydrogen, a substituent or $-L_3-Q_3$. X can be the substituent $-NR_{11}R_{12}$, $-CH_2NR_{11}R_{12}$, $-C=NNR_{11}R_{12}$, or $-SR_{13}$. $R_{11}$ and $R_{12}$ independently can be hydrogen, $(C_1-C_6)$alkyl, or substituted $(C_1-C_6)$alkyl. Alternatively, $R_{11}$ and $R_{12}$, together with the nitrogen atom to which they are attached, can form a 4- to 8-membered heterocyclic ring, optionally containing an additional heteroatom selected from oxygen, nitrogen and sulfur, wherein one of the carbon or nitrogen atoms of the heterocyclic ring is optionally substituted by $(C_1-C_6)$alkyl or substituted $(C_1-C_6)$alkyl. $R_{13}$ can be $(C_1-C_6)$alkyl or substituted $(C_1-C_6)$alkyl.

Y in Formula I represents the formula $-OR_1$. The C-4 position of rifamycins can tolerate a substituent group, and these compounds may have activity against microorganisms. $R_1$ can be hydrogen or a substituted or unsubstituted lower alkyl group of between 1 and 6 carbon atoms. In addition, $R_1$ can be a $-CH_2COOH$, or a $-CH_2C(O)NR_{11}R_{12}$ group. Compounds with these substituents can be conveniently derived from rifamycin B, although they can be prepared from other rifamycin compounds as well. The structure of the amide group $-C(O)NR_{11}R_{12}$ herein can be varied from a simple amide, wherein $R_{11}$ and $R_{12}$ are both hydrogen atoms, to a more complex structure, wherein either one or both $R_{11}$ and $R_{12}$ independently are lower alkyl groups between 1 to 6 carbon atoms. The alkyl groups can be substituted by a variety of substituent groups. Examples of the substituent groups include alkyl, substituted alkyl, amino, alkylamino, dialkylamino, hydroxyl, alkoxy, or halogens. Furthermore, $R_{11}$ and $R_{12}$ can join together with the nitrogen atom to which they are attached to form a 4- to 8-membered heterocyclic ring. This ring can optionally contain one additional heteroatom selected from oxygen, nitrogen and sulfur, wherein one of the carbon or nitrogen atoms is optionally substituted by a lower alkyl or substituted lower alkyl group. A preferred Y in Formula II is $=O$.

In the above Formulas I and II, X and Y together may form heterocyclic ring structures having Formula III, IV, V or VI:

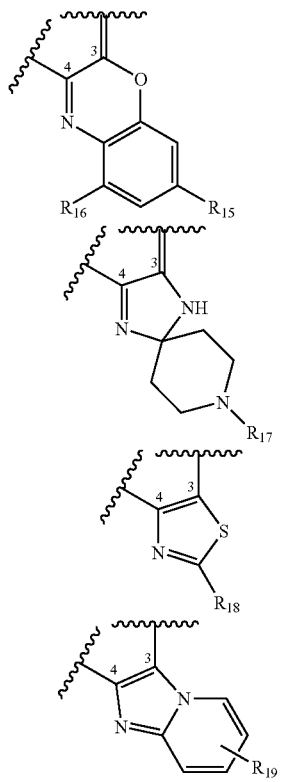

Formula III-VI

For clarity, structures III-VI are illustrated to show a portion of the original structure of Formulas I and II. In particular, structures III-VI show the C-3 and C-4 positions of the rifamycin of Formulas I and II. In these structures, $R_{15}$ is a group of the formula —$NR_{20}R_{21}$. $R_{16}$ is hydrogen, ($C_1$-$C_6$) alkyl, OH or $NH_2$. $R_{17}$, $R_{20}$, and $R_{21}$ independently are ($C_1$-$C_6$)alkyl, ($C_1$-$C_6$)alkenyl, ($C_1$-$C_6$)alkynyl, or ($C_3$-$C_8$) cycloalkyl. Alternatively, $R_{20}$ and $R_{21}$, together with the nitrogen to which they are attached, may form a 4-8 membered heterocyclic ring containing one or two additional heteroatoms, wherein the nitrogen atoms are optionally substituted with hydrogen, ($C_1$-$C_6$)alkyl, ($C_1$-$C_6$)alkenyl, ($C_1$-$C_6$)alkynyl, or ($C_3$-$C_8$)cycloalkyl. $R_{18}$ is ($C_1$-$C_6$)alkyl, ($C_1$-$C_6$)alkenyl, ($C_1$-$C_6$)alkynyl, ($C_3$-$C_8$)cycloalkyl, ($C_1$-$C_5$) alkylheterocycle, or —$NR_{20}R_{21}$. $R_{19}$ is ($C_1$-$C_6$)alkyl, ($C_1$-$C_6$)alkenyl, ($C_1$-$C_6$)alkynyl, ($C_3$-$C_8$)cycloalkyl, or —$NR_{20}R_{21}$.

Z in the above Formulas I and II can be =O, =NH or =$NOR_{14}$. $R_{14}$ can be —H, alkyl, aryl, heteroaryl or —$L_{11}$-$Q_{11}$.

$R_2$ and $R_3$ in the above structures are independently selected from a group consisting of hydrogen, ($C_1$-$C_6$)alkyl, ($C_1$-$C_6$)alkenyl, ($C_1$-$C_6$)alkynyl, aryl, heteroaryl, all of which may be optionally substituted, and —$L_{25}$-$Q_{25}$. Alternatively, $R_2$ and $R_3$ can join together with the nitrogen to which they are attached to form a 4- to 8-membered heterocyclic ring containing one or two heteroatoms, wherein the carbon or nitrogen atoms of the ring are optionally substituted with hydrogen, ($C_1$-$C_6$)alkyl, ($C_1$-$C_6$)alkylamino, di($C_1$-$C_6$)alkylamino, hydroxyl, ($C_1$-$C_6$)alkoxy or —$L_{25}$-$Q_{25}$. $Q_{25}$ is another antibacterial agent.

The linker groups $L_3$, $L_{11}$, and $L_{25}$ can be groups with various length, rigidity and properties. The linker groups may be any combination of 1 to 5 of the following structures: ($C_1$-$C_6$)alkylene, ($C_1$-$C_6$)alkenylene, ($C_1$-$C_6$)alkynylene, ($C_3$-$C_8$)cycloalkylene, heterocycle having 1 to 3 heteroatoms, arylene, and heteroarylene. The linker groups optionally can have any combination of 1 to 3 heteroatoms selected from N, O and S. The carbon or nitrogen atoms of the linker groups optionally can be substituted by any combination of 1 to 3 substituents selected from ($C_1$-$C_6$) alkyl, heterocycloalkyl, amino, ($C_1$-$C_6$)alkylamino, di($C_1$-$C_6$)alkylamino, hydroxyl, and ($C_1$-$C_6$)alkoxy. Examples of the linker groups are any combination of from one to three structures shown in FIG. 1.

As illustrated by Formula I and Formula II, the left-hand side of the linker group $L_3$, $L_{11}$, or $L_{25}$ is covalently bonded or attached to the rifamycin pharmacophore and the right-hand side of the linker is covalently bonded or attached to an antibiotic pharmacophore represented by $Q_3$, $Q_{11}$ or $Q_{25}$. Pharmacophore $Q_3$, $Q_{11}$, or $Q_{25}$ can be any structure associated with an antibacterial agent. Examples of pharmacophores include structures associating to the macrolide class, the fluoroquinolone class, the non-fluoroquinolone class, the oxazolidinone class, the tetracycline class, the aminoglycoside class, the beta-lactam class, the sulfonamide class, the trimethoprim class, the glycopeptide class, the lipopeptide class, and others.

In a preferred embodiment, the pharmacophore $Q_3$, $Q_{11}$ or $Q_{25}$ is a structure related to the fluoroquinolone or non-fluoroquinolone class of antimicrobial agents selected from Formula VII, VIII and VIX:

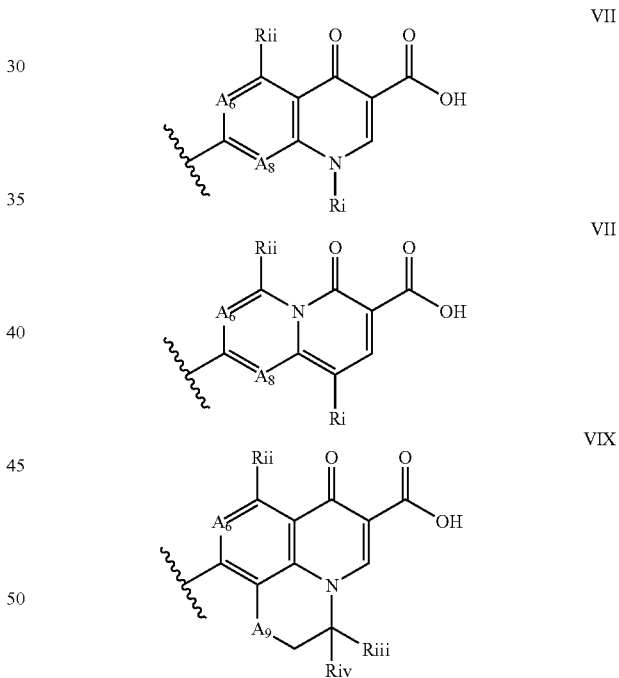

The substituents or groups in Formulas VII, VIII and VIX are as follows: Ri represents ($C_1$-$C_6$)alkyl, ($C_3$-$C_6$)cycloalkyl, substituted ($C_3$-$C_6$)cycloalkyl, aryl, substituted aryl, heteroaryl, or substituted heteroaryl; Rii represents a hydrogen, halogen, amino, nitro or methyl group; Riii and Riv independently represent hydrogen or ($C_1$-$C_6$)alkyl, or Riii and Riv, together with the carbon atom to which they are attached, form a 3- to 6-membered ring; $A_6$ represents C—H, C—F, or N; $A_8$ represents C—H, C—F, C—Cl, C-Me, C—OMe, C—OCH$_2$F, C—OCHF$_2$, or N; and $A_9$ represents CH$_2$, O or S.

Figure 2:
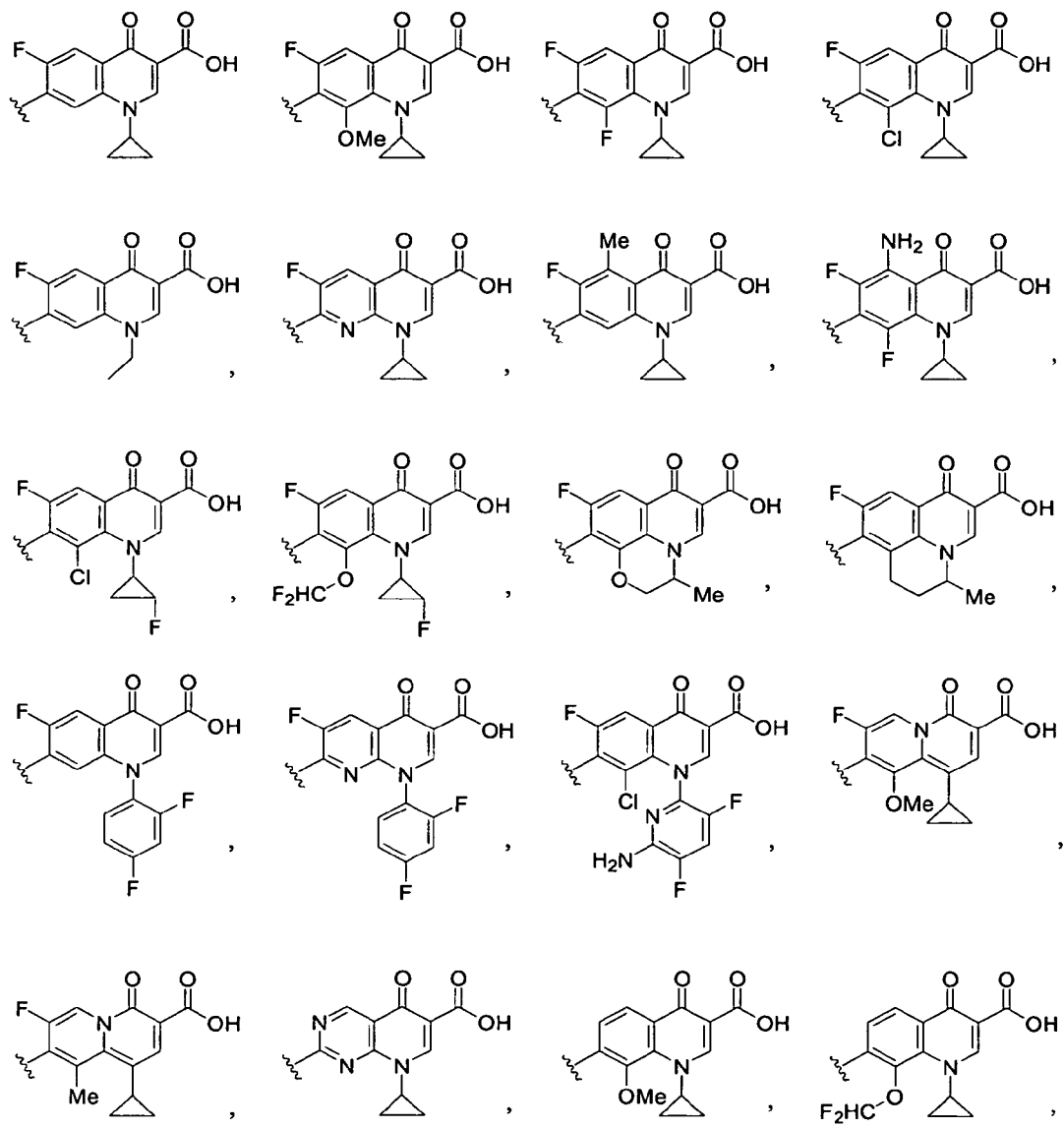
FIG. 2 shows a group of quinolone pharmacophores, which are preferred structures for $Q_3$, $Q_{11}$ and $Q_{25}$.

In another more preferred embodiment, $Q_3$, $Q_{11}$, and $Q_{25}$ independently are any quinolone structure illustrated in FIG. 2, and linkers $L_3$, $L_{11}$ and $L_{25}$ independently are any combination of from one to three structures shown in FIG. 1, wherein the left-hand side of the linker group is attached to the rifamycin pharmacophore and the right-hand side of the linker group is attached to the quinolone structure.

In another preferred embodiment, $Q_3$, $Q_{11}$, and $Q_{25}$ independently are any structure related to the macrolide class of antibiotics, which can be a 14-membered ring, a 15-membered ring or a 16-membered ring macrolide, as shown below:

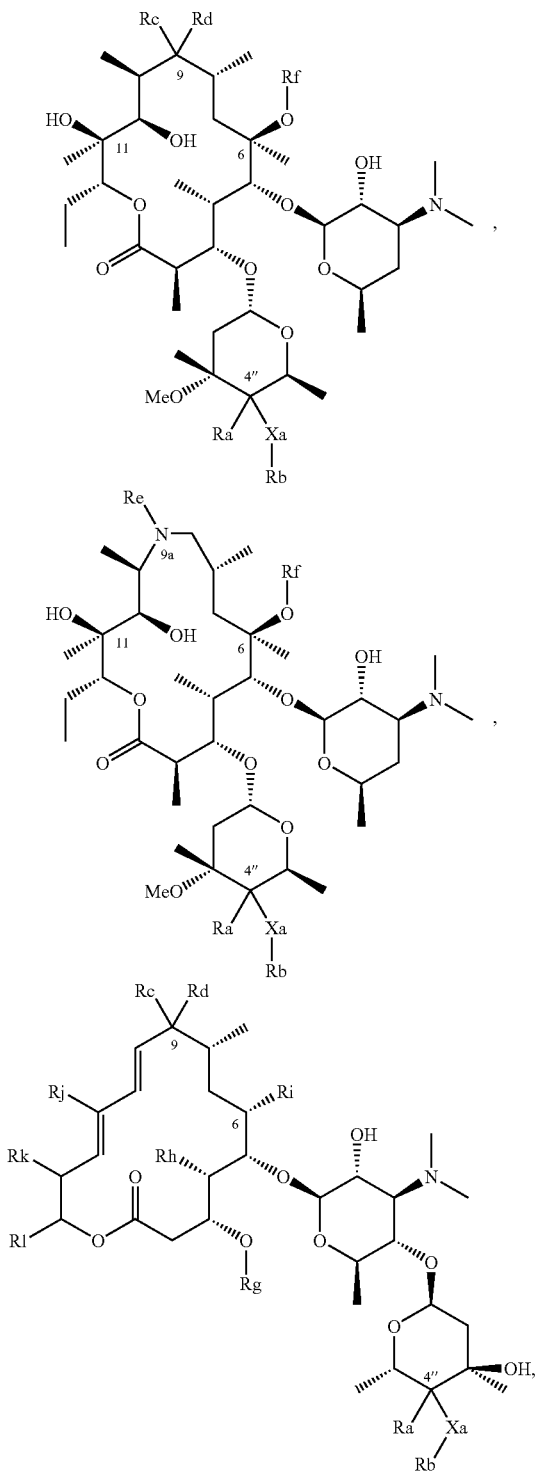

wherein the substituents in the above figure are as follows: Ra is hydrogen or hydroxyl; Xa is —O—, —NH—, or —CH$_2$NH—; Rb is -Xb-Rx, wherein Xb is absent or is the linker group $L_3$, preferably having any combination of from one to three of the structures shown in FIG. 1; Rx is ($C_1$-$C_6$)alkyl, substituted ($C_1$-$C_6$)alkyl, aryl, substituted aryl, heteroaryl, substituted heteroaryl, or a rifamycin pharmacophore; one of Rc or Rd is a hydrogen atom while the other constituent is hydroxyl, amino, alkylamino, dialkylamino, or —NH-Xb-Rx; or both Rc and Rd, together with the carbon atom to which they are attached, form C=O or C=N—O—X-Rx, wherein Xb and Rx are defined above; Re is ($C_1$-$C_6$)alkyl, substituted ($C_1$-$C_6$)alkyl, or -Xb-Rx, wherein Xb and Rx are as defined above; Rf is hydrogen, ($C_1$-$C_6$) alkyl, or substituted ($C_1$-$C_6$)alkyl; Rg is a hydrogen, acetyl or propionyl group; Rh is a methyl or methoxyl group; Ri is —CH$_2$CHO, —CH$_2$CH=N—O-Xb-Rx, or —CH$_2$CH$_2$—NH-Xb-Rx, wherein Xb and Rx are as defined above; Rj is hydrogen or methyl; Rk is hydrogen or —CH$_2$—O-sugar; and Rl is methyl or ethyl.

Examples of macrolide antibiotics include erythromycin, erythromycylamine, clarithromycin, azithromycin, roxithromycin, dirithromycin, flurithromycin, oleandomycin, telithromycin, cethromycin, leucomycin, spiramycin, tylosin, rokitamycin, miokamycin, josamycin, rosaramycin, virginiamycin, and midecamycin. The preferred linking points on a macrolide structure are the C-4", C-6, C-9 or C9a position as illustrated above.

Figure 3:
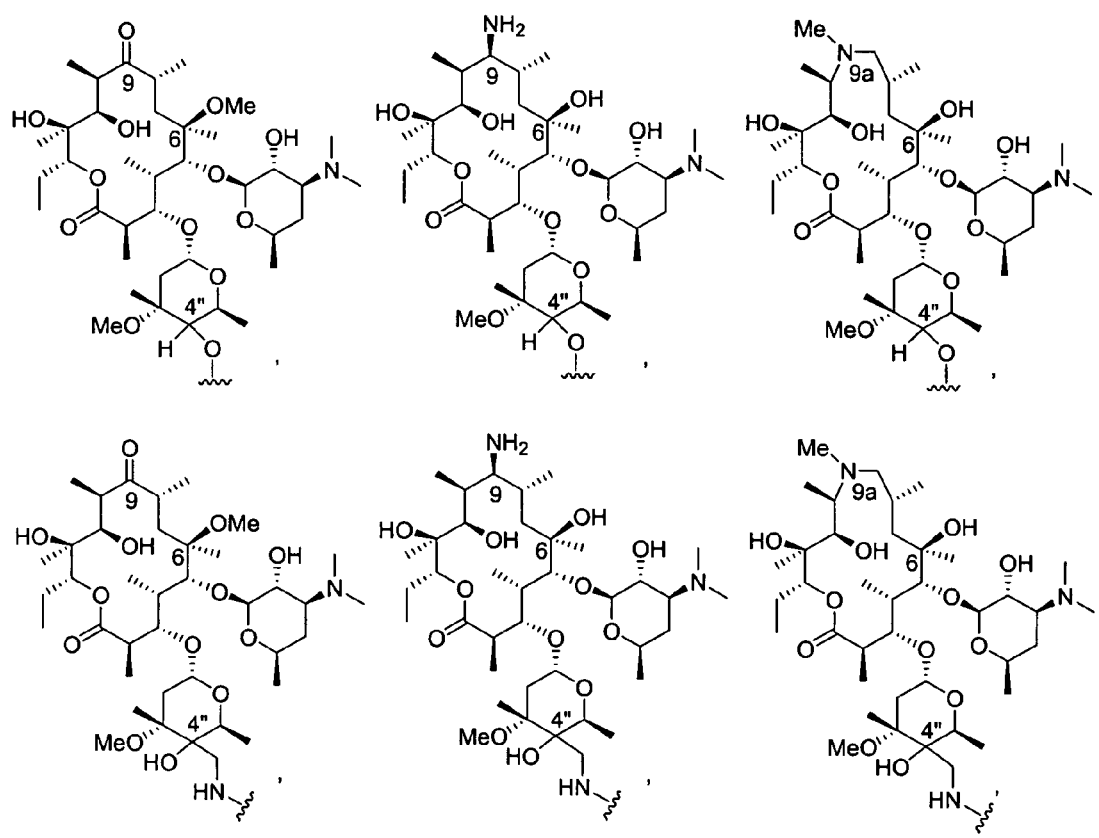
FIG. 3 shows a group of macrolide pharmacophores, which are preferred structures for $Q_3$, $Q_{11}$ and $Q_{25}$.

In a more preferred embodiment, pharmacophores $Q_3$, $Q_{11}$ and $Q_{25}$ independently are a macrolide group selected from any of those shown in FIG. 3 and linkers $L_3$, $L_{11}$ and $L_{25}$ independently are any combination of from one to three structures shown in FIG. 1, wherein the left-hand side of the linker group is attached to the rifamycin structure and the right-hand side of the linker group is attached to the macrolide structure.

In another preferred embodiment, the pharmacophores $Q_3$, $Q_{11}$ and $Q_{25}$ independently comprise a structure related to the oxazolidinone antibiotics, as shown below:

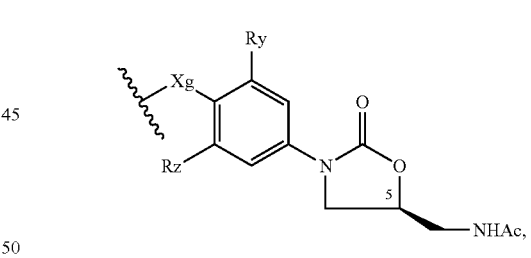

wherein Ry and Rz are independently selected from H or F, and Xg is $L_3$, $L_{11}$ or $L_{25}$. The preferred oxazolidinone pharmacophore as shown in the formula above is covalently coupled or bonded to the appropriate linker $L_3$, $L_{11}$, or $L_{25}$ which in turn is covalently coupled or bonded to the rifamycin molecule. Preferred sets of linkers $L_3$, $L_{11}$, and $L_{25}$ are any combination of from one to three structures shown in FIG. 1, in which the left side of the linker is attached to the rifamycin molecule through a C—N, C—O or C—C bond, and the right side of the linker is attached to the oxazolidinone molecule through a C—N, C—O or C—C bond.

Preferred antibiotic compounds of the invention are as follows: 25-O-desacetyl-(1-carbonyl-4-methyl-piperazine) 3-morpholino rifamycin S, 25-O-desacetyl-(1-carbonylisobutylamino) 3-morpholino rifamycin S, 25-O-desacetyl-(carbonyl-allylamino) 3-morpholino rifamycin S, 25-O-desacetyl(1-carbonyl-2-(4-methyl-piperazin-1-yl)-ethylamine) 3-morpholino rifamycin S, 25-O-desacetyl(1-carbonyl-2-diethylamine) 3-morpholino rifamycin S, 25-O-desacetyl-(1-carbonyl-3-imidazol-1-yl-propylamine) 3-morpholino rifamycin S, 25-O-desacetyl(1-carbonyl-1-(4-fluorophenyl)-piperazine) 3-morpholino rifamycin S, 25-O-desacetyl-(carbonyl-1-(3-trifluoromethylbenzylamino)) 3-morpholino rifamycin S, 25-O-desacetyl-(carbonyl-1-pyrrolidino) 3-morpholino rifamycin S, 25-O-desacetyl (carbonyl-benzyl) 3-morpholino rifamycin S, 25-O-desacetyl-(4-carbonyl-1-cyclopropyl-6-fluoro-4-oxo-7-piperazin-1-yl-1,4-dihydro-quinoline-3-carboxylic acid) 3-morpholino rifamycin S, 25-O-desacetyl-(8-chloro-1-cyclopropyl-7-[4-(1-carbonyl)-piperazin-1-yl]-6-fluoro-4-oxo-1,4-dihydro-quinoline-3-carboxylic acid) 3-morpholino rifamycin S, 25-O-desacetyl-(1-carbonyl-(2-pyridin-2-yl-ethylamine)) 3-morpholino rifamycin S, 25-O-desacetyl-(1-carbonyl-2-thiophen-2-yl-ethylamine) 3-morpholino rifamycin S, 25-O-desacetyl-(1-carbonyl-2-aminoethanol) 3-morpholino rifamycin S, 25-O-desacetyl-(carbonyl-methylamino) 3-morpholino rifamycin S, 25-O-desacetyl-(carbonyl-4-chlorobenzyl) 3-morpholino rifamycin S, 25-O-desacetyl-(carbonyl-naphthalen-1-ylmethyl-amino) 3-morpholino rifamycin S, 25-O-desacetyl-(carbonyl-3-phenylpropylamino) 3-morpholino rifamycin S, 25-O-desacetyl-(carbonyl-3-phenylethylamino) 3-morpholino rifamycin S, 25-O-desacetyl-(carbonyl-4-methoxybenzylamino) 3-morpholino rifamycin S, 25-O-desacetyl-((2-amino-ethyl)-carbamic acid 6-[6-(4-dimethylamino-3-hydroxy-6-methyl-tetrahydro-pyran-2-yloxy)-14-ethyl-12, 13-dihydroxy-7-methoxy-3,5,7,9,11,13-hexamethyl-2,10-dioxo-oxacyclotetradec-4-yloxy]-4-methoxy-2,4-dimethyl-tetrahydro-pyran-3-yl ester) 3-morpholino rifamycin S, 25-O-desacetyl-(carbonyl-1-cyclopropyl-6-fluoro-8-methoxy-7-(3-methyl-piperazin-1-yl)-4-oxo-1,4-dihydro-quinoline-3-carboxylic acid) 3-morpholino rifamycin S, 25-O-desacetyl-(carbonyl-2-ethyl-octahydro-pyrrolo[3,4-c] pyrrole) 3-morpholino rifamycin S, 25-O-desacetyl-(carbonyl-N,N-dimethylethylenediamine) 3-morpholino rifamycin S, 25-O-desacetyl-(carbonyl-2-(1-methyl-pyrrolidin-2-yl)-ethylamine) 3-morpholino rifamycin S, 25-O-desacetyl-(carbonyl-2-pyrrolidin-1-yl-ethylamine) 3-morpholino rifamycin S, 25-O-desacetyl-(carbonyl-1-benzyl-piperidin-4-ylamine) 3-morpholino rifamycin S, 25-O-desacetyl-(carbonyl-4-phenyl-butylamine) 3-morpholino rifamycin S, 25-O-desacetyl-(carbonyl-[1,4']bipiperidinyl) 3-morpholino rifamycin S, 25-O-desacetyl-(carbonyl-(4-aminomethyl-phenyl)-dimethyl-amine) 3-morpholino rifamycin S, 25-O-desacetyl-(carbonyl-N'-benzyl-N,N-dimethyl-ethane-1,2-diamino) 3-morpholino rifamycin S, 25-O-desacetyl-(carbonyl-2-(4-chloro-phenyl)-ethylamine) 3-morpholino rifamycin S, 25-O-desacetyl-(carbonyl-3-chloro-benzylamine) 3-morpholino rifamycin S, 25-O-desacetyl-(carbonyl-4-nitro-benzylamine) 3-morpholino rifamycin S, 25-O-desacetyl-(carbonyl-N-(quinolin-3-yl)methylamino)) 3-morpholino rifamycin S, 25-O-desacetyl-(carbonyl-1-cyclopropyl-6-fluoro-4-oxo-7-piperazin-1-yl-1, 4-dihydro-quinoline-3-carboxylic acid) 3-morpholino rifamycin S, 25-O-desacetyl-(carbonyl-prop-2-ynylamino) 3-morpholino rifamycin S, 25-O-deacetyl cyclic-21,23-(1-methylethylidene acetal)-(carbonyl-prop-2-ynylamino)-3-morpholino-rifamycin S, 25-O-desacetyl-(carbonyl-[3-(3-amino-prop-1-ynyl)-phenyl]-methanol) 3-morpholino rifamycin S, 25-O-desacetyl-(carbonyl-3-quinolin-3-yl-prop-2-ynylamine) 3-morpholino rifamycin S, 25-O-desacetyl-(carbonyl-C-[3-(2-methoxy-phenyl)-isoxazol-5-yl]-methylamino) 3-morpholino rifamycin S, 25-O-desacetyl-(carbonyl-C-(3-pyridin-2-yl-isoxazol-5-yl)-methylamino) 3-morpholino rifamycin S, 25-O-desacetyl-(carbonyl-(3-acetyl-isoxazol-5-ylmethylamino) 3-morpholino rifamycin S, 25-O-desacetyl-(carbonyl-N-hydroxy-N'-phenyl-4-(2-piperazin-1-yl-ethylamino)-3-trifluoromethyl-benzamidine) 3-morpholino rifamycin S, 25-O-desacetyl-(carbonyl-N-(2-methyl-1H-indol-5-yl)-4-piperazin-1-yl-3-trifluoromethyl-benzamide) 3-morpholino rifamycin S, 25-O-desacetyl-(carbonyl-N-(5-methoxy-pyridin-3-yl)-4-piperazin-1-yl-3-trifluoromethyl-benzamide) 3-morpholino rifamycin S, 25-O-desacetyl-(carbonyl-N-(4-piperidone) cyclic-21,23-(1-methylethylidene acetal) 3-morpholino rifamycin S 25-O-desacetyl-(carbonyl-N-(1-cyclopropyl-6-fluoro-8-methoxy-7-(octahydro-pyrrolo[3,4-b]pyridin-6-yl)-4-oxo-1, 4-dihydro-quinoline-3-carboxylic acid) 3-morpholino rifamycin S, 25-O-desacetyl-(carbonyl-N-(7-(3-amino-pyrrolidin-1-yl)-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(1-cyclopropyl-6-fluoro-4-oxo-7-piperazin-1-yl-1,4-dihydro-quinoline-3-carboxylic acid) 3-morpholino rifamycin S, 25-O-desacetyl-(carbonyl-N-(7-(4-amino-piperidin-1-yl)-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(7-(3-amino-piperidin-1-yl)-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(1-cyclopropyl-6-fluoro-8-methoxy-4-oxo-7-piperazin-1-yl-1,4-dihydro-quinoline-3-carboxylic acid) 3-morpholino rifamycin S, 25-O-desacetyl-(carbonyl-N-(3-pyrrolidone) cyclic-21,23-(1-methylethylidene acetal)-(3-morpholino rifamycin S, 25-O-desacetyl-(carbonyl-N-(1-cyclopropyl-6-fluoro-8-methoxy-4-oxo-7-(4-pyrrolidin-3-yl-piperazin-1-yl)-1,4-dihydro-quinoline-3-carboxylic acid 3-morpholino rifamycin S, 25-O-desacetyl-(carbonyl-N-(7-[3-(2-amino-acetylamino)-pyrrolidin-1-yl]-8-chloro-1-cyclopropyl-6-fluoro-4-oxo-1,4-dihydro-quinoline-3-carboxylic acid 3-morpholino rifamycin S, 25-O-desacetyl-(carbonyl-N-(7-[4-(2-amino-acetyl)-piperazin-1-yl]-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(7-[4-(Azetidine-3-carbonyl)-3-methyl-piperazin-1-yl]-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(7-[4-(azetidine-3-carbonyl)-piperazin-1-yl]-1-cyclopropyl-6-fluoro-8-methoxy-4-oxo-1,4-dihydro-quinoline-3-carboxylic acid) 3-morpholino rifamycin S, 25-O-desacetyl-(carbonyl-N-(7-(3-amino-pyrrolidin-1-yl)-8-chloro-1-cyclopropyl-6-fluoro-4-oxo-1,4-dihydro-quinoline-3-carboxylic acid) 3-morpholino rifamycin S, 25-O-desacetyl-(carbonyl-N-(8-chloro-1-cyclopropyl-6-fluoro-7-(3-formylamino-pyrrolidin-1-yl)-4-oxo-1,4-dihydro-quinoline-3-carboxylic acid)-3-morpholino-11-deoxy-11-hydroxyiminorifamycin S, 25-O-desacetyl-(carbonyl-N-(2-dimethylamino-ethyl)-3-morpholino-11-deoxy-11-hydroxyiminorifamycin S.

EXAMPLE 2

Administration to a Subject

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animals in single or in divided doses can be in amounts, for example, from about 0.1 to about 100 mg/kg body weight or preferably from about 0.25 to about 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administrated orally, rectally, parenterally, intracisternally, intravaginally, intraperitoneally, topically, bucally, or as an oral or nasal spray.

Biological Activity

Representative compounds were assayed for antimicrobial activity as follows: Minimum Inhibitory Concentrations ("MICs") were determined by the microbroth dilution method as per NCCLS guidelines (National Committee for Clinical Laboratory Standards, 2000), except that all growth incubations were conducted at 37° C. Bacterial cultures were tested in the following bacteriological media: S. aureus, S. epidermidis, and E. coli in Cation-Adjusted Mueller-Hinton Broth, S. pneumoniae in THY Broth supplemented with 1 mg/mL catalase under 5% $CO_2$ atmosphere, S. pyogenes in THY Broth, E. faecalis in BHI Broth, H. influenzae in BHI Broth supplemented with 0.75 µL of 1 mg/mL NAD and 150 µL of 1 mg/ml hematin per 5 mL, and M smegmatis in Middlebrook Broth plus ADC Enrichment. The antimicrobial activity of the example compounds of the current invention are shown in Table 1.

TABLE 1

Antimicrobial activity (MIC, mcg/ml) of selected compounds

| Organism | | rifampin | cipro-floxacin | Example 4-69 |
|---|---|---|---|---|
| Staphylococcus aureus ATCC29213 | rifS | 0.008 | 0.25 | 0.002-1.95 |
| Staphylococcus aureus ATCC29213 rpoB$^{H418Y}$ | rifR | 7.8 | 0.25 | 2.0->64 |
| Staphylococcus aureus ATCC29213 rpoB$^{D417Y}$ | rifR | >64 | 0.25 | 0.98->64 |
| Staphylococcus epidermidis ATCC12228 | rifS | 0.03 | 0.125 | 0.0001-0.8 |
| Streptococcus pneumoniae ATCC6303 | rifS | 0.061 | 1 | 0.00006-25.5 |
| Streptococcus pyogenes ATCC19615 | rifS | 0.013 | 0.5 | 0.002-2 |
| Enterococcus faecalis ATCC29212 | rifS | 0.98 | 0.5 | 0.25-62 |
| Haemophilus influenzae ATCC10211 | rifS | 0.24 | 0.008 | 0.06->51 |
| Escherichia coli ATCC25922 | rifS | 16 | 0.03 | 3.9->64 |
| Mycobacterium smegmatis ATCC700084 | rifS | 64 | 0.125 | 0.063-31 |

[a] For strain MT1222 see: Ince & Hooper, Antimicrobial Agents and Chemotherapy, 2000, vol. 44, pp. 3344-50.

S. aureus ATCC 2213, S. epidermidis ATCC 12228, S. pneumoniae ATCC6303, S. pyogenes ATCC 19615 and E. faecalis ATCC 29212 are rifampin-susceptible Gram-positive strains. Rifampin exhibits excellent activity against these organisms with MICs between 0.03 and 1.3 µg/ml. The compounds of the current invention show further improved activity against these strains with MICs as low as 0.0001 µmg/ml. H. influenzae ATCC 10211 and E. coli ATCC 25922 are Gram-negative bacteria. Rifampin has intrinsic weaker activity against these organisms with MICs between 0.24 and 16 µg/ml. Compounds of the current invention also demonstrate improved activity against these strains with MICs as low as 0.06 µg/ml. In addition, rifampin exhibits low activity against a mycobacterial strain M smegamatis ATCC 700084 with a MIC 64 µg/ml. Certain compounds of the current invention show potent activity against this strain with a MIC 0.06 µg/ml.

Most importantly, compounds of the current invention demonstrate excellent activity against rifampin-resistant organisms. S. aureus ATCC 29213 RpoB$^{H418Y}$ is a rifampin-resistant strain with a mutation in RNA polymerase. This mutation results in a significant increase in the MIC for rifampin to 8 µg/ml. Compounds of the current invention exhibit potent activity against this strain with a MIC as low as 2 µg/ml. S. aureus ATCC 29213 RpoB$^{D417Y}$ is a high level rifampin-resistant strain due to a RNA polymerase mutation with a MIC >64 µg/ml for rifampin. Compounds of the current invention are potent against this highly rifampin-resistant strain with MICs in the 0.98 µg/ml level.

EXAMPLE 3

Synthetic Methods

The compounds of the current invention can be better understood in connection with the following synthetic schemes. The synthetic procedures shown in Schemes 1 to 8 are for illustration purposes and are not intended to limit the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups. The groups Ra, Rc, Rd, Re, Rf, Rp, $R_{29}$, $R_{30}$, $R_{31}$, $R_{32}$, $R_{33}$, Ry, Rz, Rx, $L_3$, $L_{11}$, $L_{25}$, $Q_3$, $Q_{11}$, $Q_{25}$, Xa, Xg and $X_2$ in schemes 1 to 8 are defined below or elsewhere.

Figure 4:
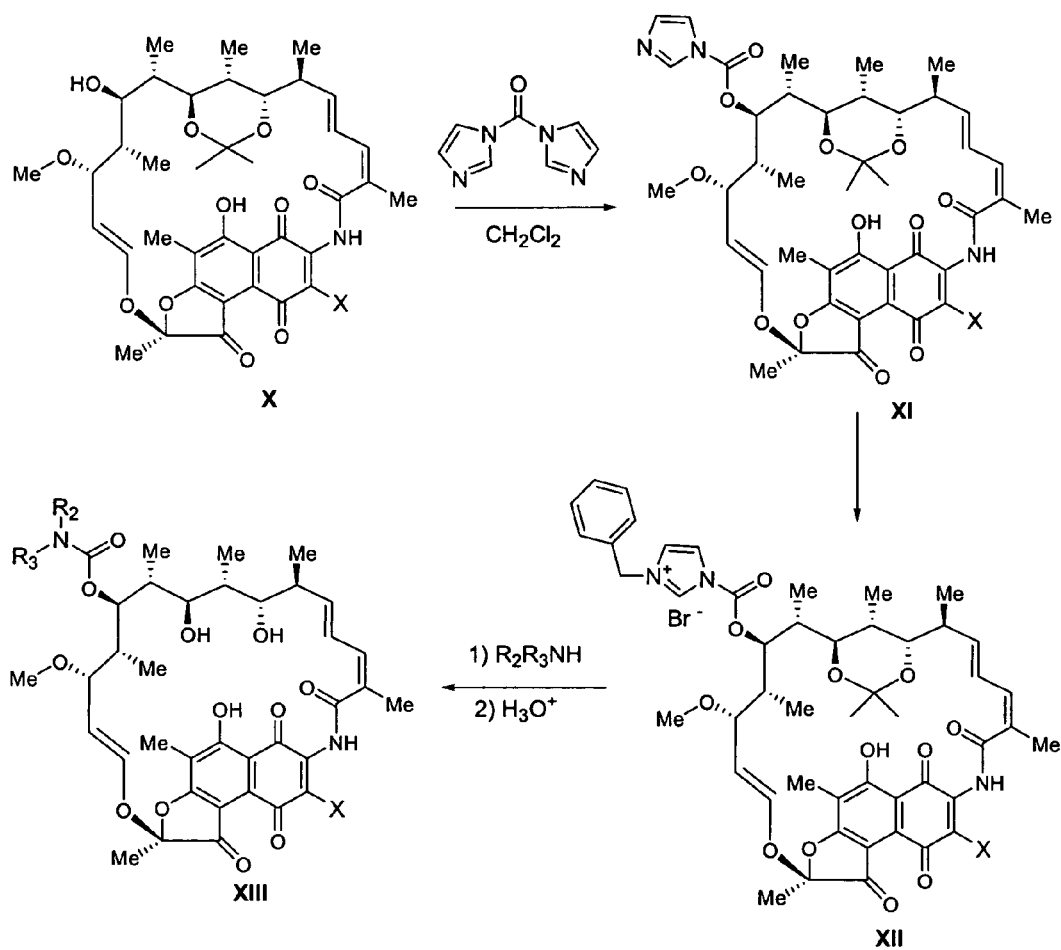
FIG. 4 shows Scheme 1, wherein a rifamycin derivative with a C-25 carbamate linkage is constructed.

Scheme 1, shown in FIG. 4, illustrates that compounds of Formula XIII are prepared by reacting a 25-O-desacetyl rifamycin S acetonide of Formula X, with carbonyl diimidazole to give the imidazole carboxylate, XI. The imidazole is activated by treating the compound with an alkylating agent such as benzyl bromide, or trimethyloxonium tetrafluoroborate, to give XII. The activated carbamate is treated with an amine to give the desired carbamate, XIII. The acetonide can be removed with mild aqueous acid hydrolysis or the product can be further functionalized as shown in Schemes 2 to 8.

Figure 5:
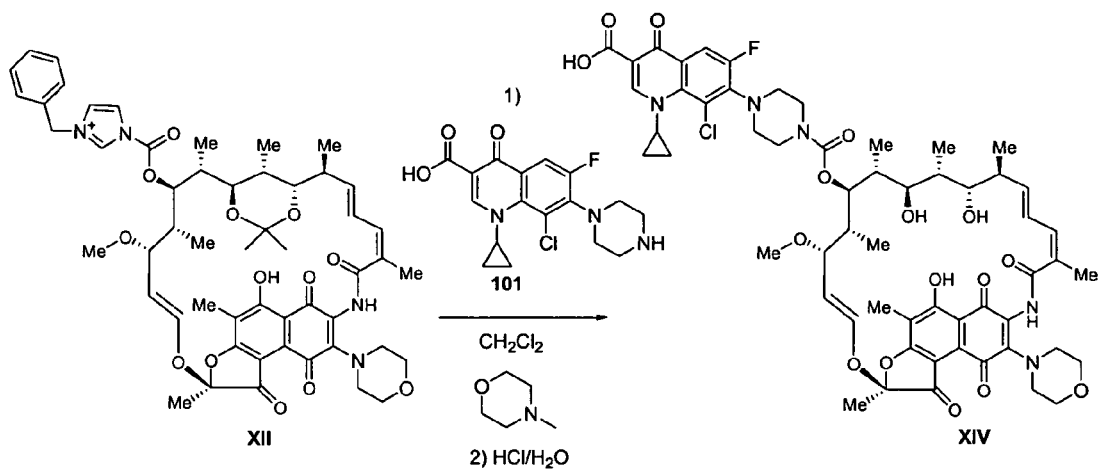
FIG. 5 shows Scheme 2, wherein a rifamycin derivative reacts with a quinolone compound.

One specific example of the current invention is illustrated by Scheme 2, shown in FIG. 5, where rifamycin 25-O-carbonyl-1-benzy-3H-imidazol-1-ium bromide (XII, X is morpholino) reacts with quinolone compounds of formula 101 to give products of Formula XIV. It will be apparent to one skilled in the art that rifamycin 25-O-carbonyl-1-benzy-3H-imidazol-1-ium bromide (XII, X is morpholino) can be replaced by other rifamycin analogs of Formula XII and the quinolone compound 101 can be replaced by other pharmacophore within the gyrase/topoisomerase IV inhibitor family. The reaction is performed in an aprotic solvent catalyzed by an organic or inorganic base. Examples of solvents suitable for this reaction are DCM, DCE, THF, DMSO, DMF, and NMP. Examples of bases are NMM, TEA, DBU, etc. Under certain circumstances, excess of 101 can be used as base.

Figure 6:
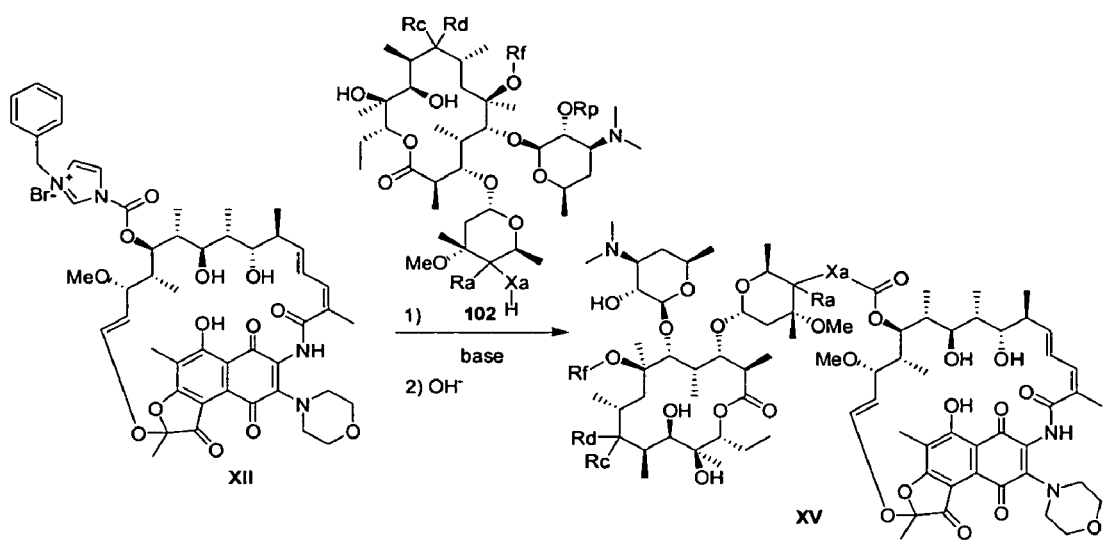
FIG. 6 shows Scheme 3, wherein a rifamycin derivative reacts with a macrolide compound.

Another specific example is illustrated by Scheme 3, shown in FIG. 6, where rifamycin 25-O-carbonyl-1-benzy-3H-imidazol-1-ium bromide (XII, $X_3$=morpholino) reacts with a macrolide compound of formula 102, wherein Rp is a hydrogen or a hydroxyl protecting group such as acetyl or benzoyl, to give product of Formula XV. It will be apparent to one skilled in the art that 25-O-(carbonyl-1-benzy-3H-imidazol-1-ium bromide) rifamycin S (XII, $X_3$=morpholino) can be replaced by other rifamycin analogs of Formula XII and the macrolide compound 102 can be replaced by other pharmacophores within the macrolide family that include 14-membered ring, 15-membered ring and 16-membered ring macrolide structures. It will be also apparent to one skilled in the art that the macrolide structure can be linked at another position such as the 6-position, the 9-position and the 11-position. The reaction is performed in an aprotic solvent catalyzed by an organic or inorganic base. Examples of solvents suitable for this reaction are DCM, DCE, THF, DMSO, DMF, NMP, acetonitrile or any combination of the above. Examples of bases are TEA, NMM or other tertiary amines. Under certain circumstances, excess of 102 can be used as base.

Figure 7:
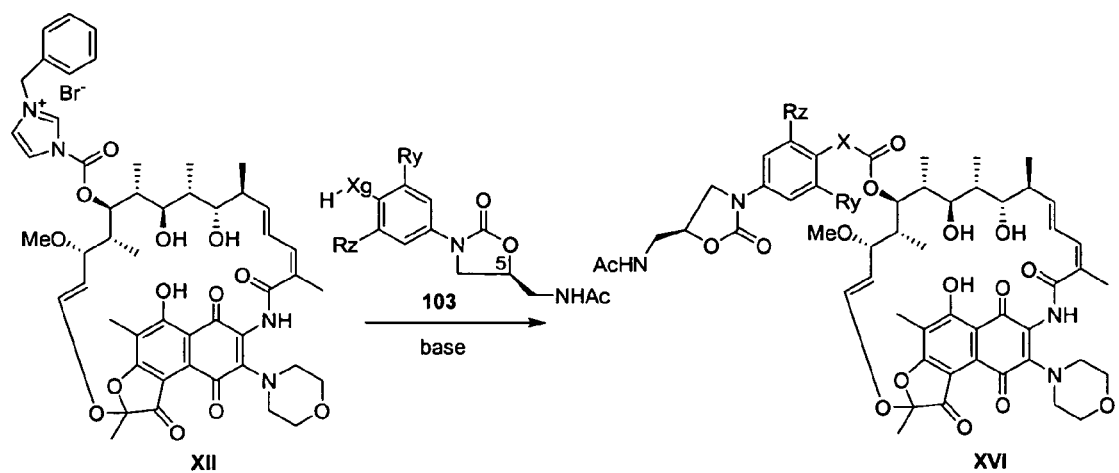
FIG. 7 shows Scheme 4, wherein a rifamycin derivative reacts with an oxazolidinone compound.

Yet another specific example of the current invention is illustrated by Scheme 4, shown in FIG. 7, where 25-O-(carbonyl-1-benzy-3H-imidazol-1-ium bromide) rifamycin S (XII, $X_3$ is morpholino) reacts with an oxazolidinone compound of formula 103 to give product of Formula XVI, wherein Ry and Rz are independently selected from H or F and Xg is $L_3$, $L_{11}$, or $L_{25}$. It will be apparent to one skilled in the art that the 25-O-(carbonyl-1-benzy-3H-imidazol-1-ium bromide) rifamycin S used herein can be replaced by other rifamycin analogs of Formula XII and the oxazolidinone compound 103 can be replaced by other pharmacophores within the oxazolidinone family. Specific variations to the oxazolidinone structure can be made to the C-5 position as indicated on structure 103. These variations have been described in detail by various authors and available in the public domain. The reaction is performed in an aprotic solvent catalyzed by an organic base. Examples of solvents suitable for this reaction are DCM, DCE, THF, DMSO, DMF, NMP, dioxane, acetonitrile or any combination of the above. Examples of bases are TEA, NMM, etc. Under certain circumstances, excess of 103 can be used as base.

Figure 8:
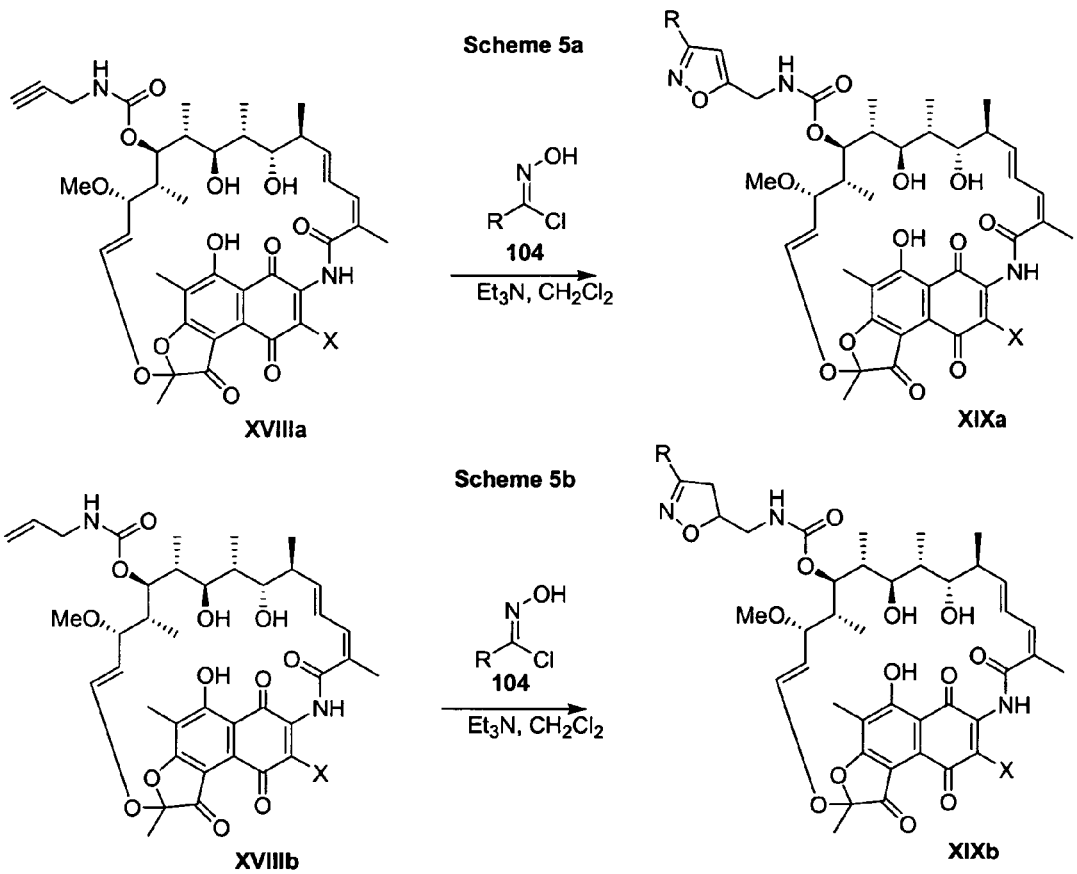
FIG. 8 shows Schemes 5a and 5b, wherein a rifamycin derivative with an isooxazole (5a) or dihydroisooxazole (5b) ring is constructed.

Scheme 5a, shown in FIG. 8, illustrates that compounds of Formula XIXa are prepared from 25-O-(prop-2-ynyl-carbamic acid) rifamycin S compounds such as XVIIIa through a 1,3-dipolar cycloaddition reaction. Scheme 5b, also shown in FIG. 8, illustrates that compounds of Formula XIXb are prepared from 25-O-(prop-2-enyl carbamic acid) rifamycin S compounds such as XVIIIb through a dipolar cycloaddition reaction.

Figure 9:
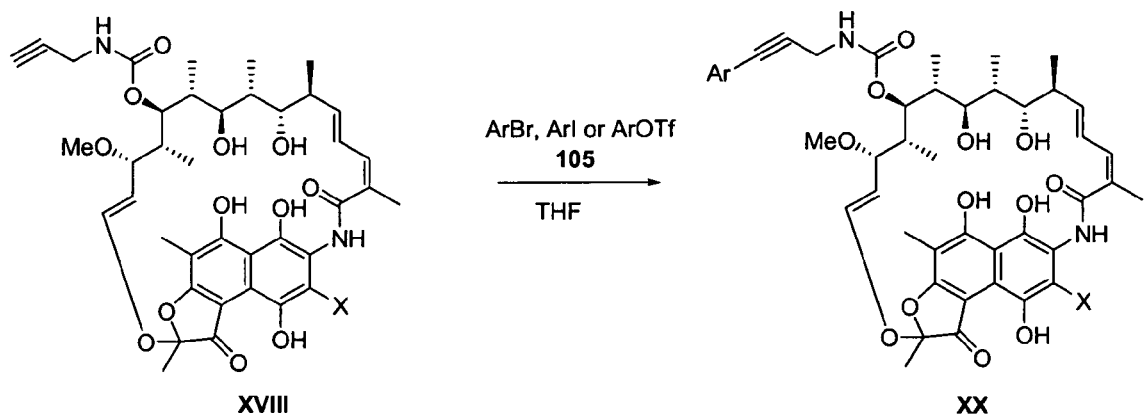
FIG. 9 shows Scheme 6, wherein a rifamycin derivative undergoes a palladium catalyzed arylation reaction.

One specific example for the synthesis of compounds XX is illustrated by Scheme 6, shown in FIG. 9, wherein 25-O-(prop-2-ynyl-carbamic acid) rifamycin S (XVIII) reacts with an aryl halide or triflate (105) to give products of Formula XX. The reaction is performed in an aprotic solvent with a palladium catalyst and a phosphine ligand. Examples of solvents suitable for this reaction are DME, THF, dioxane or any combination of the above. Examples of bases are $NaHCO_3$, $Na_2CO_3$, $KHCO_3$, $K_2CO_3$, $Cs_2CO_3$, etc. Palladium acetate, palladium tetra-kis-triphenyl phosphine, and various copper and nickel containing catalysts and a variety of other palladium catalysts can be used.

Figure 10:
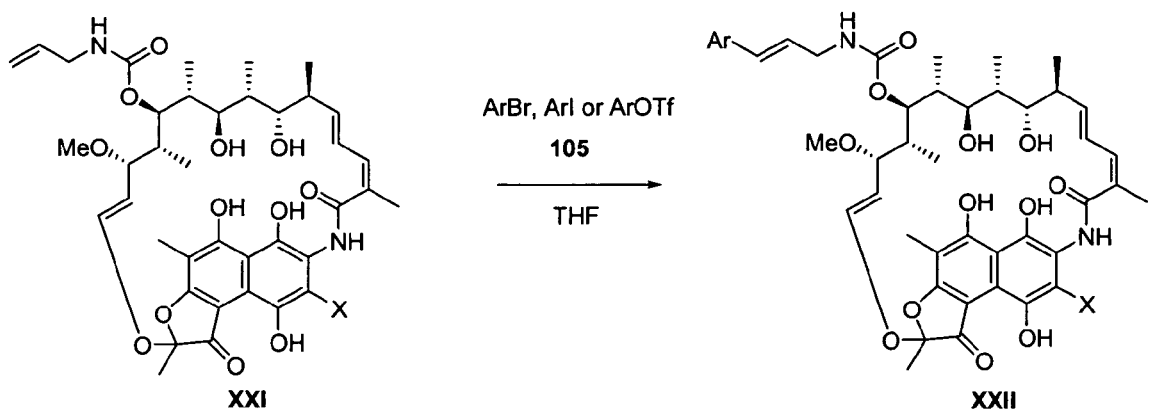
FIG. 10 shows Scheme 7, wherein a rifamycin derivative undergoes a palladium catalyzed arylation reaction.

Another specific example of compounds of Formula XXII is illustrated by Scheme 7, shown in FIG. 10, where 25-O-(prop-2-enyl-carbamic acid) rifamycin S (XXI) reacts with an aryl halide or triflate (105) in the prescence of palladium to give XXII. It will be apparent to one skilled in the art that compound 105 can be replaced by heterocyclic triflates or vinyl halides. Examples of solvents suitable for this reaction are DME, THF, dioxane or any combination of the above. Examples of bases are $NaHCO_3$, $Na_2CO_3$, $KHCO_3$, $K_2CO_3$, $Cs_2CO_3$, etc. Palladium acetate, palladium tetra-kis-triphenyl phosphine, nickel containing catalysts and a variety of other palladium catalysts can be used.

Figure 11:
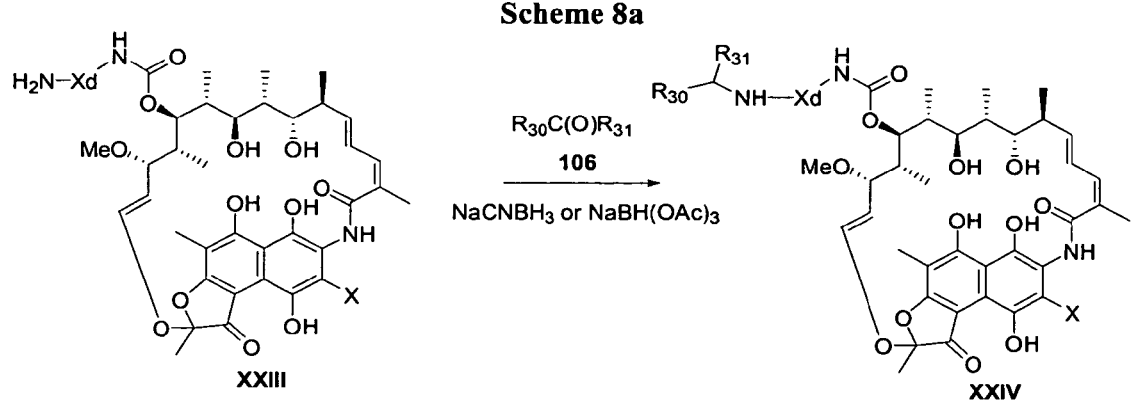
FIG. 11 shows Schemes 8a and 8b, wherein a rifamycin undergoes a reductive amination reaction.
Figure 11:
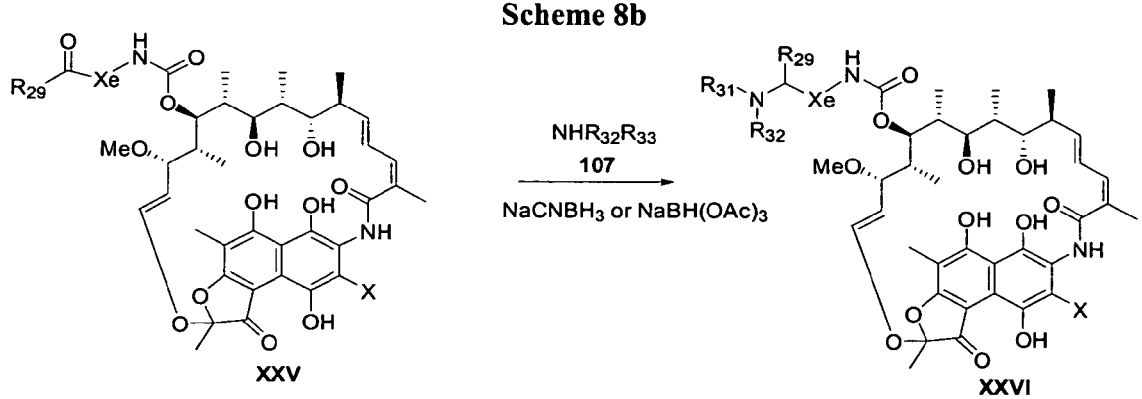

Yet another specific example of the current invention is illustrated by Scheme 8a, shown in FIG. 11, in which Formula XXIII reacts with an aldehyde or ketone (106) under reductive amination conditions to yield amine (XXIV). Compound 106 can be an aldehyde ($R_{31}$=H) or a ketone ($R_{31}$=alkyl) and Xd is defined by $L_{25}$ above. Alternatively in Scheme 8b, also shown in FIG. 11, a rifamycin compound of Formula XXV is treated with an amine 107 under reductive amination conditions to give a compound of Formula XXIV. $R_{29}$ can be a hydrogen or alkyl group. $R_{32}$ and $R_{33}$ can be selected from the groups defined by $R_2$ and $R_3$ above and Xe can be selected from $L_{25}$ defined above. The reaction is performed in a protic or aprotic solvent. Examples of solvents suitable for this reaction are THF, DMSO, DMF, NMP, ethanol, isopropanol, methanol, dioxane, acetonitrile, acetic acid, water or any combination of the above. Examples of reducing agents are sodium borohydride, sodium triacetoxyborohydride, sodium cyanoborohydride, and hydrogen in presence of a palladium catalyst.

Specific Compositions

The compounds of the current invention may be better understood with reference to the following specific examples, which are representative of some of the embodiments of the invention, and are not intended to limit the invention.

All starting material used in these examples are either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates (E. Merck) and spots are visualized with long-wave ultraviolet light followed by an appropriate staining reagent. Nuclear magnetic resonance ("NMR") spectra are recorded on a Varian 400 MHz magnetic resonance spectrometer. $^1$H NMR chemical shift are given in parts-per million ($\delta$) downfield from TMS using the residual solvent signal ($CHCl_3$=$\delta$ 7.27, $CH_3OH$=$\delta$ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electro spray ionization mass spectra are recorded on a Finnegan LCQ advantage spectrometer.

EXAMPLE 4

25-O-Desacetyl cyclic-21,23-(1-methylethylidene acetal) 3-morpholino-rifamycin S

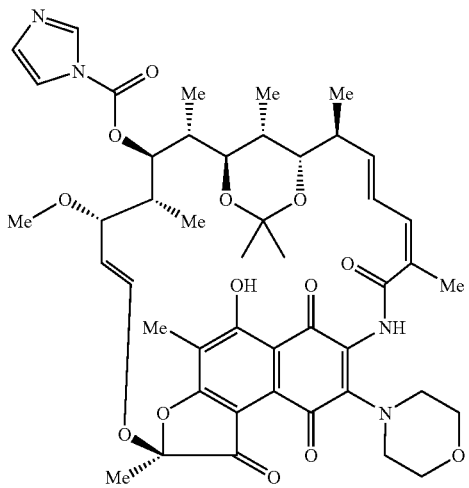

Synthesis: 25-O-desacetyl cyclic-21,23-(1-methylethylidene acetal)-3-morpholino-rifamycin S (5.0 grams, 6.4 mmol) was dissolved in anhydrous methylene chloride (400 ml) under a nitrogen atmosphere. To this solution was added 10 eq. (10.4 grams, 64 mmol) carbonyldiimidazole in 5 equal portions over the course of 5 days. After this time the solution was diluted with ethyl acetate (600 ml) and washed with 1 M aqueous citric acid (500 ml) which was followed by a wash with saturated sodium chloride (500 ml). The resulting solution was dried with sodium sulfate, filtered, and evaporated to produce the title compound as a dark solid (4.8 grams, 5.5 mmol, 86%) which was used without purification.

EXAMPLE 5

1-Benzyl-3-(25-O-desacetyl-(carbonyl-cyclic-21,23-(1-methylethylidene acetal) 3-morpholino rifamycin S))-3H-imidazol-1-ium

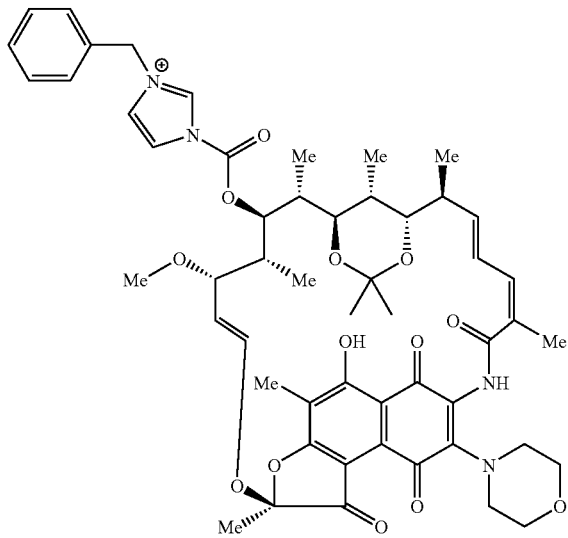

Synthesis: The compound of Example 4 (500 mg, 0.57 mmol) was dissolved in anhydrous acetonitrile under a nitrogen atmosphere. To this solution was added benzyl bromide (0.135 ml, 1.14 mmol). The resulting solution was allowed to stir at room temperature for 24 hours. After this time additional benzyl bromide was added (0.135 ml, 1.14 mmol) and the resulting solution was allowed to stir at room temperature for an additional 24 hours. The solution was diluted with diethyl ether (300 ml) and the resulting precipitate, the title compound (480 mg, 0.50 mmol, 87%), was collected by filtration and used without further purification.

EXAMPLE 6

25-O-Desacetyl-(1-carbonyl-4-methyl-piperazine) 3-morpholino rifamycin S

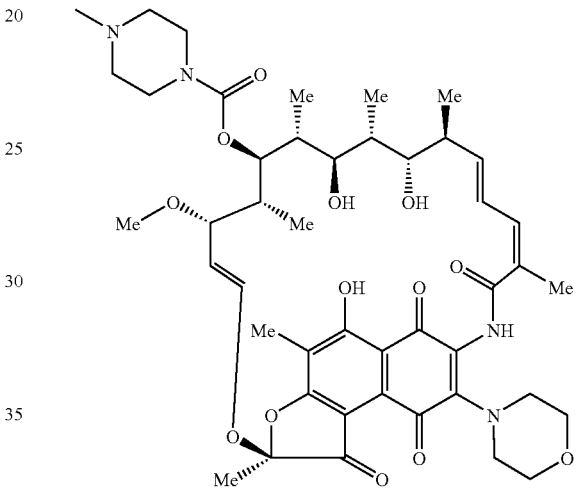

Synthesis: The compound of Example 5 (10 mg, 0.010 mmol) was dissolved in methylene chloride (1 ml) and treated with 1-methyl-piperazine (20 μL, 0.2 mmol). The resulting solution was stirred at room temperature for 30 minutes. The reaction mixture was diluted with ethyl acetate (3 ml) and washed with 1 M aqueous citric acid (3 ml) followed by washing with saturated sodium chloride (3 ml). The resulting solution was dried with sodium sulfate, filtered, and evaporated to produce a dark solid. This residue was taken up in 1:2 (V/V) 1 M aqueous HCl/tetrahydrofuran (1 ml) and stirred for 3 hours. After which time the mixture was diluted with ethyl acetate (3 ml) and the aqueous layer was removed. This solution was vigorously washed with an aqueous solution consisting of 5% (W/V) potassium ferricyanide and 5% (W/V) sodium bicarbonate, which was then followed by multiple washes with saturated sodium chloride. The resulting solution was dried with sodium sulfate, filtered, and evaporated to produce the title compound. ESI MS m/z (M+H)$^+$ 865, (M+H—OCH$_3$)$^+$ 833; $^1$H NMR (400 MHz, CDCl$_3$) δ 13.25 (s, 1H), 7.53 (s, 1H), 6.37 (d, J=10.9 Hz, 1H), 6.02 (dd, J=6.3 and 16.0 Hz, 1H), 6.06 (d, J=12.1 Hz, 1H), 5.05 (dd, J=5.1 and 12.5 Hz, 1H), 4.97 (d, J=9.8 Hz, 1H), 4.88-4.82 (m, 1H), 3.96-3.87 (m, 3H), 3.83-3.82 (m, 1H), 3.77-3.72 (m, 2H), 3.57-3.47 (m, 4H), 3.35-3.29 (m, 2H), 3.13-3.07 (m, 1H), 3.10 (s, 3H), 2.47-2.29 (m, 1H), 2.26 (s, 1H), δ 2.12 (s, 3H), 1.88-1.79 (m, 2H), 1.74 (s, 3H), 1.68-1.58 (m, 1H), 1.04 (d, J=7.0 Hz, 3H), 0.89 (d, J=7.0 Hz, 3H), 0.70 (d, J=6.6 Hz, 3H), 0.20 (d, J=7.0 Hz, 3H).

EXAMPLE 7

25-O-Desacetyl-(1-carbonyl-isobutylamino) 3-morpholino rifamycin S

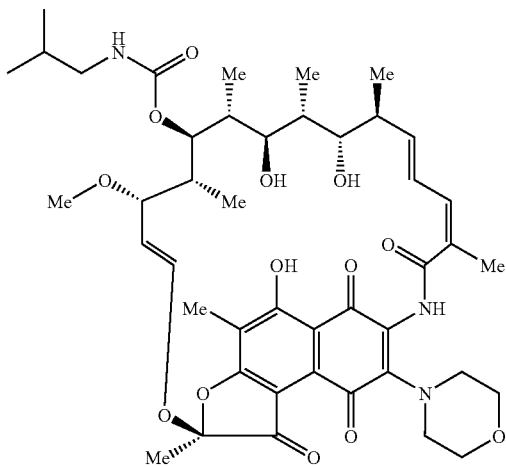

Synthesis: The title compound was prepared as described in Example 6 above, using isobutyl amine in place of 1-methyl-piperazine. ESI MS m/z (M+H)+ 838, (M+H—OCH3)+ 806; $^1$H NMR (400 MHz, CDCl$_3$) δ 13.25 (s, 1H), δ 7.52 (s, 1H), 6.39 (d, J=11.0 Hz, 1H), 6.21 (dd, J=6.6 and 16.4 Hz, 1H), 6.04 (d, J=12.5 Hz, 1H), 5.06 (dd, J=4.3 and 12.1 Hz, 1H), 4.94 (d, J=10.6 Hz, 1H), 4.84 (t, J=5.9 Hz, 1H), 3.99-3.94 (m, 2H), 3.92-3.87 (m, 2H), 3.77-3.72 (m, 2H), δ 3.57-3.52 (m, 2H), 3.54-3.29 (m, 2H), 3.17-3.14 (m, 1H), 3.12 (s, 3H), 2.99 (q, J=6.6 Hz, 1H), 2.35-2.32 (m, 3H), 2.26 (s, 3H), 2.12 (s, 3H), 2.04-1.98 (m, 1H), 1.87-1.78 (m, 2H), 1.74 (s, 3H), 1.04 (d, J=7.0 Hz, 3H), 0.90-0.85 (m, 9H), 0.69 (d, J=7.0 Hz, 3H), 0.18 (d, J=7.0 Hz, 3H).

EXAMPLE 8

25-O-Desacetyl-(carbonyl-allylamino) 3-morpholino rifamycin S

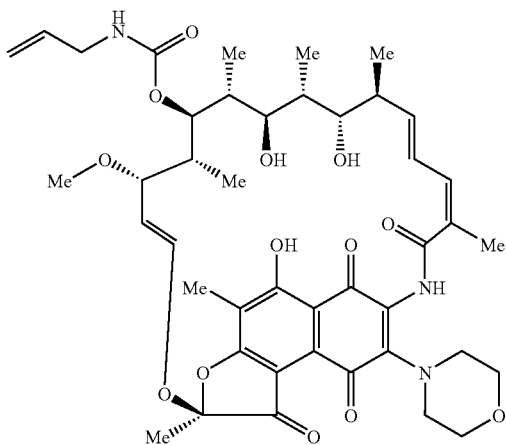

Synthesis: The title compound was prepared as described in Example 6 above, using allyl amine in place of 1-methyl-piperazine. ESI MS m/z (M+H)+ 822, (M+H—OCH$_3$)+ 790; $^1$H NMR (400 MHz, CDCl$_3$) δ 13.25 (s, 1H), 7.52 (s, 1H), 6.39 (d, J=10.6 Hz, 1H), 6.21 (dd, J=6.3 and 15.6 Hz, 1H), 6.03 (d, J=13.7 Hz, 1H), 5.86-5.76 (m, 2H), 5.19-5.12 (m, 1H), 5.06 (dd, J=4.3 and 12.1 Hz, 1H), 4.96 (d, J=9.8 Hz, 1H), 4.86 (t, J=6.2 Hz, 1H), 3.99-3.95 (m, 2H), 3.92-3.87 (m, 2H), 3.79-3.72 (m, 4H), 3.56-3.52 (m, 2H), 3.66-3.29 (m, 2H), 3.18-3.15 (m, 1H), 3.12 (s, 3H), 2.36-2.31 (m, 1H), 2.26 (s, 3H), 2.12 (s, 3H), 2.04-1.99 (m, 1H), 1.87-1.78 (m, 2H), 1.74 (s, 3H), 1.04 (d, J=7.0 Hz, 3H), 0.89 (d, J=7.0 Hz, 3H), 0.69 (d, J=6.6 Hz, 3H), δ 0.18 (d, J=7.0 Hz, 3H).

EXAMPLE 9

25-O-Desacetyl-(1-carbonyl-2-(4-methyl-piperazin-1-yl)-ethylamine) 3-morpholino rifamycin S

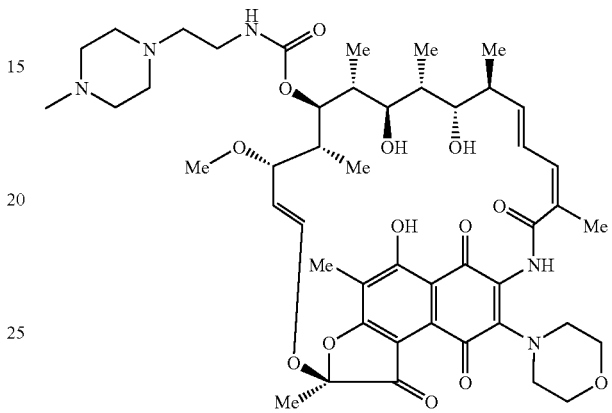

Synthesis: The title compound was prepared as described in Example 6 above, using 2-(4-methyl-piperazin-1-yl)-ethylamine in place of 1-methyl-piperazine. ESI MS m/z (M+H)+ 908; $^1$H NMR (400 MHz, CDCl$_3$) δ 13.25 (s, 1H), 7.53 (s, 1H), δ 3.38 (d, J=10.6 Hz, 1H), 6.20 (dd, J=6.3 and 16.0 Hz, 1H), 6.05 (d, J=12.1 Hz, 1H), 5.06 (dd, J=4.7 and 12.1 Hz, 1H), 4.92 (d, J=10.2 Hz, 1H), 3.97-3.86 (m, 5H), 3.77-3.72 (m, 2H), 3.57-3.52 (m, 3H), 3.34-3.24 (m, 4H), 3.18-3.15 (m, 1H), 3.10 (s, 3H), 2.59-2.42 (m, 8H), 2.37 (s, 3H), 2.25 (s, 3H), 2.12 (s, 3H), 1.86-1.79 (m, 3H), 1.74 (s, 3H), 1.68-1.56 (m, 1H), 1.04 (d, J=7.0 Hz, 3H), 0.89 (d, J=7.0 Hz, 3H), 0.69 (d, J=6.6 Hz, 3H), 0.18 (d, J=7.0 Hz, 3H).

EXAMPLE 10

25-O-Desacetyl-(1-carbonyl-2-diethylamine) 3-morpholino rifamycin S

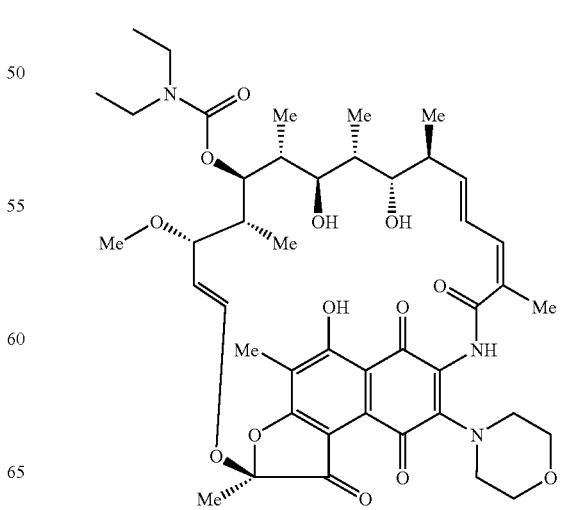

Synthesis: The title compound was prepared as described in Example 6 above, using diethylamine in place of 1-methyl-piperazine. ESI MS m/z (M+H)+ 838, (M+H—OCH₃)+ 806; ¹H NMR (400 MHz, CDCl₃) δ 13.25 (s, 1H), δ 7.51 (s, 1H), 6.41 (d, J=10.8 Hz, 1H), 6.23 (dd, J=6.3 and 15.6 Hz, 1H), 6.03 (d, J=14.0 Hz, 1H), 5.05 (dd, J=4.3 and 12.1 Hz, 1H), 5.01 (d, J=10.2 Hz, 1H), 3.99-3.97 (m, 1H), 3.92-3.87 (m, 2H), δ 3.77-3.72 (m, 2H), 3.56-3.52 (m, 3H), 3.39-3.26 (m, 4H), 3.19-3.14 (m, 2H), δ 3.10 (s, 3H), 2.37-2.31 (m, 1H), 2.25 (s, 3H), 2.12 (s, 3H), 1.91-1.79 (m, 2H), 1.75 (s, 3H), 1.70-1.59 (m, 1H), 1.09 (t, J=6.3 Hz, 6H), 1.04 (d, J=7.0 Hz, 3H), 0.89 (d, J=7.0 Hz, 3H), 0.72 (d, J=6.6 Hz, 3H), 0.21 (d, J=7.0 Hz, 3H).

EXAMPLE 11

25-O-Desacetyl-(1-carbonyl-3-imidazol-1-yl-propylamine) 3-morpholino rifamycin S

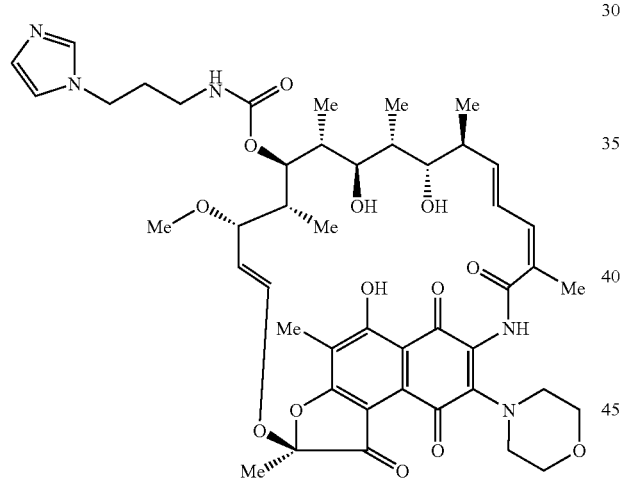

Synthesis: The title compound was prepared as described in Example 6 above, using 3-imidazol-1-yl-propylamine in place of 1-methyl-piperazine. ESI MS m/z (M+H)+ 890; ¹H NMR (400 MHz, CDCl₃) δ 13.25 (s, 1H), δ 7.72-7.70 (m, 1H), δ 7.56-7.52 (m, 1H), 7.48 (s, 1H), 7.06 (s, 1H), 6.36 (d, J=10.9 Hz, 1H), 6.17 (dd, J=6.6 and 16.0 Hz, 1H), 6.04 (d, J=12.1 Hz, 1H), 5.06 (dd, J=5.0 and 12.1 Hz, 1H), 4.96-4.90 (m, 2H), 4.01-3.88 (m, 5H), 3.78-3.70 (m, 3H), 3.57-3.50 (m, 2H), 3.34-3.29 (m, 2H), 3.21-3.09 (m, 3H), 3.11 (s, 3H), 2.42-2.30 (m, 1H), 2.27 (s, 3H), 2.01-1.94 (m, 2H), 1.85-1.79 (m, 1H), 1.74 (s, 3H), 1.04 (d, J=7.0 Hz, 3H), 0.94-0.83 (m, 5H), 0.68 (d, J=6.6 Hz, 3H), 0.19 (d, J=6.6 Hz, 3H).

EXAMPLE 12

25-O-Desacetyl-(1-carbonyl-1-(4-fluorophenyl)-piperazine) 3-morpholino rifamycin S

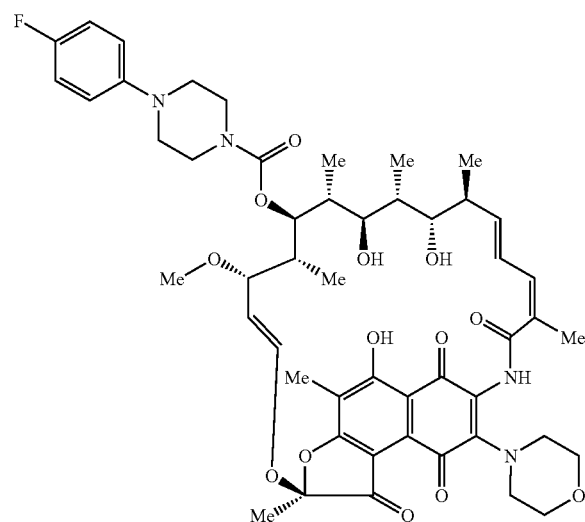

Synthesis: The title compound was prepared as described in Example 6 above, using 4-(fluorophenyl)-piperazine in place of 1-methyl-piperazine. ESI MS m/z (M+H)+ 945, (M+H—OCH³)+ 913; ¹H NMR (400 MHz, CDCl₃) δ 13.25 (s, 1H), 7.52 (s, 1H), 7.22-7.14 (m, 1H), 7.01-6.85 (m, 5H), δ 6.36 (d, J=10.7 Hz, 1H), 6.19-6.13 (m, 1H), 6.04 (d, J=14.4 Hz, 1H), 5.08-5.03 (m, 1H), 4.99-4.97 (d, J=9.8 Hz, 1H), 4.84-4.76 (m, 1H), δ 3.96-3.87 (m, 1H), δ 3.78-3.70 (m, 2H), 3.66-3.59 (m, 3H), 3.56-3.47 (m, 3H), 3.33-3.27 (m, 2H), 3.10 (s, 3H), 3.10-2.94 (m, 2H), 2.40-2.30 (m, 1H), 2.24 (s, 3H), 2.10 (s, 3H), 1.89-1.77 (m, 3H), 1.73 (s, 3H), 1.05-1.02 (m, 3H), 0.88-0.85 (m, 3H), 0.72-0.69 (m, 3H), 0.21-0.18 (m, 3H).

EXAMPLE 13

25-O-Desacetyl-(carbonyl-1-(3-trifluoromethylbenzylamino)) 3-morpholino rifamycin S

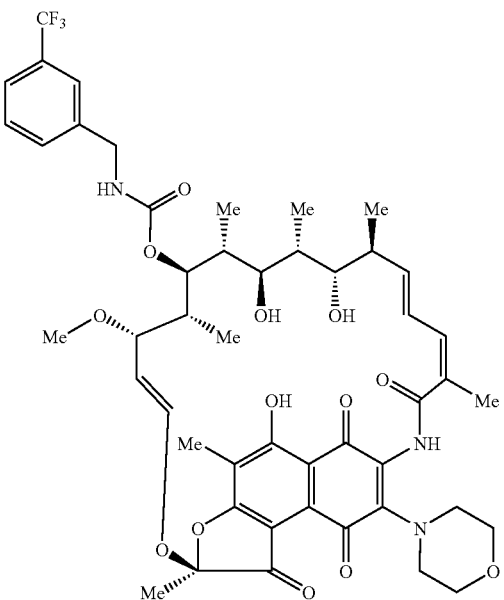

Synthesis: The title compound was prepared as described in Example 6 above, using 3-(trifluoromethylphenyl)-piperazine in place of 1-methyl-piperazine. ESI MS m/z (M+H)⁺ 940, (M+H—OCH₃)⁺ 908; ¹H NMR (400 MHz, CDCl₃) δ 13.25 (s, 1H), 7.52-7.50 (m, 3H), 7.45-7.44 (m, 2H), 6.39 (d, J=10.9 Hz, 1H), 6.19 (dd, J=6.3 and 15.6 Hz, 1H), 6.03 (d, J=12.1 Hz, 1H), 5.25 (t, J=6.0 Hz, 1H), 5.04 (dd, J=4.7 and 12.1 Hz, 1H), 4.98 (d, J=9.4 Hz, 1H), 4.48-4.33 (m, 2H), 3.39-3.87 (m, 3H), 3.76-3.71 (m, 2H), 3.57-3.49 (m, 3H), 3.34-3.29 (m, 2H), 3.16-3.13 (m, 1H), 3.03 (s, 3H), 2.38-2.31 (m, 1H), 2.25 (s, 3H), 2.12 (s, 3H), 1.88-1.79 (m, 3H), 1.74 (s, 3H), 1.04 (d, J=7.0 Hz, 3H), 0.89 (d, J=7.0 Hz, 3H), 0.69 (d, J=6.6 Hz, 3H), 0.18 (d, J=7.4 Hz, 3H).

EXAMPLE 14

25-O-Desacetyl-(carbonyl-1-pyrrolidino) 3-morpholino rifamycin S

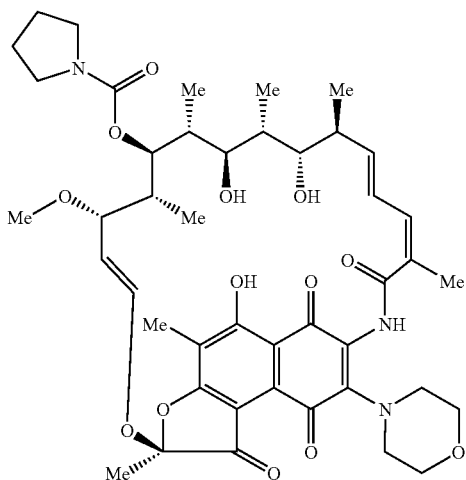

Synthesis: The title compound was prepared as described in Example 6 above, using pyrrolidine in place of 1-methyl-piperazine. ESI MS m/z (M+H)⁺ 836, (M+H—OCH₃)⁺ 804; ¹H NMR (400 MHz, CDCl₃) δ 13.25 (s, 1H), 7.52 (s, 1H), 6.39 (d, J=10.9 Hz, 1H), 6.22 (dd, J=6.6 and 15.6 Hz, 1H), 6.03 (d, J=12.1 Hz, 1H), 5.05 (dd, J=4.3 and 12.1 Hz, 1H), 4.97 (d, J=9.4 Hz, 1H), 3.98-3.96 (m, 2H), 3.92-3.87 (m, 2H), 3.77-3.72 (m, 2H), 3.57-3.51 (m, 4H), 3.40-3.27 (m, 6H), 3.16-3.14 (m, 1H), 3.10 (s, 3H), 2.36-2.31 (m, 1H), 2.26 (s, 3H), 2.12 (s, 3H), 1.91-1.78 (m, 3H), 1.74 (s, 3H), δ 1.27-1.24 (m, 4H), 1.04 (d, J=7.0 Hz, 3H), 0.89 (d, J=7.0 Hz, 3H), 0.71 (d, J=7.0 Hz, 3H), 0.18 (d, J=7.0 Hz, 3H).

EXAMPLE 15

25-O-Desacetyl (carbonyl-benzyl) 3-morpholino rifamycin S

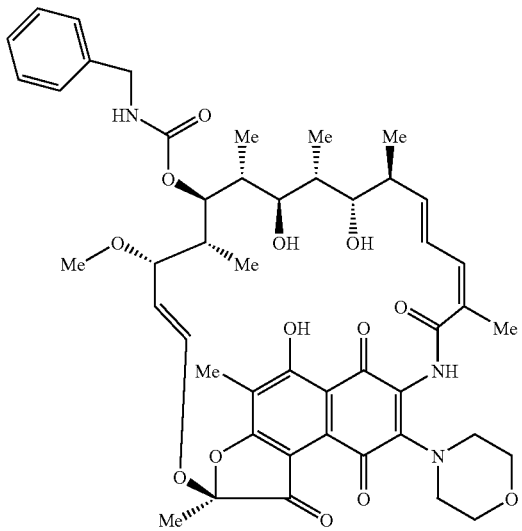

Synthesis: The title compound was prepared as described in Example 6 above, using benzylamine in place of 1-methyl-piperazine. ESI MS m/z (M+H)⁺ 872, (M+H—OCH₃)⁺ 840; ¹H NMR (400 MHz, CDCl₃) δ 13.25 (s, 1H), δ 7.52 (s, 1H), δ 7.33-7.23 (m, 5H), δ 6.39 (d, J=10.6 Hz, 1H), δ 6.21 (dd, J=5.5 and 14.8 Hz, 1H), δ 6.02 (d, J=12.1 Hz, 1H), δ 5.13 (t, J=5.8 Hz, 1H), δ 5.04 (dd, J=3.9 and 11.7 Hz, 1H), δ 4.98 (d, J=10.2 Hz, 1H), δ 4.33 (d, J=6.3 Hz, 2H), δ 3.99-3.87 (m, 3H), δ 3.76-3.71 (m, 2H), δ 3.56-3.47 (m, 3H), δ 3.34-3.28 (m, 2H), δ 3.18-3.16 (m, 1H), δ 3.05 (s, 3H), δ 2.36-2.31 (m, 1H), δ 2.26 (s, 3H), δ 2.12 (s, 3H), δ 1.88-1.80 (m, 1H), δ 1.73 (s, 3H), δ 1.04 (d, J=6.3 Hz, 3H), δ 0.89 (d, J=7.0 Hz, 3H), δ 0.68 (d, J=7.0 Hz, 3H), δ 0.18 (d, J=7.0 Hz, 3H).

EXAMPLE 16

25-O-Desacetyl-(4-carbonyl-1-cyclopropyl-6-fluoro-4-oxo-7-piperazin-1-yl-1,4-dihydro-quinoline-3-carboxylic acid) 3-morpholino rifamycin S

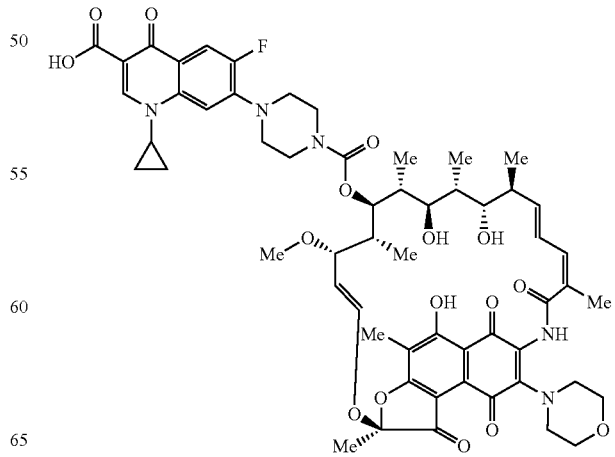

Synthesis: 1-Benzyl-3-(25-O-carbonyl-3-morpholino rifamycin S cyclic-21,23-(1-methylethylidene acetal))-3H-imidazol-1-ium, (10 mg, 0.010 mmol) was dissolved in methylene chloride (1 ml). To this was added 1-cyclopropyl-6-fluoro-4-oxo-7-piperazin-1-yl-1,4-dihydro-quinoline-3-carboxylic acid (10 mg, 0.030 mmol) and N-methylmorpholine (6 ul, 0.050 mmol). The resulting solution was stirred at room temperature for 30 minutes. The reaction mixture was diluted with ethyl acetate (3 ml) and washed with 1 M aqueous citric acid (3 ml) followed by washing with brine (3 ml). The resulting solution was dried with sodium sulfate, filtered, and evaporated to produce a dark solid. This residue was taken up in 1:2 (V/V) 1 M aqueous HCl/tetrahydrofuran (1 ml) and stirred for 3 hours. After which time the mixture was diluted with ethyl acetate (3 ml) and the aqueous layer was removed. This solution was vigorously washed with an aqueous solution consisting of 5% (W/V) potassium ferricyanide and 5% (W/V) sodium bicarbonate, which was then followed by multiple washes with brine. The resulting solution was dried with sodium sulfate, filtered, and evaporated. The residue was purified by silica gel column chromatography (step gradient; (99.9% EtOAc/0.01% HOAc) to (89.9% EtOAc/10% MeOH/0.01% HOAc) to (49.9% EtOAc/50% MeOH/0.01% HOAc) to produce the title compound. ESI MS m/z (M+H)$^+$ 1096; $^1$H NMR (400 MHz, CDCl$_3$) δ 13.25 (s, 1H), 8.79 (s, 1H), 8.06 (d, J=12.5 Hz, 1H), 7.56 (s, 1H), 6.36 (d, J=10.6 Hz, 1H), 6.16 (dd, J=6.6 and 16.4 Hz, 1H), 6.07 (d, J=10.9 Hz, 1H), 5.09 (dd, J=5.1 and 13.7 Hz, 1H), 5.02 (d, J=10.2 Hz, 1H), 3.95-3.87 (m, 3H), 3.77-3.62 (m, 4H), 3.58-3.50 (m, 3H), 3.35-3.22 (m, 5H), 3.12 (s, 3H), 2.38-2.33 (m, 1H), 2.27 (s, 3H), 2.14-2.12 (m, 2H), 2.09 (s, 3H), 1.88-1.79 (m, 1H), 1.74 (s, 3H), 1.05 (d, J=7.0 Hz, 3H), 0.89-0.78 (m, 7H), 0.72 (d, J=6.6 Hz, 3H), 0.24 (d, J=7.0 Hz, 3H).

EXAMPLE 17

25-O-Desacetyl-(8-chloro-1-cyclopropyl-7-[4-(1-carbonyl)-piperazin-1-yl]-6-fluoro-4-oxo-1,4-dihydro-quinoline-3-carboxylic acid) 3-morpholino rifamycin S

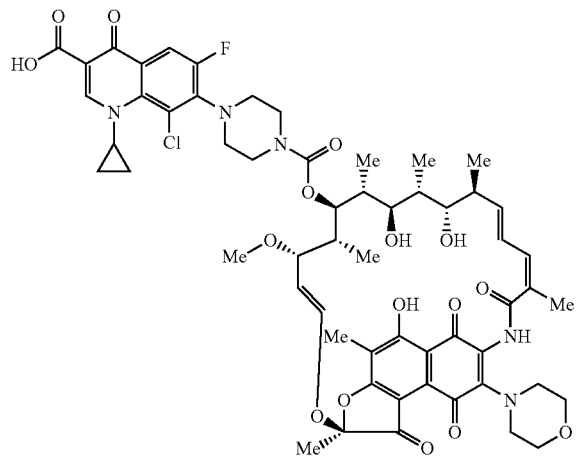

Synthesis: The title compound was prepared as described in Example 16 above, using 8-chloro-1-cyclopropyl-6-fluoro-4-oxo-7-piperazin-1-yl-1,4-dihydro-quinoline-3-carboxylic acid in place of 1-cyclopropyl-6-fluoro-4-oxo-7-piperazin-1-yl-1,4-dihydro-quinoline-3-carboxylic acid. ESI MS m/z (M+H)$^+$ 1130, (M+H—OCH$_3$)$^+$ 1098; $^1$H NMR (400 MHz, CDCl$_3$) δ 13.25 (s, 1H), 8.88 (s, 1H), 7.96 (d, J=12.9 Hz, 1H), 7.53 (s, 1H), 7.22-7.16 (m, 1H), 6.37 (d, J=10.9 Hz, 1H), 6.22-6.13 (m, 1H), 6.04 (dd, J=11.5 and 22.0 Hz, 1H), 5.18 (t, J=6.8 Hz, 1H), 5.11-5.02 (m, 1H), δ 4.97-4.93 (m, 1H), 4.40-4.25 (m, 2H), 3.96-3.85 (m, 3H), 3.84-3.71 (m, 3H), 3.66-3.62 (m, 1H), 3.57-3.43 (m, 3H), 3.34-3.29 (m, 2H), 3.15 (s, 1.5H), 63.04 (s, 1.5H), 2.38-2.31 (m, 1H), 2.26 (s, 1.5H), 2.25 (s, 1.5H), 2.12 (s, 1.5H), 2.01-1.92 (m, 1H), 1.84-1.79 (m, 1H), 1.75 (s, 1.5H), 1.73 (s, 1.5H), 1.68-1.61 (m, 1H), 1.82-1.23 (m, 5H), 1.06-0.87 (m, 5H), 0.71-0.67 (m, 3H), 0.20-0.17 (m, 3H).

EXAMPLE 18

25-O-Desacetyl-(1-carbonyl-(2-pyridin-2-yl-ethylamine)) 3-morpholino rifamycin S

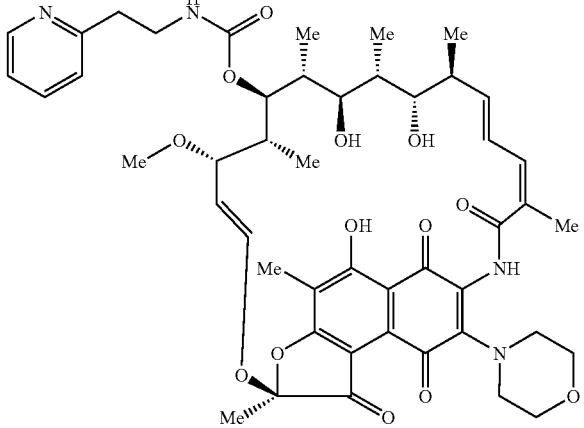

Synthesis: The title compound was prepared as described in Example 6 above, using 2-pyridin-2-yl-ethylamine in place of 1-methyl-piperazine. ESI MS m/z (M+H)$^+$ 887, (M+H—OCH$^3$)$^+$ 885; $^1$H NMR (400 MHz, CDCl$_3$) δ 13.25 (s, 1H), 8.52 (d, J=6.3 Hz, 1H), 7.61 (t, J=7.4 Hz, 1H), 7.51 (s, 1H), 7.17-7.13 (m, 2H), 6.39 (d, J=11.3 Hz, 1H), 6.21 (dd, J=6.6 and 16.0 Hz, 1H), 6.00 (d, J=12.5 Hz, 1H), 5.59 (t, J=5.6 Hz, 1H), 5.02 (dd, J=4.7 and 12.5 Hz, 1H), 4.90-4.89 m, 1H), 3.97-3.87 (m, 3H), 3.76-3.72 (m, 2H), 3.61-3.49 (m, 3H), 3.33-3.29 (m, 2H), 3.15-3.12 (m, 1H), δ 3.04 (s, 3H), 0.89 (d, J=7.0 Hz, 3H), 3.00-2.95 (m, 2H), 2.37-2.31 (m, 1H), 2.25 (s, 3H), 2.12 (s, 3H), 2.1-1.99 (m, 1H), 1.86-1.81 (m, 1H), 1.74 (s, 3H), 1.04 (d, J=7.0 Hz, 3H), 0.89 (d, J=7.0 Hz, 3H), 0.66 (d, J=6.6 Hz, 3H), 0.89 (d, J=7.0 Hz, 3H).

EXAMPLE 19

25-O-Desacetyl-(1-carbonyl-2-thiophen-2-yl-ethylamine) 3-morpholino rifamycin S

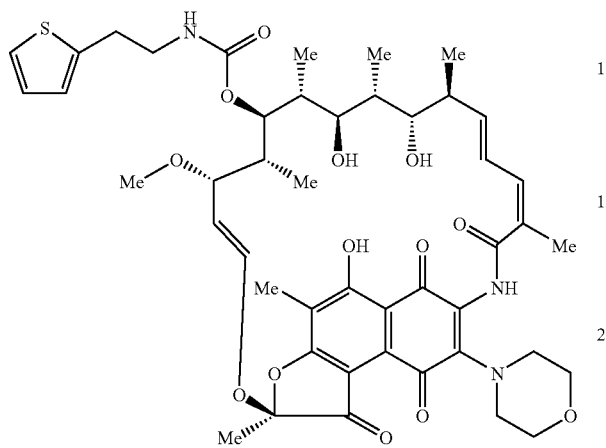

Synthesis: The title compound was prepared as described in Example 6 above, using 2-pyridin-2-yl-ethylamine in place of 1-methyl-piperazine. ESI MS m/z (M+H)+ 892, (M+H—OCH³)+ 860; ¹H NMR (400 MHz, CDCl₃) δ 13.25 (s, 1H), 7.52 (s, 1H), 7.15 (d, J=5.9 Hz, 1H), 6.96-6.92 (m, 1H), 6.80 (d, J=3.1 Hz, 1H), 6.39 (d, J=11.0 Hz, 1H), 6.24-6.18 (m, 1H), 6.03 (d, J=12.1 Hz, 1H), 5.04 (dd, J=4.7 and 12.5 Hz, 1H), 3.97-3.85 (m, 3H), 3.76-3.71 (m, 3H), 3.56-3.52 (m, 2H), 3.48-3.39 (d, J=7.0 Hz, 2H), 3.34-3.29 (m, 1H), 3.17-3.13 (m, 1H), 3.11 (s, 3H), 3.08-2.97 (m, 4H), 2.40-2.30 (m, 1H), 2.26 (s, 3H), 2.17-2.15 (m, 1H), 2.12 (s, 3H), 2.04-2.00 (m, 1H), 1.85-1.79 (m, 1H), 1.75 (s, 3H), 1.05 (d, J=6.6 Hz, 3H), 0.89 (d, J=6.6 Hz, 3H), 0.67 (d, J=6.6 Hz, 3H), δ 0.18 (d, J=7.0 Hz, 3H).

EXAMPLE 20

25-O-Desacetyl-(1-carbonyl-2-aminoethanol) 3-morpholino rifamycin S

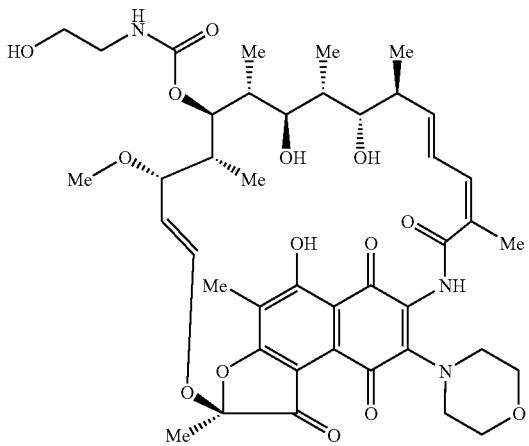

Synthesis: The title compound was prepared as described in Example 6 above, using 2-ethanolamine in place of 1-methyl-piperazine. ESI MS m/z (M+H)+ 826, (M+H—OCH³)+ 794; ¹H NMR (400 MHz, CDCl₃) δ 13.25 (s, 1H), 7.52 (s, 1H), 3.39 (d, J=10.6 Hz, 1H), 6.19 (dd, J=6.6 and 14.9 Hz, 1H), 6.03 (d, J=12.5 Hz, 2H), 5.23 (m, 1H), 5.06 (dd, J=4.7 and 12.1 Hz, 1H), 4.95 (d, J=10.6 Hz, 1H), 4.69 (m, 1H), 3.97-3.87 (m, 3H), 3.77-3.69 (m, 5H), 3.56-3.52 (m, 2H), 3.36-3.25 (m, 2H), 3.20-3.15 (m, 1H), δ 3.13 (s, 3H), 2.37-2.30 (m, 1H), 2.26 (s, 3H), 2.12 (s, 3H), 2.01-1.92 (m, 1H), 1.85-1.79 (m, 2H), 174 (s, 3H), 1.03 (d, J=7.0 Hz, 3H), 0.89 (d, J=7.0 Hz, 3H), 0.69 (d, J=6.6 Hz, 3H), 0.18 (d, J=7.0 Hz, 3H).

EXAMPLE 21

25-O-Desacetyl-(carbonyl-methylamino) 3-morpholino rifamycin S

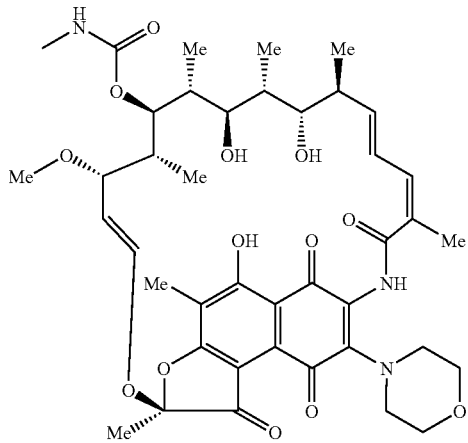

Synthesis: The title compound was prepared as described in Example 6 above, using methylamine in place of 1-methyl-piperazine. ESI MS m/z (M+H)+ 796, (M+H—OCH₃)+ 764; ¹H NMR (400 MHz, CDCl₃) δ 13.25 (s, 1H), 7.16 (s, 1H), 6.40 (d, J=11.0 Hz, 1H), 6.21 (dd, J=7.0 and 16.4 Hz, 1H), 6.04 (d, J=12.1 Hz, 1H), 5.05 (dd, J=5.7 and 13.3 Hz, 1H), 4.95 (d, J=9.8 Hz, 1H), 3.98-3.87 (m, 3H), 3.76-3.71 (m, 3H), 3.56-3.51 (m, 2H), 3.34-3.29 (m, 2H), 3.18-3.15 (m, 1H), 3.11 (s, 3H), 2.79-2.78 (d, J=4.7 Hz, 3H), 2.38-2.32 (m, 3H), 2.26 (s, 3H), 2.18-2.14 (m, 1H), 2.12 (s, 3H), 2.04-1.97 (m, 1H), 1.86-1.78 (m, 1H), 1.74 (s, 3H), 1.04 (d, J=7.0 Hz, 3H), 0.89 (d, J=7.0 Hz, 3H), 0.68 (d, J=7.0 Hz, 3H), 0.18 (d, J=7.0 Hz, 3H).

EXAMPLE 22

25-O-Desacetyl-(carbonyl-4-chlorobenzyl) 3-morpholino rifamycin S

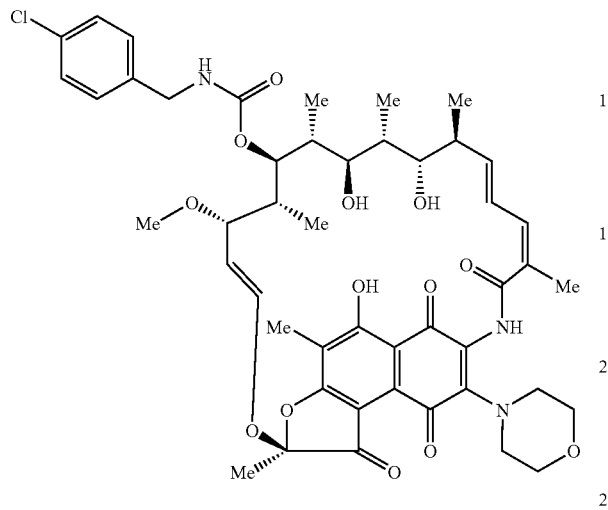

Synthesis: The title compound was prepared as described in Example 6 above, using 4-chlorobenzylamine in place of 1-methyl-piperazine. ¹H NMR (400 MHz, CDCl₃) δ 7.53 (s, 1H), δ 7.38-7.17 (m, 5H), 6.38 (d, J=10.6 Hz, 1H), 6.28-6.17 (m, 1H), 6.03 (d, J=12.1 Hz, 1H), δ 5.17-5.14 (m, 1H), 5.04 (dd, J=4.3 and 12.1 Hz, 1H), 4.96 (d, J=10.1 Hz, 1H), 4.29 (d, J=6.3 Hz, 2H), 3.96-3.70 (m, 4H), 3.57-3.28 (m, 4H), 3.23-3.11 (m, 2H), 3.04-3.01 (m, 4H), 2.44-2.30 (m, 1H), 2.25 (s, 3H), 2.18-2.15 (m, 2H), 2.12 (s, 3H), 2.02-2.00 (m, 1H), 1.74 (s, 3H), 1.03 (d, J=5.8 Hz, 3H), 0.89 (d, J=6.3 Hz, 3H), 0.67 (d, J=5.5 Hz, 3H), 0.18 (d, J=6.6 Hz, 3H); ESI MS m/z 906.0 (M+H)⁺.

EXAMPLE 23

25-O-Desacetyl-(carbonyl-naphthalen-1-ylmethyl-amino) 3-morpholino rifamycin S

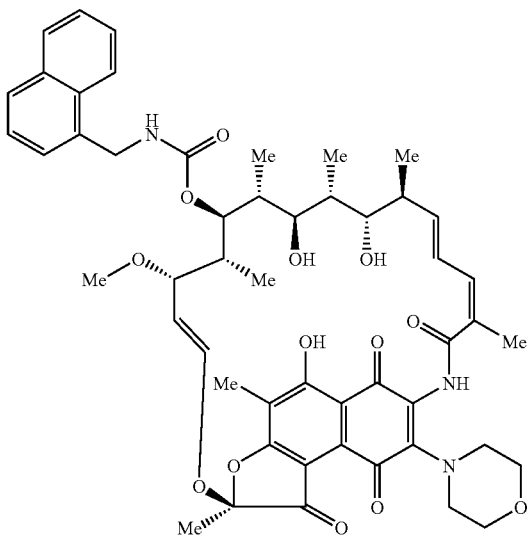

Synthesis: The title compound was prepared as described in Example 6 above, using naphthyl-1-yl methyl in place of 1-methyl-piperazine. ESI MS m/z (M+H)⁺ 922, (M+H—OCH³)⁺ 890; ¹H NMR (400 MHz, CDCl₃) δ 13.25 (s, 1H), 8.00-7.98 (m, 1H), 7.90-7.80 (m, 2H), 7.56-7.50 (m, 2H), 7.46-7.40 (m, 2H), 6.39 (d, J=11.3 Hz, 1H), 6.27-6.18 (m, 1H), 6.01 (d, J=11.0 Hz, 1H), 5.26-5.17 (m, 1H), 5.11-5.08 (m, 1H), 5.03-4.89 (m, 1H), 4.85-4.80 (m, 2H), 3.97-3.86 (m, 3H), 3.77-3.72 (m, 3H), 3.56-3.48 (m, 2H), 3.40-3.28 (m, 2H), 3.25-3.17 (m, 1H), 3.05 (s, 3H), 2.40-2.30 (m, 1H), 2.26 (s, 3H), 2.12 (s, 3H), 2.09-2.02 (m, 1H), 1.88-1.84 (m, 2H), 1.73 (s, 3H), 1.06 (d, J=6.6 Hz, 3H), 0.88 (d, J=6.3 Hz, 3H), 0.64 (d, J=6.6 Hz, 3H), 0.17 (d, J=6.6 Hz, 3H).

EXAMPLE 24

25-O-Desacetyl-(carbonyl-3-phenylpropylamino) 3-morpholino rifamycin S

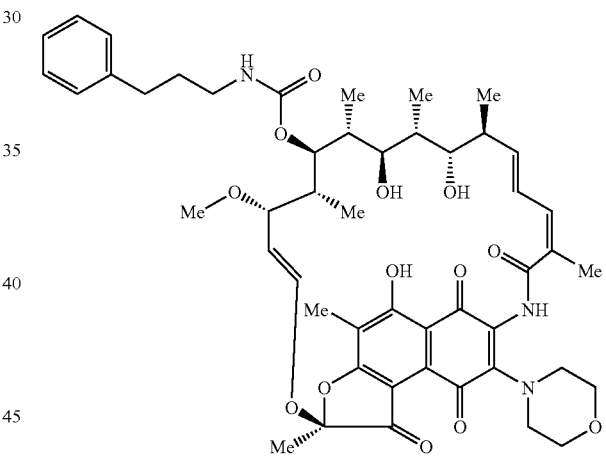

Synthesis: The title compound was prepared as described in Example 6 above, using 3-phenyl-propylamine in place of 1-methyl-piperazine. ESI MS m/z (M+H)⁺ 900, (M+H—OCH³)⁺ 878; ¹H NMR (400 MHz, CDCl₃) δ 13.25 (s, 1H), δ 7.52 (s, 1H), δ 7.33-7.27 (m, 2H), δ 7.20-7.13 (m, 3H), δ 6.39 (d, J=10.2 Hz, 1H), δ 6.20 (dd, J=7.4 and 15.0 Hz, 1H), δ 6.04 (d, J=11.7 Hz, 1H), δ 5.05 (d, J=14.1 Hz, 1H), δ 4.93 (d, J=9.0 Hz, 1H), δ 4.82-4.78 (m, 2H), δ 3.97-3.86 (m, 3H), δ 3.78-3.70 (m, 3H), δ 3.57-3.50 (m, 2H), δ 3.40-3.28 (m, 2H), δ 3.21-3.16 (m, 1H), δ 3.11 (s, 3H), δ 2.67-2.59 (m, 2H), δ 2.37-2.29 (m, 1H), δ 2.25 (s, 3H), δ 2.11 (s, 3H), δ 2.08-2.05 (m, 3H), δ 1.73 (s, 3H), δ 1.03 (d, J=5.8 Hz, 3H), δ 0.89 (d, J=6.3 Hz, 3H), δ 0.67 (d, J=5.5 Hz, 3H), δ 0.18 (d, J=6.6 Hz, 3H).

EXAMPLE 25

25-O-Desacetyl-(carbonyl-3-phenylethylamino) 3-morpholino rifamycin S

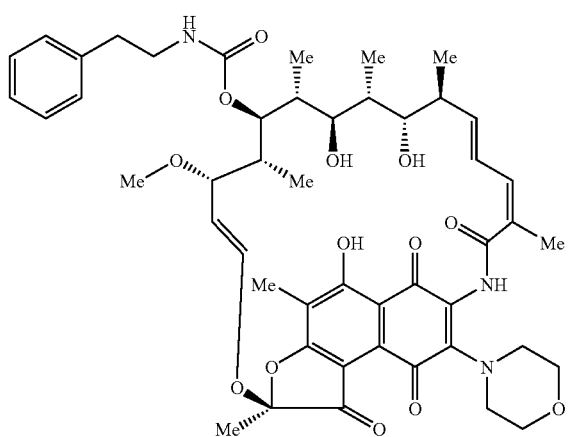

Synthesis: The title compound was prepared as described in Example 6 above, using 3-phenethylamine in place of 1-methyl-piperazine. ESI MS m/z (M+H)⁺ 886, (M+H—OCH³)⁺ 854; $^1$H NMR (400 MHz, CDCl$_3$) δ 13.25 (s, 1H), δ 7.53 (s, 1H), 7.31-7.26 (m, 2H), 7.23-7.22 (d, J=8.2 Hz, 1H), 7.15 (d, J=7.4 Hz, 2H), 6.39 (d, J=10.5 Hz, 1H), 6.21 (dd, J=6.3 and 16.0 Hz, 1H), 6.02 (d, J=12.1 Hz, 1H), 5.02 (dd, J=4.7 and 12.5 Hz, 1H), 4.92 (d, J=9.8 Hz, 1H), 4.08-4.77 (m, 2H), 3.97-3.87 (m, 3H), 3.78-3.71 (m, 3H), 3.56-3.51 (m, 2H), 3.48-3.41 (m, 2H), 3.14-3.11 (m, 1H), 3.07 (s, 3H), 2.82-2.74 (m, 2H), 2.38-2.29 (m, 1H), 2.25 (s, 3H), 2.12 (s, 3H), 1.86-1.79 (m, 2H), 1.74 (s, 3H), 1.57-1.52 (m, 1H), 1.05 (d, J=7.0 Hz, 3H), 0.89 (d, J=7.0 Hz, 3H), 0.65 (d, J=6.6 Hz, 3H), 0.17 (d, J=7.0 Hz, 3H).

EXAMPLE 26

25-O-Desacetyl-(carbonyl-4-methoxybenzylamino) 3-morpholino rifamycin S

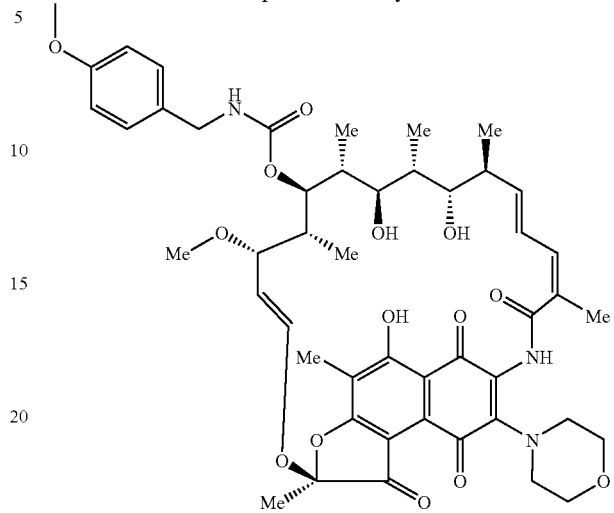

Synthesis: The title compound was prepared as described in Example 6 above, using 4-methoxybenzylamine in place of 1-methyl-piperazine. ESI MS m/z (M+H)⁺ 902, (M+H—OCH³)⁺ 870; $^1$H NMR (400 MHz, CDCl$_3$) δ 13.25 (s, 1H), 7.53 (s, 1H), 7.17 (d, J=8.6 Hz, 2H), 6.83 (d, J=8.6 Hz, 2H), 6.39 (d, J=10.6 Hz, 1H), 6.21 (dd, J=6.3 and 15.6 Hz, 1H), 6.03 (d, J=12.1 Hz, 1H), 5.09-5.02 (m, 1H), 4.97 (d, J=9.8 Hz, 1H), 4.26 (d, J=5.9 Hz, 1H), 4.00-3.87 (m, 3H), 3.82-3.71 (m, 3H), 3.78 (s, 3H), 3.56-3.51 (m, 2H), 3.34-3.29 (m, 2H), 3.17-3.10 (m, 2H), 3.05 (s, 3H), 2.43-2.30 (m, 1H), 2.26 (s, 3H), 2.23-2.71 (m, 2H), 2.12 (s, 3H), 1.85-1.80 (m, 3H), 1.73 (s, 3H), 1.62-1.56 (m, 1H), 1.04 (d, J=6.6 Hz, 3H), 0.89 (d, J=7.0 Hz, 3H), 0.67 (d, J=6.6 Hz, 3H), 0.18 (d, J=7.0 Hz, 3H).

EXAMPLE 27

25-O-Desacetyl-((2-Amino-ethyl)-carbamic acid 6-[6-(4-dimethylamino-3-hydroxy-6-methyl-tetrahydro-pyran-2-yloxy)-14-ethyl-12,13-dihydroxy-7-methoxy-3,5,7,9,11,13-hexamethyl-2,10-dioxo-oxacyclotetradec-4-yloxy]-4-methoxy-2,4-dimethyl-tetrahydro-pyran-3-yl ester) 3-morpholino rifamycin S

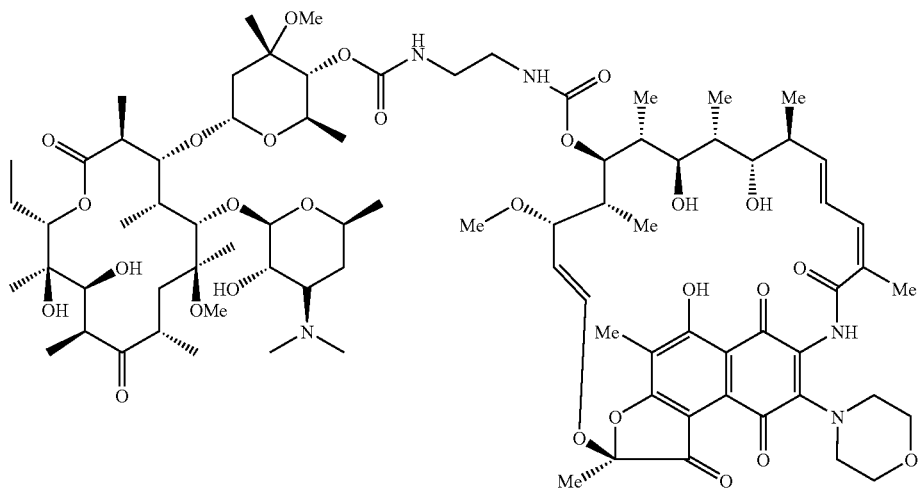

Synthesis: The title compound was prepared as described in Example 6 above, using (2-Amino-ethyl)-carbamic acid 6-[6-(4-dimethylamino-3-hydroxy-6-methyl-tetrahydro-pyran-2-yloxy)-14-ethyl-12,13-dihydroxy-7-methoxy-3,5,7,9,11,13-hexamethyl-2,10-dioxo-oxacyclotetradec-4-yloxy]-4-methoxy-2,4-dimethyl-tetrahydro-pyran-3-yl ester in place of 1-methyl-piperazine. ESI MS m/z (M+H)+ 1598, (M+H—OCH$^3$)+ 1566; $^1$H NMR (400 MHz, CDCl$_3$) δ 7.52 (s, 1H), 6.40 (d, J=14.4 Hz, 1H), 7.23-6.16 (m, 1H), 6.01 (d, J=14.0 Hz, 1H), 5.07-4.20 (complex pattern, 8H), 4.00-2.86 (complex pattern), 2.60-1.41 (complex pattern), 1.38-0.65 (complex pattern), 0.16 (d, J=7.0 Hz, 3H).

EXAMPLE 28

25-O-Desacetyl-(carbonyl-1-cyclopropyl-6-fluoro-8-methoxy-7-(3-methyl-piperazin-1-yl)-4-oxo-1,4-dihydro-quinoline-3-carboxylic acid) 3-morpholino rifamycin S

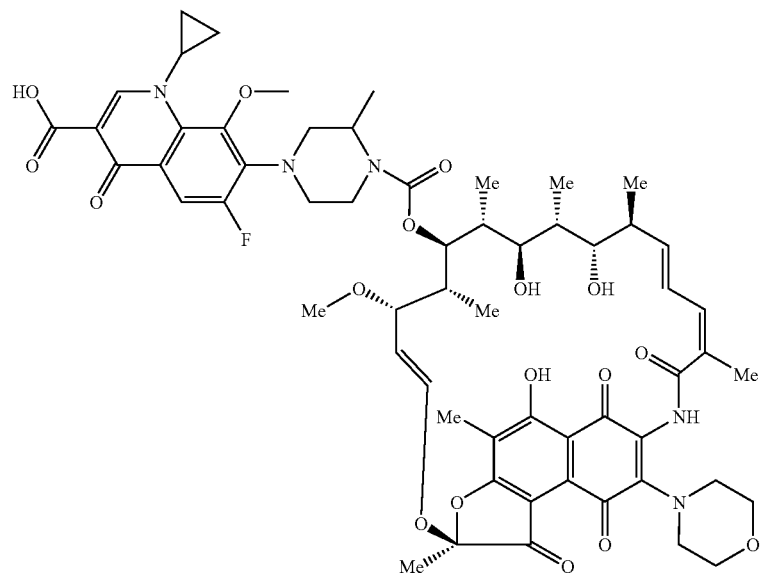

EXAMPLE 29

25-O-Desacetyl-(carbonyl-2-ethyl-octahydro-pyrrolo[3,4-c]pyrrole) 3-morpholino rifamycin S

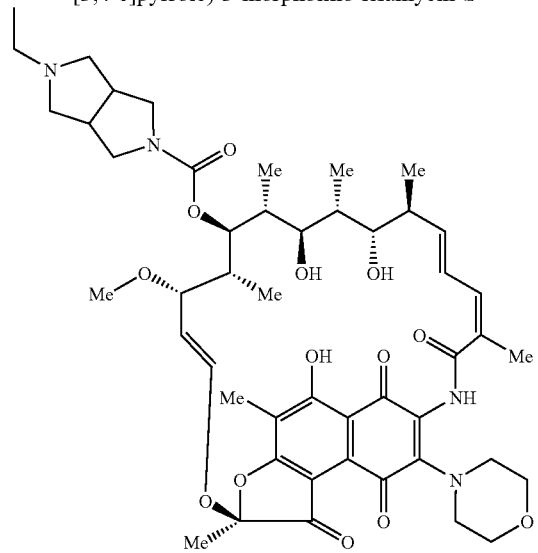

Synthesis: The title compound was prepared as described in Example 6 above, using 1-cyclopropyl-6-fluoro-8-methoxy-7-(3-methyl-piperazin-1-yl)-4-oxo-1,4-dihydro-quinoline-3-carboxylic acid in place of 1-methyl-piperazine. ESI MS m/z (M+H)+ 1140, (M+H—OCH$_3$)+ 1108; $^1$H NMR (400 MHz, CDCl$_3$) δ 13.25 (s, 1H), 8.77 (s, 1H), 7.84 (d, J=12.1 Hz, 1H), 7.48 (s, 1H), 7.16-7.10 (m, 1H), 6.31 (d, J=7.8 Hz, 1H), 6.16-6.13 (m, 1H), 6.05-5.98 (m, 1H), 5.04-4.95 (m, 2H), 4.81-4.70 (m, 1H), 4.40-4.22 (m, 1H), 3.97-3.82 (m, 4H), 3.74-3.63 (m, 2H), 3.66 (s, 3H), 3.52-3.36 (m, 3H), 3.28-3.21 (m, 2H), 3.12-3.03 (m, 3H), 2.33-2.67 (m, 1H), 2.21 (s, 3H), 2.06 (s, 3H), 1.87-1.74 (m, 2H), 1.68 (s, 3H), 1.30-1.24 (m, 3H), 1.19 (s, 3H), 1.17-1.36 (m, 1H), 1.01-0.99 (m, 4H), 0.94-0.91 (m, 1H), 0.85-0.28 (m, 5H), 0.67 (d, J=6.6 Hz, 3H), 0.20-0.18 (m, 3H).

Synthesis: The title compound was prepared as described in Example 6 above, using 2-ethyl-octahydro-pyrrolo[3,4-c]pyrrole in place of 1-methyl-piperazine. ESI MS m/z (M+H)+ 905, (M+H—OCH$_3$)+ 873; $^1$H NMR (400 MHz, CDCl$_3$) δ 13.25 (s, 1H), 7.53 (s, 1H), 6.98 (s, 1H), 6.39 (d, J=10.9 Hz, 1H), 6.21 (dd, J=6.3 and 16.4 Hz, 1H), 6.04 (d, J=12.5 Hz, 1H), 5.05 (dd, J=4.7 and 12.1 Hz, 1H), 4.96 (d, J=9.8 Hz, 1H), 3.97-3.87 (m, 3H), 3.77-3.70 (m, 2H), 3.59-3.47 (m, 3H), 3.38-3.27 (m, 2H), 3.16-3.09 (m, 3H), 2.96-2.74 (m, 3H), 3.97-3.87 (m, 4H), 2.55-2.30 (m, 4H), 2.25 (s, 3H), 2.12 (s, 3H), 1.90-1.81 (m, 4H), 1.74 (s, 3H), 1.13 (m, 3H), 1.04 (d, J=7.0 Hz, 3H), 0.89 (d, J=7.0 Hz, 3H), 0.70 (d, J=6.6 Hz, 3H), 0.20 (d, J=7.4 Hz, 3H).

EXAMPLE 30

25-O-Desacetyl-(carbonyl-N,N-dimethylethylenediamine) 3-morpholino rifamycin S

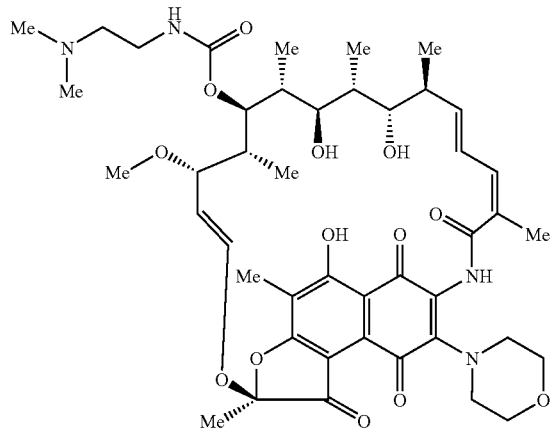

Synthesis: The title compound was prepared as described in Example 6 above, using N,N-dimethylethylenediamine in place of 1-methyl-piperazine. ESI MS m/z (M+H)+ 853, (M+H—OCH³)+ 821; ¹H NMR (400 MHz, CDCl₃) δ 13.25 (s, 1H), 7.52 (s, 1H), 6.98 (s, 1H), 6.39 (d, J=10.9 Hz, 1H), 6.21 (dd, J=6.3 and 15.6 Hz, 1H), 6.04 (d, J=12.1 Hz, 1H), 5.39 (br, 1H), 5.06 (dd, J=4.3 and 12.1 Hz, 1H), 4.93 (d, J=10.2 Hz, 1H), 3.96 (d, J=9.0 Hz, 1H), 3.92-3.87 (m, 3H), 3.68-3.70 (m, 2H), 3.59-3.51 (m, 3H), 3.35-3.29 (m, 2H), 3.24 (q, J=5.5 Hz 2H), 3.17 (d, J=9.8 Hz, 1H), 3.12 (s, 3H), 2.45-2.39 (m, 2H), 2.37-2.32 (m, 2H), 2.25 (s, 3H), 2.23 (s, 3H), 2.23-2.20 (m, 1H), 1.88-1.75 (m, 4H), 1.74 (s, 3H), 1.61-1.55 (m, 3H), 1.43 (s, 3H), 1.04 (d, J=7.0 Hz, 3H), 1.04 (d, J=6.6 Hz, 3H), 0.69 (d, J=6.6 Hz, 3H), 0.18 (d, J=7.0 Hz, 3H).

EXAMPLE 31

25-O-Desacetyl-(carbonyl-2-(1-methyl-pyrrolidin-2-yl)-ethylamine) 3-morpholino rifamycin S

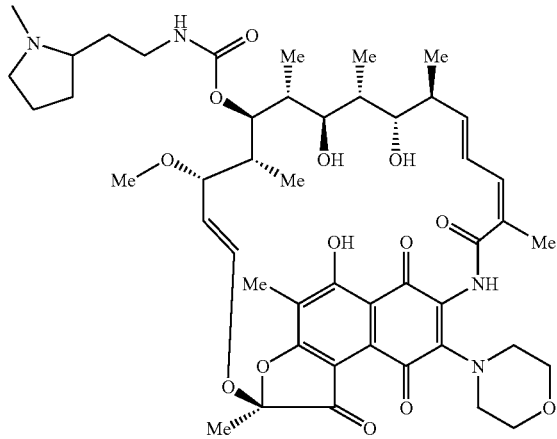

Synthesis: The title compound was prepared as described above using 2-(1-methyl-pyrrolidin-2-yl)-ethylamine. ESI MS m/z (M+H)+ 893, (M+H—OCH₃)+ 861; ¹H NMR (400 MHz, CDCl₃) δ 13.25 (s, 1H), 7.51 (s, 1H), 6.97 (s, 0.5H), 6.40 (d, J=10.6 Hz, 1H), 6.22 (dd, J=5.9 and 15.6 Hz, 1H), 6.04 (d, J=12.1 Hz, 1H), 5.05 (dd, J=4.3 and 12.1 Hz, 1H), 6.22 (dd, J=5.9 and 15.6 Hz, 1H), 4.92 (d, J=9.4 Hz, 1H), 4.90 (br, 1H), 6.22 (dd, J=5.9 and 15.6 Hz, 1H), 3.96 (d, J=9.8 Hz, 1H), 3.92-3.87 (m, 2H), 3.76-3.71 (m, 2H), 3.57-3.49 (m, 3H), 3.34-3.29 (m, 2H), 3.27-3.20 (m, 2H), 3.10 (s, 3H), 2.35-2.30 (m, 2H), 2.25 (s, 3H), 2.11 (s, 3H), 1.86-1.77 (m, 2H), 1.74 (s, 3H), 1.63-1.53 (m, 4H), 1.42 (s, 3H), 1.04 (d, J=7.0 Hz, 3H), 0.89 (d, J=7.0 Hz, 3H), 0.68 (d, J=7.0 Hz, 3H), 0.18 (d, J=7.0 Hz, 3H).

EXAMPLE 32

25-O-Desacetyl-(carbonyl-2-Pyrrolidin-1-yl-ethylamine) 3-morpholino rifamycin S

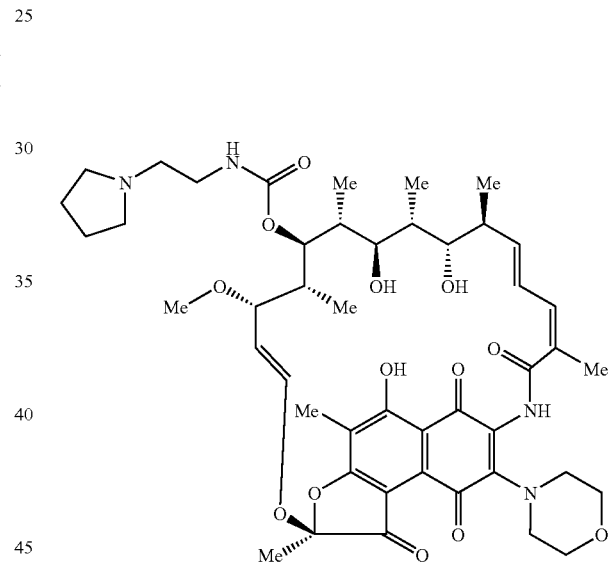

Synthesis: The title compound was prepared as described above, using 2-pyrrolidin-1-yl-ethylamine in place of 1-methyl-piperazine. ESI MS m/z (M+H)+ 879, (M+H—OCH₃)+ 847; ¹H NMR (400 MHz, CDCl₃) δ 13.25 (s, 1H), 7.51 (s, 1H), 6.98 (s, 0.5H), 7.62 (d, J=8.0 Hz, 1H), 6.39 (d, J=10.9 Hz, 1H), 6.21 (dd, J=6.6 and 16.2 Hz, 1H), 6.063 (dd, J=1.4 and 12.3 Hz, 1H), 5.06 (dd, J=4.5 and 12.5 Hz, 1H), 4.93 (d, J=10.2 Hz, 1H), 3.97-3.87 (m, 3H), 3.77-3.71 (m, 2H), 3.58-3.52 (m, 2H), 3.34-3.27 (m, 3H), 3.18-3.16 (m, 1H), 3.11 (s, 3H), 2.64-2.47 (m, 5H), 2.37-2.31 (m, 1H), 2.25 (s, 3H), 2.12 (s, 3H), 1.72 (s, 3H), 1.04 (d, J=7.0 Hz, 3H), 0.89 (d, J=7.0 Hz, 3H), 0.68 (d, J=6.8 Hz, 3H), 0.18 (d, J=7.0 Hz, 3H).

EXAMPLE 33

25-O-Desacetyl-(carbonyl-1-benzyl-piperidin-4-ylamine) 3-morpholino rifamycin S

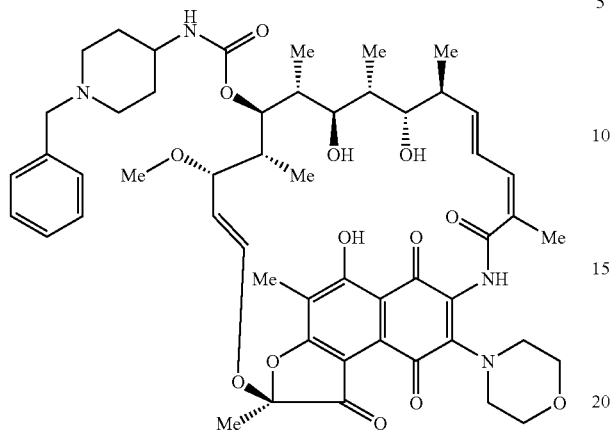

Synthesis: The title compound was prepared as described in Example 6 above, using 1-benzyl-piperidin-4-ylamine in place of 1-methyl-piperazine. ESI MS m/z (M+H)$^+$ 955, (M+H—OCH$^3$)$^+$ 923; $^1$H NMR (400 MHz, CDCl$_3$) δ 13.25 (s, 1H), 7.52 (s, 1H), 7.35-7.30 (m, 5H), 6.39 (d, J=10.6 Hz, 1H), 6.20 (d, J=6.3 and 16.0 Hz, 1H), 5.04 (dd, J=4.3 and 12.1 Hz, 1H), 4.90 (d, J=10.2 Hz, 1H), 4.79-4.77 (m, 1H), 3.96-3.85 (m, 3H), 3.76-3.71 (m, 2H), 3.57-3.48 (m, 4H), 3.34-3.29 (m, 2H), 3.15-3.11 (m, 1H), 3.10 (s, 3H), δ 3.06-3.04 (m, 1H), δ 2.92-2.80 (m, 1H), 2.36-2.30 (m, 1H), 2.25 (s, 3H), 2.12 (s, 3H), 1.96-1.80 (m, 3H), 1.74 (s, 3H), 1.62-1.56 (s, 1H), 1.03 (d, J=7.0 Hz, 3H), 0.88 (d, J=7.0 Hz, 3H), 0.67 (d, J=7.0 Hz, 3H), 0.17 (d, J=7.0 Hz, 3H).

EXAMPLE 34

25-O-Desacetyl-(carbonyl-4-phenyl-butylamine) 3-morpholino rifamycin S

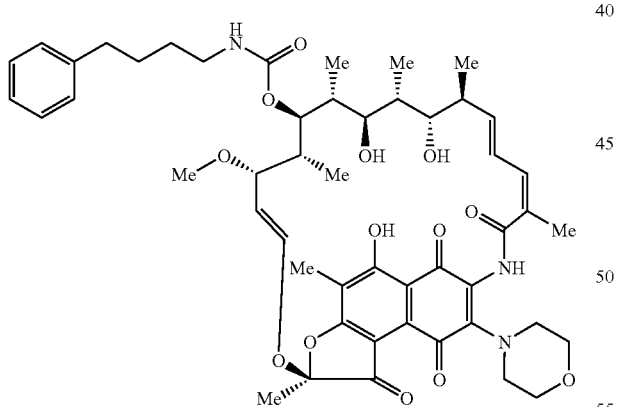

Synthesis: The title compound was prepared as described in Example 6 above, using 4-phenyl-butylamine in place of 1-methyl-piperazine. ESI MS m/z (M+H)$^+$ 914, (M+H—OCH$^3$)$^+$ 882; $^1$H NMR (400 MHz, CDCl$_3$) δ 13.25 (s, 1H), 7.52 (s, 1H), 7.28-7.24 (m, 2H), 7.19-7.12 (m, 3H), 6.39 (d, J=10.6 Hz, 1H), 6.20 (dd, J=6.3 and 15.6 Hz, 1H), 6.03 (d, J=12.1 Hz, 1H), 5.04 (dd, J=4.7 and 12.5 Hz, 1H), 4.92 (d, J=9.8 Hz, 1H), 4.82 (d, J=3.5 Hz, 1H), 4.77-4.76 (m, 1H), 3.96 (d, J=9.4 Hz, 1H), 3.92-3.67 (m, 2H), 3.76-3.71 (m, 2H), 3.56-3.50 (m, 3H), 3.34-3.29 (m, 2H), 3.21-3.12 (m, 2H), 3.08 (s, 3H), 2.61 (t, J=7.0 Hz, 2H), 2.37-2.31 (m, 2H), 2.25 (s, 3H), 2.12 (s, 3H), 1.91-1.78 (m, 3H), 1.75 (s, 3H), 1.65-59 (m, 2H), δ 1.53-1.48 (m, 2H), 1.01 (d, J=7.0 Hz, 3H), 0.88 (d, J=6.5 Hz, 3H), 0.67 (d, J=7.0 Hz, 3H), 0.17 (d, J=7.0 Hz, 3H).

EXAMPLE 35

25-O-Desacetyl-(carbonyl-[1,4']bipiperidinyl) 3-morpholino rifamycin S

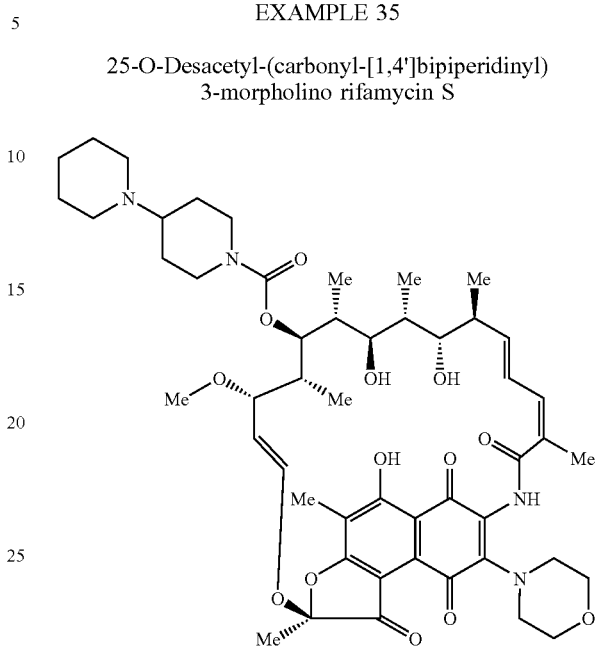

Synthesis: The title compound was prepared as described above, using [1,4']Bipiperidinyl in place of 1-methyl-piperazine. ESI MS m/z (M+H)$^+$ 933, (M+H—OCH$_3$)$^+$ 901; $^1$H NMR (400 MHz, CDCl$_3$) δ 13.25 (s, 1H), 7.52 (s, 1H), 6.98 (s, 0.5H), 6.39 (d, J=10.9 Hz, 1H), 6.2 (dd, J=5.9 and 16.4 Hz, 1H), 6.04 (d, J=12.1 Hz, 1H), 5.05 (d, J=11 Hz, 1H), 4.93 (d, J=10.7 Hz, 1H), 4.27-4.19 (m, 1H), 4.15-4.07 (m, 1H), 3.96-3.83 (m, 3H), 3.77-3.68 (m, 2H), 3.61-3.52 (m, 2H), 3.50-3.47 (m, 1H), 3.36-3.28 (m, 2H), 3.11 (s, 1.5H), 3.08 (s, 1.5H), 2.84-2.68 (m, 4H), 2.59-2.49 (m, 4H), 2.27 (s, 3H), 2.26 (s, 3H), 2.18 (s, 3H), 1.96-1.76 (m, 7H), 1.74 (s, 3H), 1.04 (d, J=7 Hz, 3H), 1.04 (d, J=6.6 Hz, 3H), 0.70 (d, J=6.6 Hz, 3H), 0.21 (d, J=7 Hz, 3H).

EXAMPLE 36

25-O-Desacetyl-(carbonyl-(4-aminomethyl-phenyl)-dimethyl-amine) 3-morpholino rifamycin S

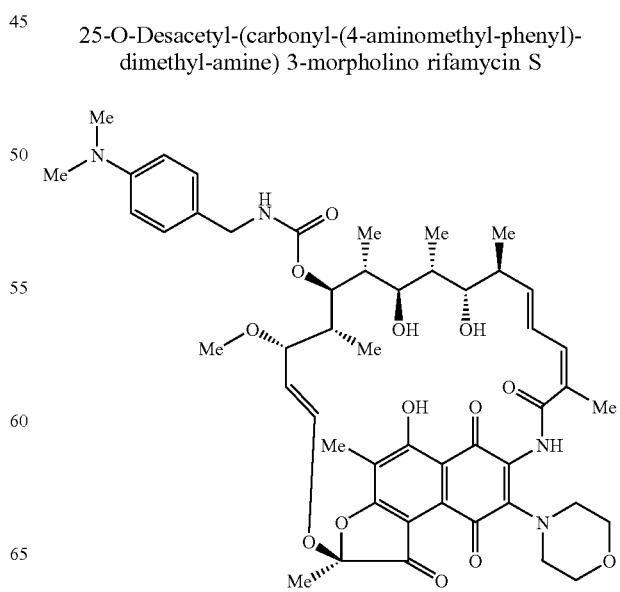

Synthesis: The title compound was prepared as described in Example 6 above, using (4-aminomethyl-phenyl)-dimethyl-amine in place of 1-methyl-piperazine. ESI MS m/z (M+H)$^+$ 915, (M+H—OCH$_3$)$^+$ 883; $^1$H NMR (400 MHz, CDCl$_3$) δ 13.25 (s, 1H), 7.51 (s, 1H), 7.11 (d, J=8.6 Hz, 2H), 6.66 (d, J=8.6 Hz, 2H), 6.39 (d, J=11.0 Hz, 1H), 6.22 (dd, J=6.6 and 16.0 Hz, 1H), 6.03 (d, J=12.5 Hz, 1H), 5.04 (dd, J=4.3 and 12.1 Hz, 1H), 4.96 (d, J=5.5 Hz, 1H), 4.85 (d, J=3.9 Hz, 1H), 4.22 (d, J=5.9 Hz, 2H), 3.97 (d, J=9.0 Hz, 1H), 3.92-3.87 (m, 3H), 3.76-3.68 (m, 3H), 3.56-3.51 (m, 3H), 3.34-3.28 (m, 2H), 3.20-3.15 (m, 1H), 3.08 (s, 3H), 2.92 (s, 6H), 2.37-2.32 (m, 1H), 2.26 (s, 3H), 2.12 (s, 3H), 1.90-1.76 (m, 2H), 1.74 (s, 3H), 1.70-1.56 (m, 3H), 1.05 (d, J=7.0 Hz, 3H), 0.89 (d, J=7.0 Hz, 3H), 0.66 (d, J=6.6 Hz, 3H), 0.17 (d, J=7.0 Hz, 3H).

EXAMPLE 37

25-O-Desacetyl-(carbonyl-N'-benzyl-N,N-dimethyl-ethane-1,2-diamino) 3-morpholino rifamycin S

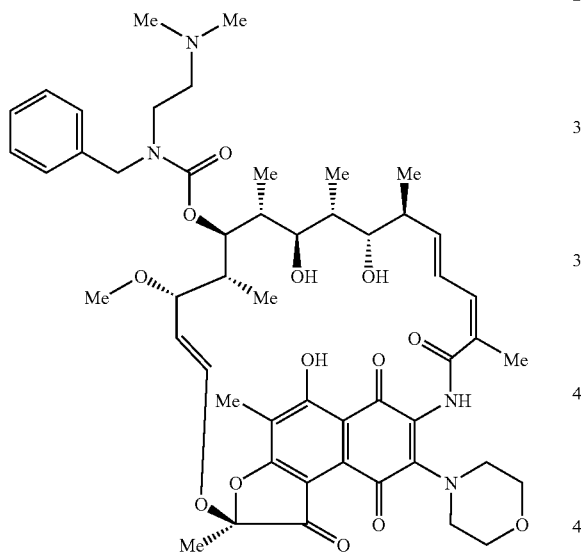

Synthesis: The title compound was prepared as described in Example 6 above, using N'-benzyl-N,N-dimethyl-ethane-1,2-diamine in place of 1-methyl-piperazine. ESI MS m/z (M+H)$^+$ 943, (M+H—OCH$_3$)$^+$ 911; $^1$H NMR (400 MHz, CDCl$_3$) δ 13.25 (s, 1H), δ 7.48-7.44 (m, 1H), δ 7.26-7.15 (m, 4H), δ 7.08 (d, J=7.0 Hz, 1H), δ 6.33 (d, J=10.2 Hz, 1H), δ 6.14 (dd, J=7.0 and 16.0 Hz, 1H), δ 5.99 (d, J=12.1 Hz, 0.5H), δ 5.86 (d, J=12.1 Hz, 0.5H), δ 5.03-4.98 (m, 1H), δ 4.77 (dd, J=4.3 and 10.6 Hz, 1H), δ 4.43-4.35 (m, 1H), δ 3.92-3.77 (m, 2H), δ 3.71-3.63 (m, 2H), δ 3.51-3.42 (m, 3H), δ 3.28-3.17 (m, 3H), δ 3.10-3.08 (m, 1H), δ 3.03 (s, 1.5H), δ 2.99 (s, 1.5H), δ 2.98-2.95 (m, 1H), δ 2.48-2.32 (m, 1H), δ 2.31-2.24 (m, 1H), δ 3.51-3.42 (m, 3H), δ 2.20 (s, 1.5H), δ 2.19 (s, 1.5H), δ 2.18 (s, 1.5H), δ 2.13 (s, 1.5H), δ 1.89-1.70 (m, 4H), δ 1.68 (s, 1.5H), δ 1.67 (s, 1.5H), δ 1.56-1.52 (m, 2H), ), δ 1.01-0.98 (m, 3H), δ 0.84-0.81 (m, 3H), δ 0.66 (d, J=6.6 Hz, 1.5H), δ 0.50 (d, J=6.6 Hz, 1.5H), δ 0.17 (d, J=7.0 Hz, 1.5H), δ 0.07 (d, J=7.4 Hz, 1.5H),

EXAMPLE 38

25-O-Desacetyl-(carbonyl-2-(4-Chloro-phenyl)-ethylamine) 3-morpholino rifamycin S

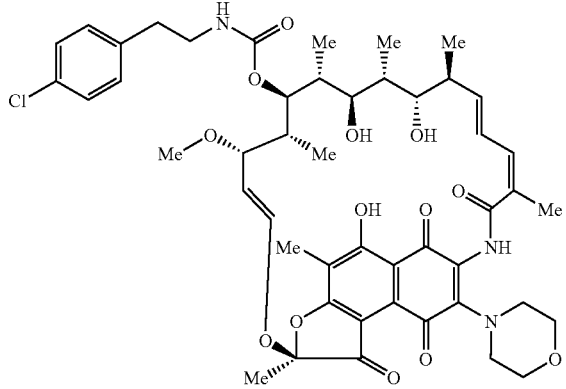

Synthesis: The title compound was prepared as described in Example 6 above, using 2-(4-chloro-phenyl)-ethylamine in place of 1-methyl-piperazine. ESI MS m/z (M+H)$^+$ 920, (M+H—OCH$_3$)$^+$ 888; $^1$H NMR (400 MHz, CDCl$_3$) δ 13.25 (s, 1H), 7.52 (s, 1H), 7.30-7.24 (m), 7.09 (d, J=7.0 Hz, 2H), 6.38 (d, J=11.3 Hz, 1H), 6.20 (dd, J=5.5 and 15.6 Hz, 1H), 6.03 (d, J=12.1 Hz, 1H), 5.03 (d, J=12.1 Hz, 1H), 4.91 (d, J=10.2 Hz, 1H), 4.80-4.78 (m, 1H), 4.76-4.72 (m, 1H), 3.96-3.87 (m, 3H), 3.82-3.71 (m, 3H), 3.55-3.29 (m, 6H), 3.06 (s, 3H), 2.78-2.72 (m, 2H), 2.39-2.30 (m, 1H), 2.25 (s, 3H), 2.14 (s, 3H), 1.98-1.90 (m, 1H), 1.83-1.79 (m, 3H), 1.74 (s, 3H), 1.62-1.53 (m, 2H), 1.04 (d, J=6.6 Hz, 3H), 0.90 (d, J=6.2 Hz, 3H), 0.65 (d, J=6.6 Hz, 3H), 0.17 (d, J=7.0 Hz, 3H).

EXAMPLE 39

25-O-Desacetyl-(carbonyl-3-chloro-benzylamine) 3-morpholino rifamycin S

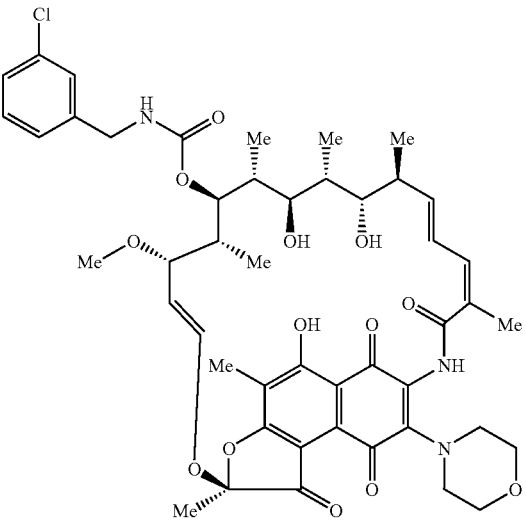

Synthesis: The title compound was prepared as described in Example 6 above, using 3-chloro-benzylamine in place of 1-methyl-piperazine. ESI MS m/z (M+H)+ 906, (M+H—OCH³)+ 874; ¹H NMR (400 MHz, CDCl₃) δ 13.25 (s, 1H), 7.55 (s, 1H), 7.25-7.29 (m, 5H), 7.14-7.11 (m, 1H), δ 6.39 (d, J=10.9 Hz, 1H), 6.20 (dd, J=6.6 and 16.0 Hz, 1H), 6.04 (d, J=13.7 Hz, 1H), δ 5.18 (t, J=6.3 Hz, 1H), 5.05 (dd, J=4.7 and 12.5 Hz, 1H), 4.98 (d, J=9.8 Hz, 1H), δ 6.67-6.64 (m, 1H), 4.31 (dd, J=6.3 and 11.7 Hz, 2H), 3.95 (d, J=9.0 Hz, 1H), δ 3.92-3.87 (m, 3H), 3.79-3.71 (m, 3H), 3.57-3.52 (m, 2H), 3.34-3.29 (m, 2H), 3.19-3.14 (m, 1H), 3.06 (s, 3H), 2.38-2.32 (m, 1H), 2.26 (s, 3H), 2.12 (s, 3H), 1.87-1.79 (m, 2H), 1.74 (s, 3H), 1.68-1.59 (m, 3H), δ 1.04 (d, J=6.6 Hz, 3H), 0.98 (d, J=7.0 Hz, 3H), 0.69 (d, J=7.0 Hz, 3H), 0.19 (d, J=6.6 Hz, 3H).

EXAMPLE 40

25-O-Desacetyl-(carbonyl-4-nitro-benzylamine) 3-morpholino rifamycin S

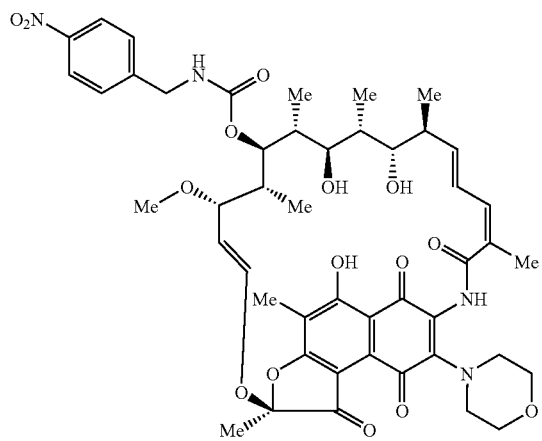

Synthesis: The title compound was prepared as described in Example 6 above, using 4-nitro-benzylamine in place of 1-methyl-piperazine. ESI MS m/z (M+H)+ 916, (M+H—OCH³)+ 884; ¹H NMR (400 MHz, CDCl₃) δ 13.25 (s, 1H), 8.18 (d, J=8.6 Hz, 2H), 7.54 (s, 1H), 7.42 (d, J=8.6 Hz, 2H), 7.21-7.14 (m, 1H), 6.37 (d, J=10.6 Hz, 1H), 6.17 (dd, J=6.3 and 16.0 Hz, 1H), 6.04 (d, J=12.5 Hz, 1H), 5.35-5.32 (m, 1H), 5.05 (dd, J=5.1 and 12.1 Hz, 1H), 4.96 (d, J=9.8 Hz, 1H), 4.54-4.50 (m, 1H), δ 4.46-4.32 (m, 1H), 3.95-3.87 (m, 3H), 3.76-3.71 (m, 2H), δ 3.57-3.50 (m, 3H), 3.34-3.29 (m, 2H), 3.15-3.11 (m, 1H), δ 3.05 (s, 3H), 2.39-2.31 (m, 1H), 2.25 (s, 3H), 2.12 (s, 3H), 3.76-3.71 (m, 2H), 1.98-1.94 (m, 1H), 1.87-1.79 (m, 2H), 1.74 (s, 3H), δ 1.69-1.57 (m, 4H), 3.76-3.71 (m, 2H), 1.04 (d, J=7.0 Hz, 3H), 0.88 (d, J=7.0 Hz, 3H), 0.69 (d, J=7.0 Hz, 3H), 0.19 (d, J=7.0 Hz, 3H).

EXAMPLE 41

25-O-Desacetyl-(carbonyl-N-quinolin-3-yl-methylamino) 3-morpholino rifamycin S

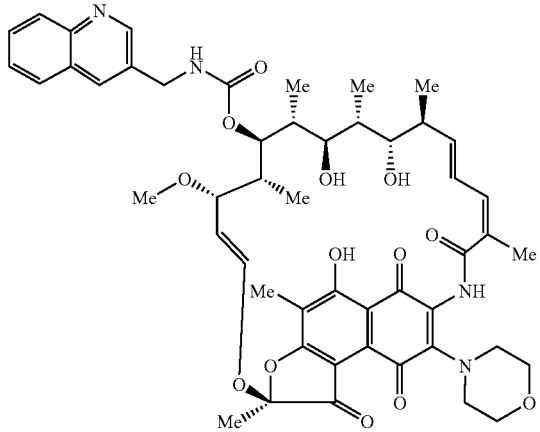

Synthesis: The title compound was prepared as described in Example 6 above, using C-Quinolin-3-yl-methylamine in place of 1-methyl-piperazine. ESI MS m/z (M+H)+ 923, (M+H—OCH³)+ 891; ¹H NMR (400 MHz, CDCl₃) δ 13.25 (s, 1H), 8.23 (m, 1H), 8.10-8.07 (m, 2H), 7.77 (d, J=7.8 Hz, 1H), 7.73-7.70 (m, 1H), 7.58-7.52 (m, 2H), 7.25-7.18 (m, 1H), 6.38 (d, J=11.3 Hz, 1H), 6.18 (d, J=6.3 and 15.6 Hz, 1H), 6.02 (d, J=12.1 Hz, 1H), 5.36-5.33 (m, 1H), 5.06-4.98 (m, 2H), 4.68-4.63 (m, 1H), 4.54 (dd, J=6.3 and 12.5 Hz, 2H), 3.96-3.87 (m, 3H), 3.46-3.71 (m, 3H), 3.53 (m, 2H), 3.39-3.28 (m, 2H), δ 3.17-3.11 (m, 1H), 3.00 (s, 3H), 2.37-2.31 (m, 1H), 2.25 (s, 3H), 2.12 (s, 3H), 2.00-1.92 (m, 1H), 1.88-1.78 (m, 2H), 1.73 (s, 3H), 1.69-1.58 (m, 4H), 1.00 (d, J=6.6 Hz, 3H), 0.88 (d, J=6.6 Hz, 3H), 0.68 (d, J=6.6 Hz, 3H), 0.18 (d, J=7.0 Hz, 3H).

EXAMPLE 42

25-O-Desacetyl-(carbonyl-1-Cyclopropyl-6-fluoro-4-oxo-7-piperazin-1-yl-1,4-dihydro-quinoline-3-carboxylic acid) 3-morpholino rifamycin S

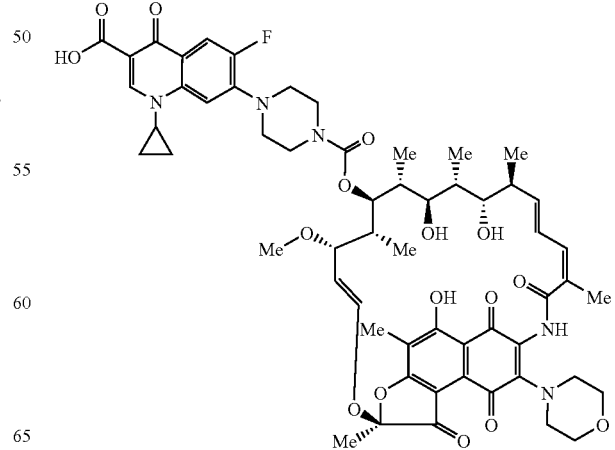

Synthesis: The compound of Example 4 (10 mg, 0.010 mmol) was dissolved in methylene chloride (1 ml). To this was added 1-cyclopropyl-6-fluoro-4-oxo-7-piperazin-1-yl-1,4-dihydro-quinoline-3-carboxylic acid (10 mg, 0.030 mmol) and N-methylmorpholine (6 μl, 0.050 mmol). The resulting solution was stirred at room temperature for 30 minutes. The reaction mixture was diluted with ethyl acetate (3 ml) and washed with 1 M aqueous citric acid (3 ml) followed by washing with saturated sodium chloride (3 ml). The resulting solution was dried with sodium sulfate, filtered, and evaporated to produce a dark solid. This residue was taken up in 1:2 (V/V) 1 M aqueous HCl/tetrahydrofuran (1 ml) and stirred for 3 hours. After which time the mixture was diluted with ethyl acetate (3 ml) and the aqueous layer was removed. This solution was vigorously washed with an aqueous solution consisting of 5% (W/V) potassium ferricyanide and 5% (W/V) sodium bicarbonate, which was then followed by multiple washes with saturated sodium chloride. The resulting solution was dried with sodium sulfate, filtered, and evaporated. The residue was purified by silica gel column chromatography (step gradient; (99.9% EtOAc/0.01% HOAc) to (89.9% EtOAc/10% MeOH/0.01% HOAc) to (49.9% EtOAc/50% MeOH/0.01% HOAc) to produce the title compound. ESI MS m/z (M+H)$^+$ 1096; $^1$H NMR (400 MHz, CDCl$_3$) δ 13.25 (s, 1H), 8.79 (s, 1H), 8.06 (d, J=12.5 Hz, 1H), 7.56 (s, 1H), 6.36 (d, J=10.6 Hz, 1H), δ 6.16 (dd, J=6.6 and 16.4 Hz, 1H), 6.07 (d, J=10.9 Hz, 1H), 5.09 (dd, J=5.1 and 13.7 Hz, 1H), 5.02 (d, J=10.2 Hz, 1H), δ 3.95-3.87 (m, 3H), 3.77-3.62 (m, 4H), 3.58-3.50 (m, 3H), 3.35-3.22 (m, 5H), 3.12 (s, 3H), 2.38-2.33 (m, 1H), 2.27 (s, 3H), 2.14-2.12 (m, 2H), 2.09 (s, 3H), 1.88-1.79 (m, 1H), 1.74 (s, 3H), 1.05 (d, J=7.0 Hz, 3H), 0.89-0.78 (m, 7H), 0.72 (d, J=6.6 Hz, 3H), 0.24 (d, J=7.0 Hz, 3H).

EXAMPLE 43

25-O-Desacetyl-(carbonyl-prop-2-ynylamino) 3-morpholino rifamycin S

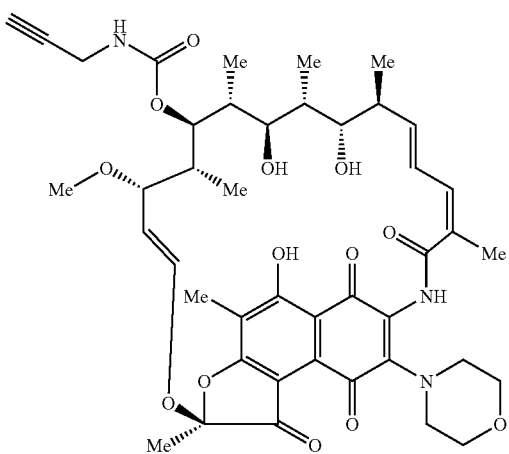

Synthesis: The title compound was prepared as described above using prop-2-ynyl amine. ESI MS m/z (M+H)$^+$ 820.0; $^1$H NMR (400 MHz, CDCl$_3$) δ 13.23 (s, 1H), 7.48 (s, 1H), 6.96 (s, 1H), 6.37 (d, J=11.0 Hz, 1H), 6.19 (dd, J=15.7, 6.3 Hz, 1H), 6.03 (d, J=11.7 Hz, 1H), 6.37 (d, J=11.0 Hz, 1H), 6.19 (dd, J=15.7, 6.3 Hz, 1H), 5.03 (d, J=11.7 Hz, 2H), 4.60-4.50 (m, 1H), 3.98-3.84 (m, 4H), 3.78-3.68 (m, 3H), 3.56-3.48 (m, 2H), 3.15 (br d, J=9.4 Hz, 1H), 3.11 (s, 3H), 2.34-2.28 (m, 1H), 2.24 (s, 3H), 2.21 (app t, J=2.3 Hz, 1H), 2.10 (s, 3H), 2.03 (s, 2H), 1.90-1.72 (m, 2H), 1.72 (s, 3H), 1.68-1.58 (m, 3H), 1.02 (d, J=7.0 Hz, 3H), 0.88 (d, J=7.0 Hz, 3H), 0.67 (d, J=7.0 Hz, 3H), 0.16 (d, J=7.0 Hz, 3H).

EXAMPLE 44

25-O-Desacetyl-(carbonyl-[3-(3-amino-prop-1-ynyl)-phenyl]-methanol) 3-morpholino rifamycin S

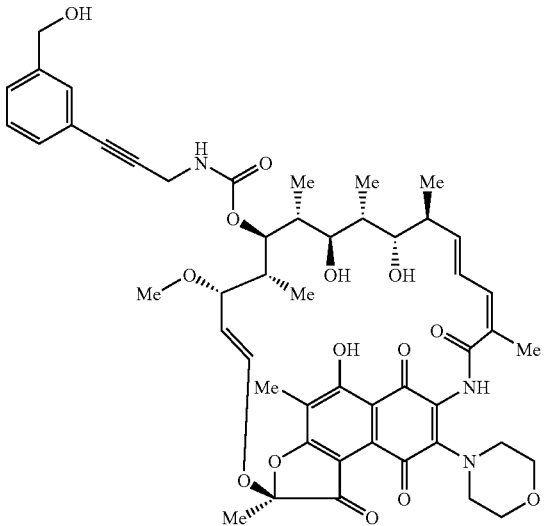

Synthesis: 3-Iodobenzyl alcohol (37 μL, 0.29 mmol), potassium carbonate (39 mg, 0.29 mmol), copper iodide (6.5 mg, 0.03 mmol), 10% Pd—C (1.1 mg, 0.01 mmol), and triphenyl phosphine (9 mg, 0.03 mmol) was suspended in a 1:1 mixture of 1,2-dimethoxyethane and water (0.8 mL). The suspension was stirred at room temperature for 30 minutes. The compound of Example 43 (89 mg, 0.11 mmol) was then added in a 1:1 mixture of 1,2-dimethoxyethane and water (0.8 mL) and the reaction mixture was allowed to reflux overnight. After refluxing overnight, it was observed that the palladium catalyst had plated out on the sides of the round bottom flask. The reaction was cooled to room temperature, diluted with ethyl acetate (25 mL) and washed sequentially with water and a saturated potassium ferricyanide phosphate buffer (pH=7.4). The organic layer was separated, dried over sodium sulfate and concentrated to give a purple residue. The acetonide was removed as described in the procedure for the preparation of the title compound. The material was determined to be pure by $^1$H NMR and LC/MS and was taken directly to the next step without further purification. ESI MS m/z (M+H)$^+$ 926.1; $^1$H NMR (400 MHz, CDCl$_3$) δ 13.23 (s, 1H, 7.49 (s, 1H), 7.36 (s, 1H), 7.30-7.26 (m, 3H), 6.38 (d, J=11 Hz, 1H, 6.19 (dd, J=16.5, 7.0 Hz, 1H), 6.02 (d, J=11.7 Hz, 1H, 5.12-4.92 (m, 3H), 4.68-4.58 (m, 2H), 4.20-4.08 (m, 2H), 3.93(d, J=9.4 Hz, 1H, 3.92-3.84 (m, 2H), 3.78-3.68 (m, 3H), 3.56-3.48 (m, 3H), 3.32-3.24 (m, 2H), 3.20-3.26 (m, 1H), 3.11 (s, 3H), 2.36-2.28 (m, 1H), 2.24 (s, 3H), 2.10 (s, 2H), 1.90-1.76 (m, 2H), 1.72 (s, 3H), 1.64-1.56 (m, 1H), 1.57 (s, 2H), 1.01 (d, J=7.0 Hz, 3H), 1.00-0.97 (m, 1H), 0.87 (d, J=7.0 Hz, 3H), 0.88-0.86 (m, 1H), 0.76 (d, J=6.3 Hz, 1H, 0.68 (d, J=6.3 Hz, 2H), 0.17 (d, J=7.0 Hz, 3H).

EXAMPLE 45

25-O-Desacetyl-(carbonyl-3-quinolin-3-yl-prop-2-ynylamine) 3-morpholino rifamycin S

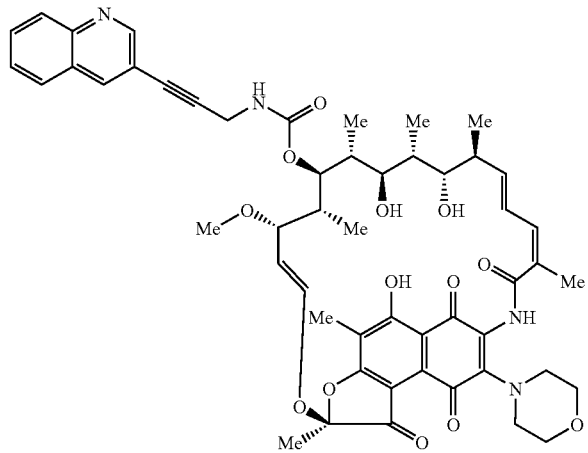

Synthesis: The title compound was prepared as described in Example 41 above, using 3-bromoquinoline and the compound of Example 44. ESI MS m/z (M+H)+ 947.1; 1H NMR (400MHz, CDCl3) δ 13.23 (s, 1H), 8.82 (d, J=2.3 Hz, 1H) 8.16 (d, J=1.6 Hz, 1H), 8.06 (d, J=7.8 Hz, 1H), 7.78-7.68 (m, 2H), 7.56 (app t, J=7.4 Hz, 1H), 7.49 (s, 1H), 7.22 (dd, J=11.7, 4.7 Hz, 1H), 6.37 (d, J=11.0 Hz, 1H), 6.18 (dd, J=16.4, 6.3 Hz, 1H), 6.02 (d, J=11.7 Hz, 1H), 5.18 (app t, J=5.5 Hz, 1H), 5.07 (dd, J=12.5, 4.7 Hz, 1H), 5.01 (d, J=10.2 Hz, 1H), 4.59 (d, J=3.9 Hz, 1H), 4.23 (dd, J=12.5, 6.3 Hz, 2H), 3.94 (d, J=9.4 Hz, 1H), 3.94-3.88 (m, 3H), 3.82-3.66 (m, 4H), 3.56-3.46 (m, 2H), 3.19 (br d, J=10.2 Hz, 1H), 3.13 (s, 3H), 2.36-2.28 (m, 1H), 2.24 (s, 2H), 2.10 (s, 3H), 1.90-1.77 (m, 2H), 1.71 (s, 3H), 1.67-1.60 (m, 1H), 1.58 (s, 3H), 1.02 (d, J=7.0 Hz, 3H), 0.87 (d, J=7.0 Hz, 3H), 0.78 (app t, J=5.5 Hz, 1H), 0.69 (d, J=7.0 Hz, 3H), 0.17 (d, J=7.0 Hz, 3H).

EXAMPLE 46

25-O-Desacetyl-(carbonyl-C-[3-(2-methoxy-phenyl)-isoxazol-5-yl]-methylamino) 3-morpholino rifamycin S

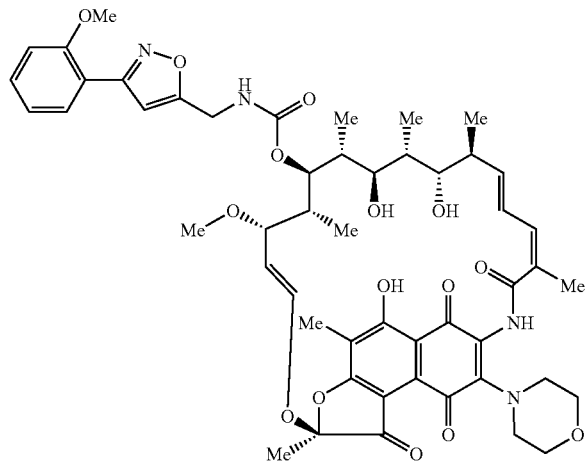

Synthesis: 2-Methoxy-phenyl hydroximoyl chloride (Zamponi, et al., 2003) (7.5 mg, 0.04 mmol) was dissolved in anhydrous benzene (0.1 mL) at room temperature. To this solution was added triethylamine (5.5 μL, 0.04 mmol). Formation of a white precipitate was observed. The compound of example 43 (31 mg, 0.04 mmol) in anhydrous benzene (0.6 mL) was then added dropwise. As judged by LC/MS, the reaction was 50% complete in one hour. The reaction was diluted with ethyl acetate (10 mL), washed sequentially with water and saturated potassium ferricyanide in a phosphate buffer (pH=7.4). The organic layer was dried over sodium sulfate and concentrated to a purple residue. The residue was purified on preparative thin layer chromatography plates (50% ethyl acetate/hexanes) to give 10.7 mg of the title compound in 64% yield. ESI MS m/z (M+H—OCH3)+ 937.3; 1H NMR (400 MHz, CDCl3) δ 13.23 (s, 1H), 7.86-7.77 (m, 1H), 7.48 (s, 1H), 7.42-7.35 (m, 1H), 7.22 (dd, J=15.6, 11.0 Hz, 1H), 7.04-6.94 (m, 2H), 6.66 (s, 1H), 6.36 (d, J=11.0 Hz, 1H), 6.17 (dd, J=15.7, 6.3 Hz, 1H), 6.03-5.93 (m, 1H), 5.36 (app t, J=6.3 Hz, 1H), 5.03 (dd, J=12.5, 4.7 Hz, 1H), 4.98 (d, J=10.2 Hz, 1H, 4.59-4.40 (m, 3H), 3.96-3.78 (m, 4H), 3.85 (s, 3H), 3.78-3.68 (m, 3H), 3.54-3.46 (m, 3H), 3.32-3.24 (m, 2H), 3.16-3.08 (m, 1H), 3.03 (s, 3H), 2.36-2.26 (m, 1H), 2.23 (s, 3H), 2.09 (s, 3H), 1.88-1.76 (m, 2H), 1.70 (s, 3H), 1.68-1.54 (m, 2H), 0.98 (d, J=7.0 Hz, 3H), 0.86 (d, J=7.0 Hz, 3H), 0.67 (d, J=6.3 Hz, 3H), 0.16 (d, J=7.0 Hz, 3H).

EXAMPLE 47

25-O-Desacetyl-(carbonyl-C-(3-Pyridin-2-yl-isoxazol-5-yl)-methylamino) 3-morpholino rifamycin S

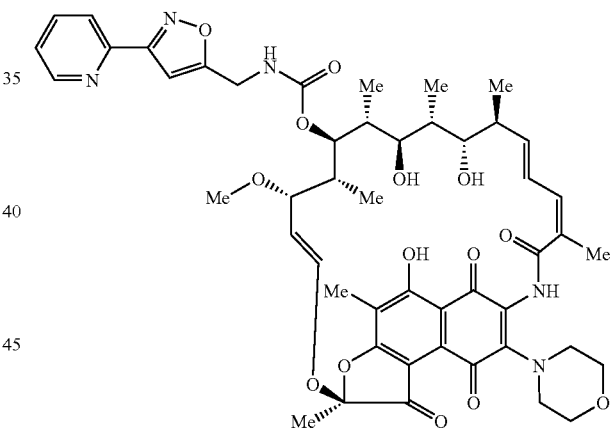

Synthesis: 3-Pyridinyl hydroximoyl chloride (Kocevar, et al., 1988) (4.4 mg, 0.03 mmol) was dissolved in anhydrous tetrahydrofuran (0.1 mL) at room temperature. To this solution was added triethylamine (4 μL, 0.03 mmol). The compound of Example 43 (21.4 mg, 0.03 mmol) in anhydrous tetrahydrofuran (0.6 mL) was then added dropwise. After one hour, additional 3-pyridinyl hydroximoyl chloride (5 mg) and triethylamine (5 μL) were added to the reaction and the mixture was stirred at room temperature overnight. The reaction mixture was diluted with ethyl acetate (10 mL) and washed sequentially with water then saturated potassium ferricyanide phosphate buffer (pH=7.4). The organic layer was dried over sodium sulfate and the purple residue purified on preparative thin layer chromatography plates (30% acetonitrile/chloroform) to give the title compound, 8.5 mg (66% yield). ESI MS m/z (M+H)+ 940.1; 1H NMR (400 MHz, CDCl3) δ 13.07 (s, 1H), 8.48 (d, J=4.7 Hz, 1H), 7.83 (d, J=7.8 Hz, 1H), 7.63 (dt, J=7.8, 1.6 Hz, 1H), 7.34 (s, 1H), 7.19-7.14 (m, 1H), 7.06 (dd, J=16.4, 11.0 Hz, 1H), 6.64 (s, 1H), 6.21 (d, J=10.2 Hz, 1H), 6.01 (dd, J=16.4, 6.3 Hz, 1H), 5.86 (dd, J=11.7, 1.6 Hz, 1H), 5.26 (app t, J=6.3 Hz, 1H), 4.88 (dd, J=12.5, 4.7 Hz, 1H), 4.84 (d, J=10.2 Hz, 1H), 4.40-4.33 (m, 2H), 3.78 (d, J=10.2 Hz, 1H), 3.74-3.68 (m, 2H), 3.60-3.49 (m, 2H), 3.40-3.32 (m, 2H), 3.19-3.10 (m, 2H), 2.99 (br d, J=10.2 Hz, 1H), 2.90 (s, 3H), 2.20-2.12 (m, 1H), 2.07 (s, 3H), 1.94 (s, 3H), 1.72-1.60 (m, 3H), 1.55 (s, 3H), 1.48-1.40 (m, 2H), 0.84 (d, J=7.0 Hz, 3H), 0.71 (d, J=7.0 Hz, 3H), 0.52 (d, J=7.0 Hz, 3H), 0.01 (d, J=7.0 Hz, 3H).

EXAMPLE 48

25-O-Desacetyl-(carbonyl-(3-acetyl-isoxazol-5-ylm-ethylamino) 3-morpholino rifamycin S

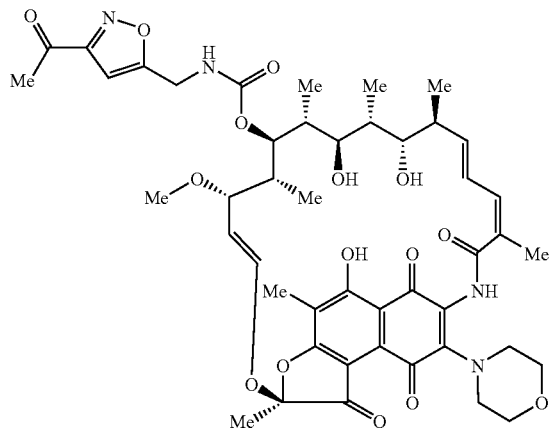

Acetyl hydroximoyl chloride (Kim, Jung, 1981) (5 mg, 0.04 mmol) was dissolved in anhydrous ethyl acetate (0.1 mL) at room temperature. To this solution was added sodium bicarbonate (17 mg, 0.20 mmol). The compound of Example 43 (31 mg, 0.04 mmol) in anhydrous ethyl acetate (0.6 mL) was then added dropwise. After one hour, additional acetyl hydroximoyl chloride (5 mg) and sodium bicarbonate (17 mg) was added to the reaction and the mixture allowed to stir at room temperature overnight. Upon consumption of starting material, the reaction was diluted with ethyl acetate (10 mL) and washed sequentially with water and a saturated potassium ferricyanide phosphate buffer (pH=7.4). The organic layer was dried over sodium sulfate and concentrated to a purple residue. Residue was purified on preparative thin layer chromatography plates (50% ethyl acetate/hexanes) to give the title compound, 10.9 mg (68% yield) as a 3:7 mixture of regioisomers. ESI MS m/z (M+H)+ 905.1; $^1$H NMR (400 MHz, CDCl$_3$) δ 13.07 (s, 1H, 7.34 (s, 1H), 7.01 (dd, J=15.7, 11.0 Hz, 1H), 6.35 (s, 1H), 6.20 (d, J=10.2 Hz, 1H), 6.00 (dd, J=15.7, 6.3 Hz, 1H), 5.87 (dd, J=12.5, 1.6 Hz, 1H), 5.19 (app t, J=6.3 Hz, 1H), 4.86 (dd, J=12.5, 5.5 Hz, 2H), 4.81 (d, J=10.2 Hz, 1H), 4.34 (dd, J=11.7, 6.3 Hz, 1H), 4.23 (d, J=3.9 Hz, 1H), 3.80-3.68 (m, 3H), 3.60-3.52 (m, 2H), 3.49 (s, 1H), 3.40-3.28 (m, 3H), 3.17-3.10 (m, 2H), 2.98-2.92 (m, 1H), 2.88 (s, 3H), 2.44 (s, 3H), 2.08 (s, 3H), 1.94 (s, 3H), 1.70-1.60 (m, 1H), 1.56 (s, 3H), 1.52-1.40 (m, 2H), 1.25 (s, 2H), 0.86 (d, J=7.0 Hz, 3H), 0.71 (d, J=7.0 Hz, 3H), 0.52 (d, J=7.0 Hz, 3H), 0.01 (d, J=7.0 Hz, 3H).

EXAMPLE 49

25-O-Desacetyl-(carbonyl-N-hydroxy-N'-phenyl-4-(2-piperazin-1-yl-ethylamino)-3-trifluoromethyl-benzamidine) 3-morpholino rifamycin S

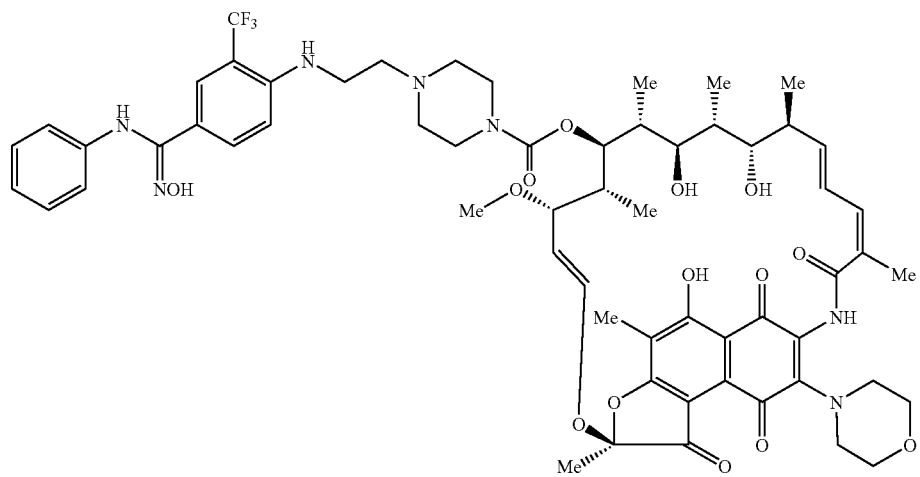

Synthesis: N-Hydroxy-N'-phenyl-4-(2-piperazin-1-yl-ethylamino)-3-trifluoromethyl-benzamidine was prepared as previous described (International Patent Application Publication No. WO 200/051456 A2) and reacted with the compound of Example 5, as described in Example 6, to give the title compound. $^1$H NMR (400 MHz, CD$_3$OD) δ 7.45 (d, J=2.3 Hz, 1H), 7.34 (dd, J=8.6, 1.6 Hz, 1H), 7.11 (t, J=7.8 Hz, 2H), 6.89 (t, J=7.8 Hz, 1H), 6.72 (t, J=7.8 Hz, 3H), 5.60 (app t, J=4.7 Hz, 1H), 3.24 (t, J=4.7 Hz, 2H), 2.84 (t, J=4.7 Hz, 4H), 2.63 (t, J=6.3 Hz, 2H), 2.47 (br s, 4H).

EXAMPLE 50

N-(2-Methyl-1H-indol-5-yl)-4-piperazin-1-yl-3-trifluoromethyl-benzamide

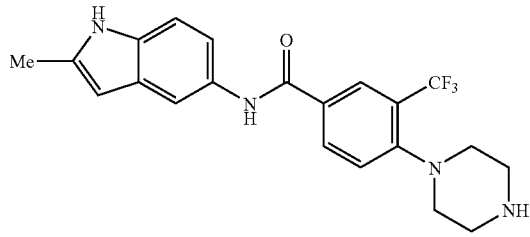

Synthesis: 4-Fluoro-3-trifluoromethyl benzoyl chloride (0.42 mL, 2.77 mmol) was added to a solution of 2-methyl-1H-indol-5-ylamine (472 mg, 3.23 mmol) and triethylamine (0.42 mL, 3.01 mmol) in anhydrous dichloromethane at room temperature. The reaction mixture was stirred at room temperature for two hours then diluted with a 1:1 mixture of ethyl acetate and water (80 mL). The organic layer was washed sequentially with 0.5N HCl, saturated NaHCO$_3$, water, saturated NaCl and dried over anhydrous sodium sulfate. The desired 4-fluoro-N-(2-methyl-1H-indol-5-yl)-3-trifluoromethyl-benzamide was obtained as a purple solid in nearly quantitative yield. This material was taken onto the next step without further purification. 4-Fluoro-N-(2-methyl-1H-indol-5-yl)-3-trifluoromethyl-benzamide (1.02 g, 3.03 mmol) and piperazine (1.83 g, 21.21 mmol) was dissolved in N,N-dimethylformamide (10 mL). The reaction mixture was heated in a sealed glass tube at 125° C. for two and a half hours. The crude mixture was then cooled to room temperature, concentrated and the residue chromatographed with 10% MeOH/CH$_2$Cl$_2$+2% triethylamine to afford N-(2-Methyl-1H-indol-5-yl)-4-piperazin-1-yl-3-trifluoromethyl-benzamide, the title compound (86% yield). $^1$H NMR (400 MHz, CD$_3$OD) δ 8.26 (d, J=2.3 Hz, 1H), 8.18 (dd, J=8.6, 2.3 Hz, 1H), 7.69 (d, J=1.6 Hz, 1H, 7.55 (d, J=8.6 Hz, 1H), 7.28-7.17 (m, 2H), 2.99 (s, 8H), 2.41 (s, 3H).

EXAMPLE 51

25-O-Desacetyl-(carbonyl-N-(2-methyl-1H-indol-5-yl)-4-piperazin-1-yl-3-trifluoromethyl-benzamide) 3-morpholino rifamycin S

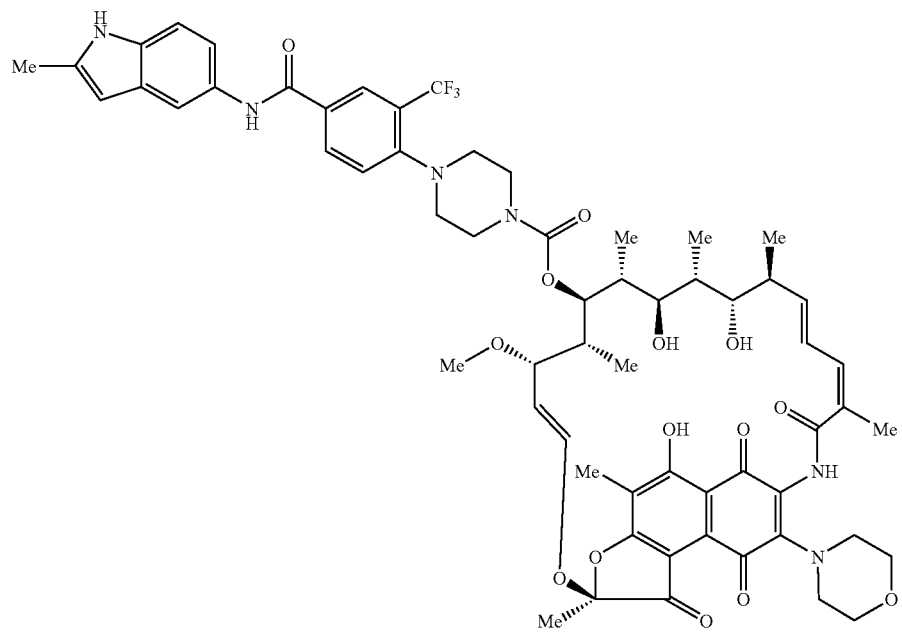

Synthesis: N-(2-Methyl-1H-indol-5-yl)-4-piperazin-1-yl-3-trifluoromethyl-benzamide was reacted with the compound of Example 5, as described in Example 6, to give the title compound. ESI MS m/z (M+H)+ 1167.1; $^1$H NMR (400 MHz, CDCl$_3$) δ 13.20 (s, 1H), 8.10 (s, 1H), 8.03-7.96 (m, 1H), 7.91 (s, 1H), 7.75 (d, J=16.4 Hz, 1H), 7.48 (s, 1H), 7.35 (s, 1H), 6.91 (s, 1H), 6.73 (dd, J=16.4, 11.0 Hz, 1H), 5.01 (dd, J=12.5, 4.7 Hz, 1H), 4.95 (s, 1H), 3.94-3.80 (m, 3H), 3.74-3.64 (m, 3H), 3.56 (br s, 1H), 3.52-3.44 (m, 3H), 3.32-3.22 (m, 3H), 3.09 (s, 3H), 2.86 (s, 4H), 2.38 (s, 3H), 2.35-2.22 (m, 1H), 2.20 (s, 3H), 2.05 (s, 3H), 1.68 (s, 3H), 1.62-1.59 (m, 1H), 1.36 (s, 8H), 1.01 (d, J=7.0 Hz, 3H), 0.90-0.72 (m, 8H), 0.66 (d, J=7.0 Hz, 3H), 0.17 (d, J=7.0 Hz, 3H).

EXAMPLE 52

N-(5-Methoxy-pyridin-3-yl)-4-piperazin-1-yl-3-trifluoromethyl-benzamide

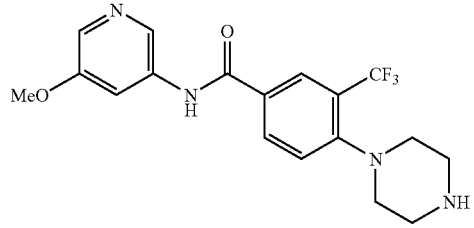

Synthesis: The title compound was prepared as described in Example 50, using 3-amino-5-methoxypyridine in place of 2-methyl-1H-indol-5-ylamine. $^1$H NMR (400 MHz, CD$_3$OD) δ 8.43 (d, J=2.3 Hz, 1H), 8.27 (d, J=1.6 Hz, 1H), 8.18 (dd, J=8.6, 3.1 Hz, 1H), 8.01 (dd, J=9.4, 3.1 Hz, 1H), 7.56 (d, J=8.6 Hz, 1H), 6.83 (d, J=9.4 Hz, 1H), 3.91 (s, 3H), 3.02 (s, 8H).

EXAMPLE 53

25-O-Desacetyl-(carbonyl-N-(5-methoxy-pyridin-3-yl)-4-piperazin-1-yl-3-trifluoromethyl-benzamide) 3-morpholino rifamycin S Synthesis: The compound of Example 5 was treated with N-(5-methoxy-pyridin-3-yl)-4-piperazin-1-yl-3-trifluoromethyl-benzamide, as described in Example 6, to give compound the title compound. ESI MS m/z (M+H)+ 1145.1; $^1$H NMR (400 MHz, CDCl$_3$) δ 13.20 (s, 1H), 8.22 (d, J=2.3 Hz, 1H), 8.10 (d, J=1.6 Hz, 1H), 8.00 (d, J=8.6 Hz, 1H), 7.95 (dd, J=8.6, 2.3 Hz, 1H), 7.85 (s, 1H), 7.48 (s, 1H), 7.28 (d, J=8.6 Hz, 1H), 6.91 (s, 1H), 6.72 (d, J=9.4 Hz, 1H), 5.01 (dd, J=11.7, 4.7 Hz, 1H), 4.96-4.94 (m, 2H), 4.80 (br s, 1H), 3.87 (s, 3H), 3.84-3.80 (m, 2H), 3.72-3.64 (m, 3H), 3.57 (br s, 4H), 3.52-3.43 (m, 3H), 3.08 (s, 3H), 2.86 (br s, 5H), 2.32-2.26 (m, 1H), 2.20 (s, 3H), 2.05 (s, 2H), 1.92-1.72 (m, 3H), 1.68 (s, 2H), 1.65-1.60 (m, 2H), 1.36 (s, 6H), 1.00 (d, J=7.0 Hz, 3H), 0.83 (d, J=7.0 Hz, 3H), 0.66 (d, J=7.0 Hz, 3H), 0.17 (d, J=7.0 Hz, 3H).

EXAMPLE 54

25-O-Desacetyl-(carbonyl-N-(4-piperidone)) cyclic-21,23-(1-methylethylidene acetal) 3-morpholino rifamycin S

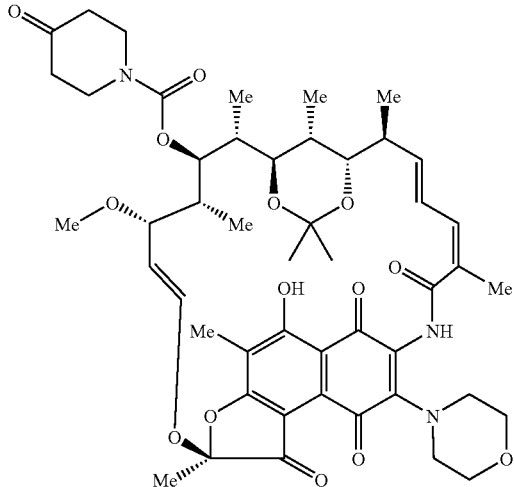

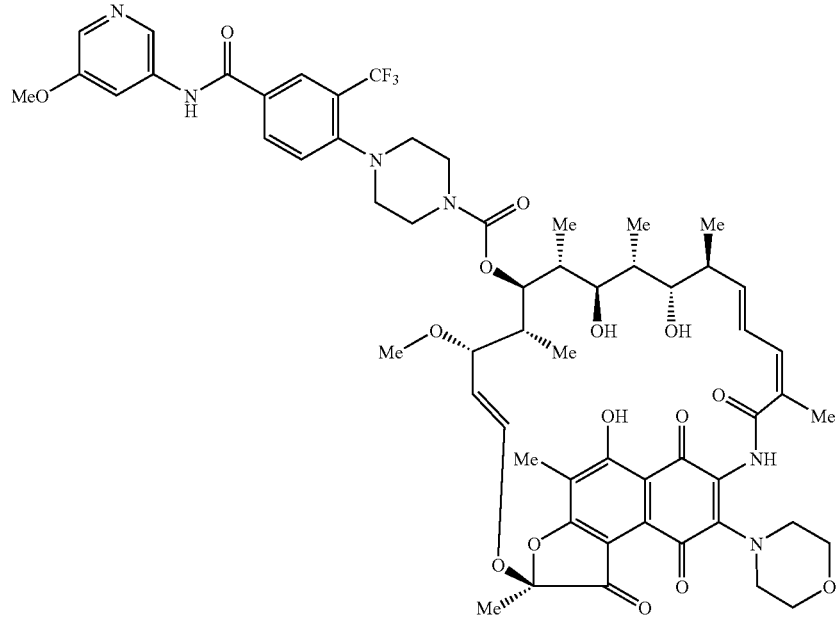

Synthesis: The compound of Example 5 was treated with 4-piperidone hydrochloride and N-methylmorpholine, as described in Example 6, to give compound the title compound. ESI MS m/z (M+H)+ 904.0.

EXAMPLE 55

25-O-Desacetyl-(carbonyl-N-(1-cyclopropyl-6-fluoro-8-methoxy-7-(octahydro-pyrrolo[3,4-b]pyridin-6-yl)-4-oxo-1,4-dihydro-quinoline-3-carboxylic acid) 3-morpholino rifamycin S Synthesis: The compound of Example 54 (100 mg, 0.11 mmol) was treated with 1-cyclopropyl-6-fluoro-8-methoxy-7-(octahydro-pyrrolo[3,4-b]pyridin-6-yl)-4-oxo-1,4-dihydro-quinoline-3-carboxylic acid (53 mg, 0.12 mmol) and NaBH(OAc)$_4$ (70 mg, 0.33 mmol) and stirred at 23° C. for 6 hr the mixture is diluted with ethyl acetate and washed with water. The ethyl acetate layer is washed with a dilute K$_3$Fe(CN)$_6$ in pH 7.4 phosphate buffer. The residue is purified by preparative TLC and the product dissolved in THF and treated with 1 N HCl (aq) to remove the acetonide and give compound the title compound. ESI MS m/z (M+H)+ 1249.38.

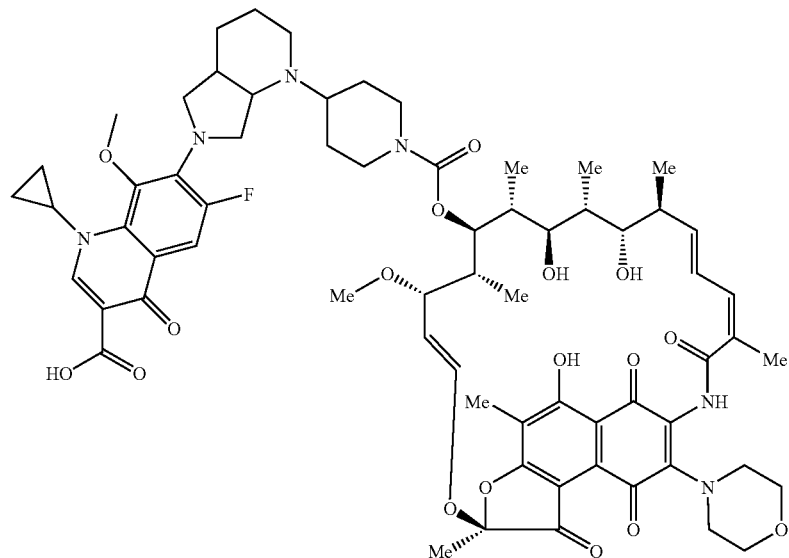

EXAMPLE 56

25-O-Desacetyl-(carbonyl-N-(7-(3-amino-pyrrolidin-1-yl)-1-cyclopropyl-6-fluoro-8-methoxy-4-oxo-1,4-dihydro-quinoline-3-carboxylic acid) 3-morpholino rifamycin S

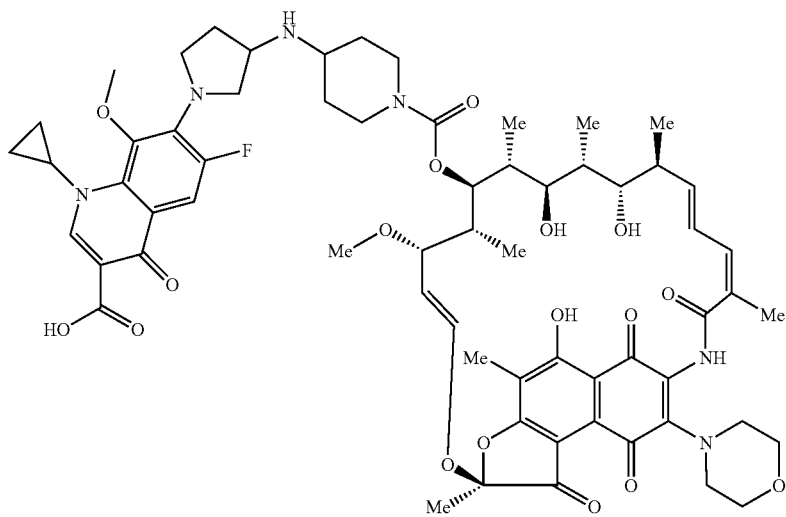

Synthesis: The compound of Example 56 was prepared as described for Example 55 using 7-(3-amino-pyrrolidin-1-yl)-1-cyclopropyl-6-fluoro-8-methoxy-4-oxo-1,4-dihydro-quinoline-3-carboxylic acid; ESI MS m/z (M+H)+ 1209.3.

EXAMPLE 57

25-O-Desacetyl-(carbonyl-N-(1-cyclopropyl-6-fluoro-4-oxo-7-piperazin-1-yl-1,4-dihydro-quinoline-3-carboxylic acid) 3-morpholino rifamycin S Synthesis: The compound of Example 57 was prepared as described for Example 55 using 1-cyclopropyl-6-fluoro-4-oxo-7-piperazin-1-yl-1,4-dihydro-quinoline-3-carboxylic acid; ESI MS m/z (M+H)+ 1179.3.

EXAMPLE 58

25-O-Desacetyl-(carbonyl-N-(7-(4-amino-piperidin-1-yl)-1-cyclopropyl-6-fluoro-8-methoxy-4-oxo-1,4-dihydro-quinoline-3-carboxylic acid) 3-morpholino rifamycin S

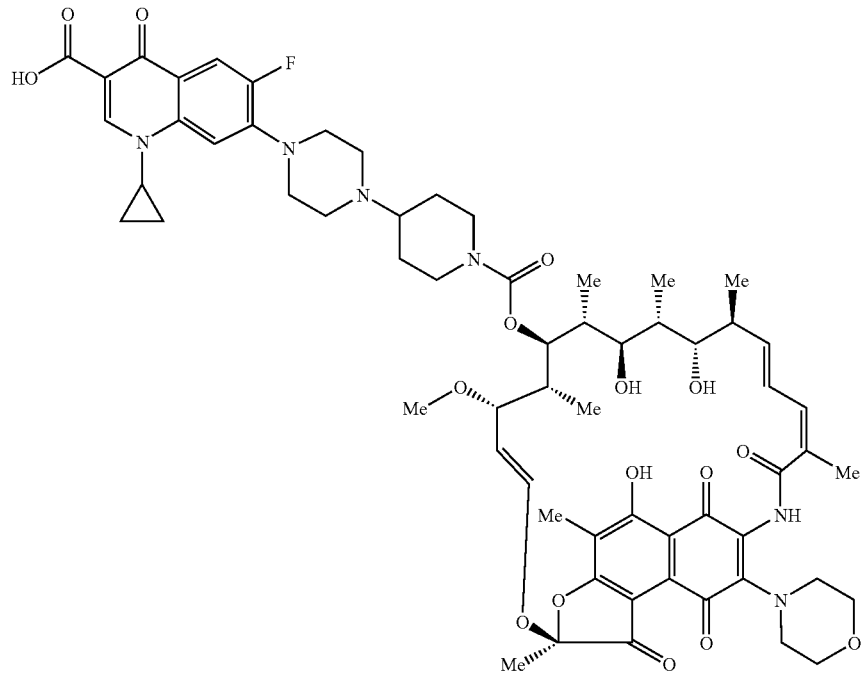

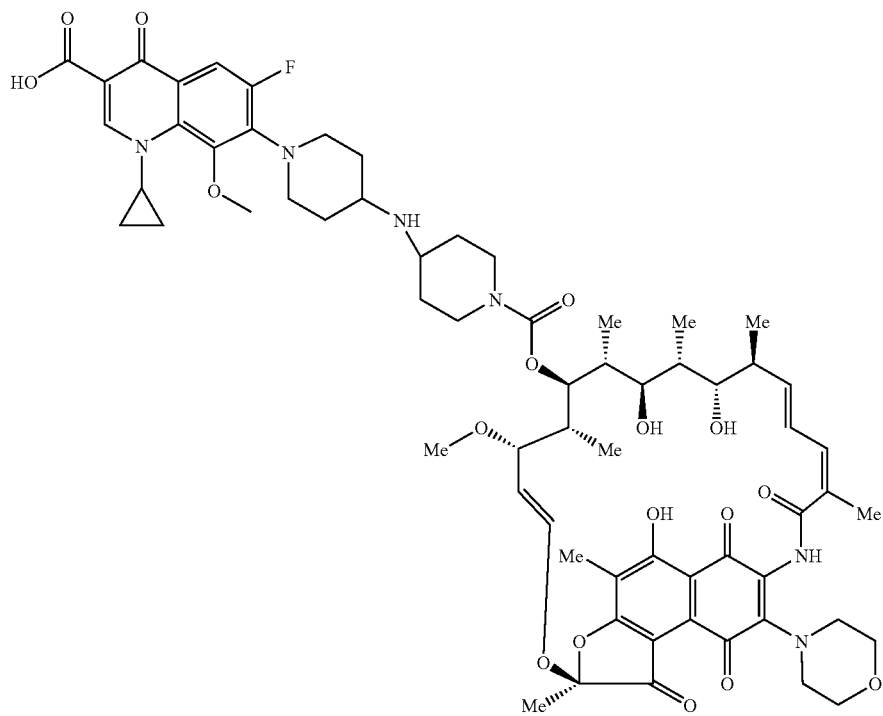

Synthesis: The compound of Example 58 was prepared as described for Example 55 using 7-(4-amino-piperidin-1-yl)-1-cyclopropyl-6-fluoro-8-methoxy-4-oxo-1,4-dihydro-quinoline-3-carboxylic acid; ESI MS m/z (M+H)$^+$ 1223.3.

EXAMPLE 59

25-O-Desacetyl-(carbonyl-N-(7-(3-amino-piperidin-1-yl)-1-cyclopropyl-6-fluoro-8-methoxy-4-oxo-1,4-dihydro-quinoline-3-carboxylic acid) 3-morpholino rifamycin S Synthesis: The compound of Example 59 was prepared as described for Example 55 using 7-(3-amino-piperidin-1-yl)-1-cyclopropyl-6-fluoro-8-methoxy-4-oxo-1,4-dihydro-quinoline-3-carboxylic acid; ESI MS m/z (M+H)$^+$ 1223.3.

EXAMPLE 60

25-O-Desacetyl-(carbonyl-N-(1-cyclopropyl-6-fluoro-8-methoxy-4-oxo-7-piperazin-1-yl-1,4-dihydro-quinoline-3-carboxylic acid) 3-morpholino rifamycin S

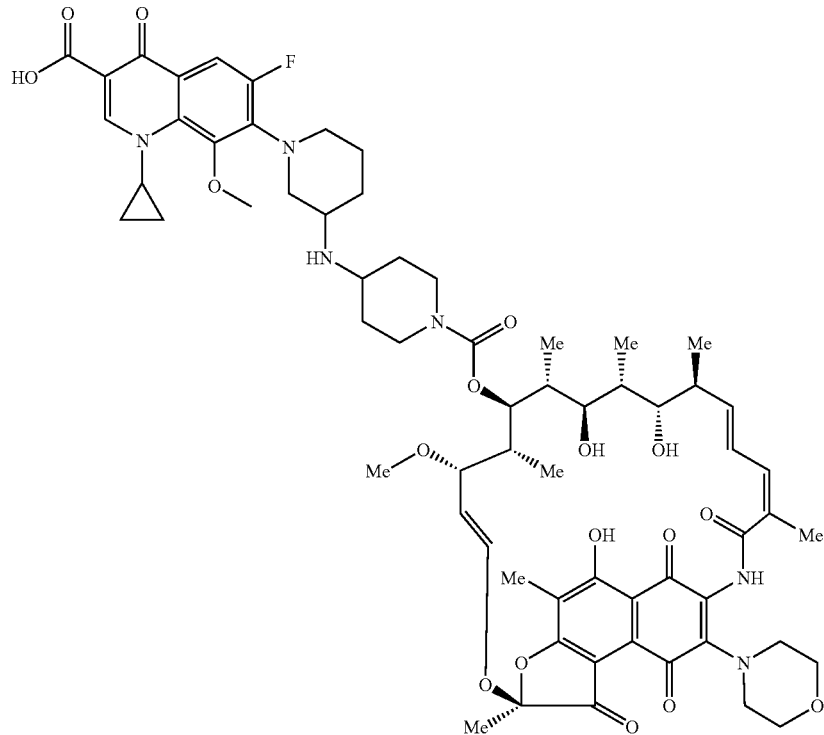

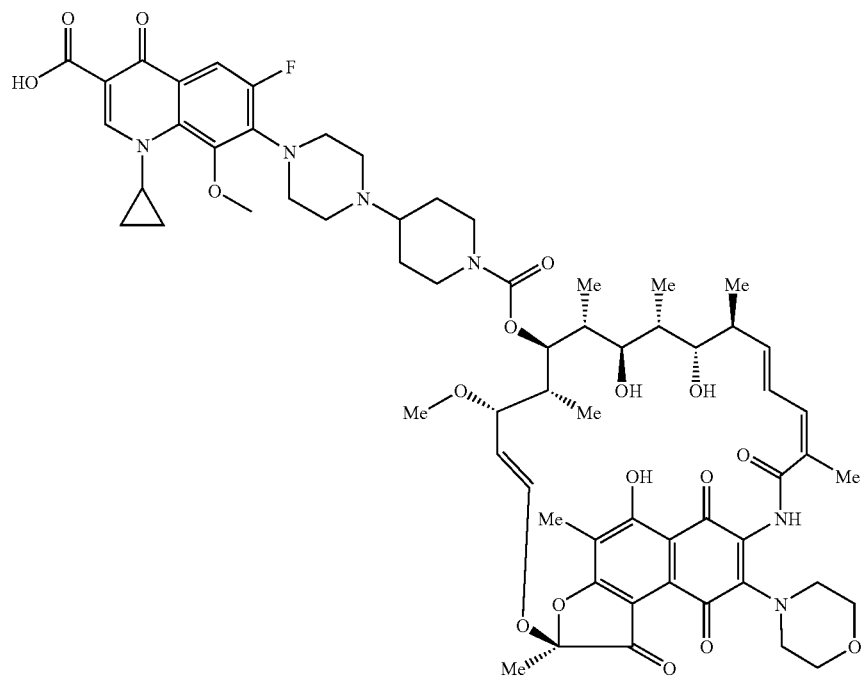

Synthesis: The compound of Example 60 was prepared as described for Example 55 using 1-cyclopropyl-6-fluoro-8-methoxy-4-oxo-7-piperazin-1-yl-1,4-dihydro-quinoline-3-carboxylic acid; ESI MS m/z (M+H)+ 1209.3.

EXAMPLE 61

25-O-Desacetyl-(carbonyl-N-(3-pyrrolidone) cyclic-21,23-(1-methylethylidene acetal)-3-morpholino rifamycin S

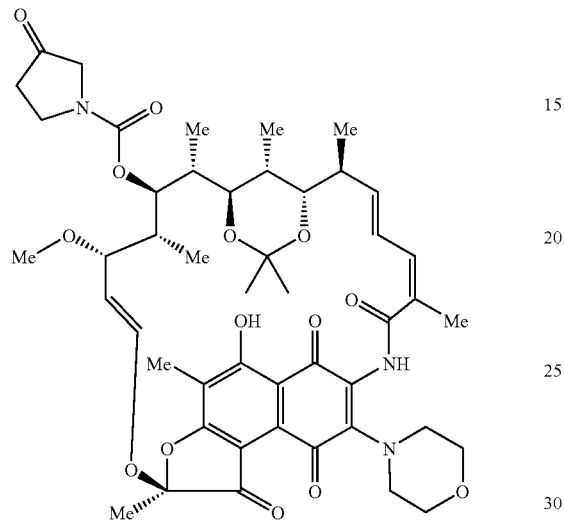

Synthesis: The compound of Example 5 was treated with 3-pyrrolidinone hydrochloride and N-methylmorpholine, as described in Example 6, to give compound the title compound. ESI MS m/z (M+H)+ 889.9.

EXAMPLE 62

25-O-Desacetyl-(carbonyl-N-(1-cyclopropyl-6-fluoro-8-methoxy-4-oxo-7-(4-pyrrolidin-3-yl-piperazin-1-yl)-1,4-dihydro-quinoline-3-carboxylic acid) 3-morpholino rifamycin S

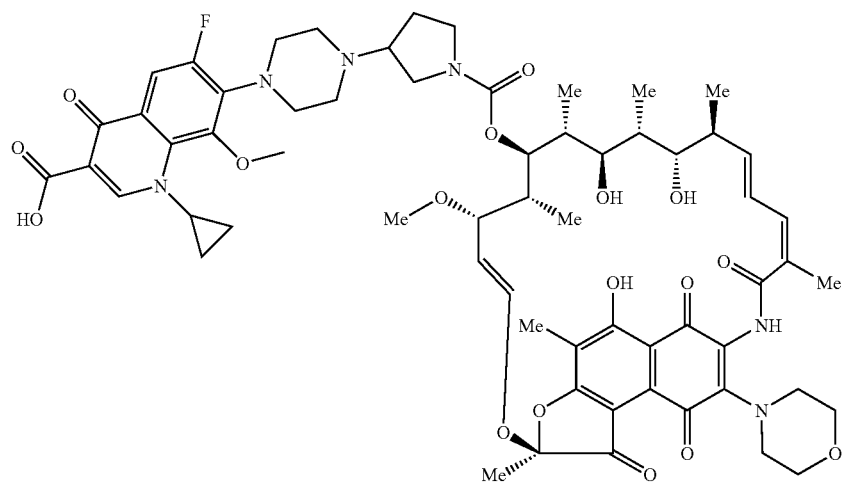

Synthesis: The compound of Example 62 was prepared as described for Example 55 using 1-cyclopropyl-6-fluoro-8-methoxy-4-oxo-7-piperazin-1-yl-1,4-dihydro-quinoline-3-carboxylic acid; ESI MS m/z (M+H)+ 1195.3.

EXAMPLE 63

25-O-Desacetyl-(carbonyl-N-(7-[3-(2-amino-acetylamino)-pyrrolidin-1-yl]-8-chloro-1-cyclopropyl-6-fluoro-4-oxo-1,4-dihydro-quinoline-3-carboxylic acid 3-morpholino rifamycin S

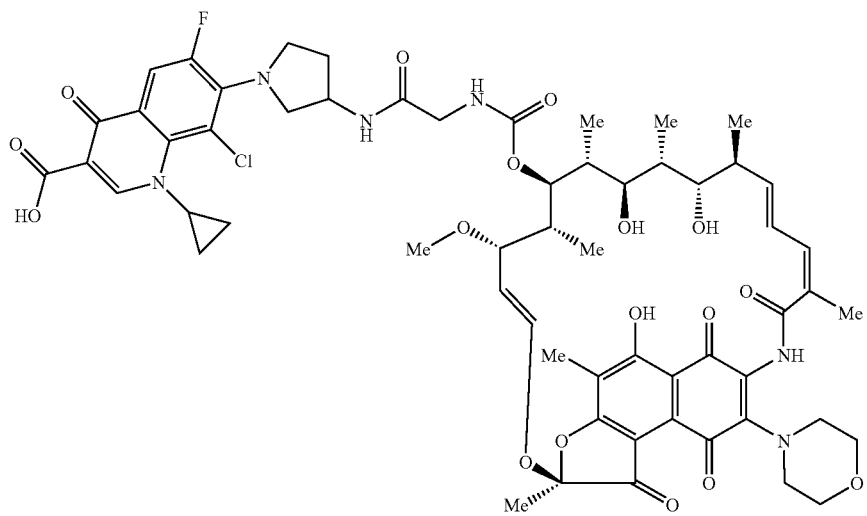

Synthesis: The compound of Example 5 (125 mg, 0.13 mmol) was dissolved in methylene chloride (3 ml) and treated with tert-Butoxycarbonylamino-acetic acid ethyl ester (75 mg, 0.39 mmol) and N-methylmorpholine (42 ul, 0.39 mmol). The resulting solution was stirred at room temperature for 30 minutes. The reaction mixture was diluted with ethyl acetate (10 ml) and washed with 1 M aqueous citric acid (10 ml) followed by washing with saturated sodium chloride (10 ml). The resulting solution was dried with sodium sulfate, filtered, and evaporated to produce a dark solid. This residue was taken up in 1:4 (V/V) 1 M NaOH/tetrahydrofuran (5 ml) and stirred for 3 hours. After which the mixture was neutralized with 1 M citric acid and diluted with ethyl acetate and the aqueous layer was removed. The resulting solution was dried with sodium sulfate, filtered, and evaporated to produce a dark solid. This residue was taken up in DMF (3.0 ml) and to this solution was added EDCI (42 mg, 0.22 mmol), N-O-hydroxysuccinimide (25 mg, 0.22 mmol), and dimethylaminopyridine (3 mg, 0.022 mmol). The resulting solution was stirred for 3.5 hours. At which time water (10 ml) was added. The resulting precipitate was filted and washed with water. The collected solid was dissolved in methylene chloride, dried with MgSO4, and evaporated to yield a dark solid. This residue was taken up in methylene chloride (3 ml). To this solution was added 7-(3-amino-pyrrolidin-1-yl)-8-chloro-1-cyclopropyl-6-fluoro-4-oxo-1,4-dihydro-quinoline-3-carboxylic acid (70 mg). The resulting solution was stirred for 2 hours. After which the solution was washed with water (2×2 ml), dried with MgSO4, and evaporated to a dark solid. This residue was taken up in 1:2 (V/V) 1 M aqueous HCl/tetrahydrofuran (1 ml) and stirred for 3 hours. After which time the mixture was diluted with ethyl acetate (3 ml) and the aqueous layer was removed. This solution was vigorously washed with an aqueous solution consisting of 5% (W/V) potassium ferricyanide and 5% (W/V) sodium bicarbonate, which was then followed by multiple washes with saturated sodium chloride. The resulting solution was dried with sodium sulfate, filtered, and evaporated to produce the crude product. The crude mixture was purified on silica by preparatory TLC with 5% methanol/95% dichloromethane to produce the title compound, 9 mg. ESI MS m/z (M+H)+ 1187, (M+H—OCH3)+ 1155.

EXAMPLE 64

25-O-Desacetyl-(carbonyl-N-(7-[4-(2-amino-acetyl)-piperazin-1-yl]-1-cyclopropyl-6-fluoro-8-methoxy-4-oxo-1,4-dihydro-quinoline-3-carboxylic acid 3-morpholino rifamycin S

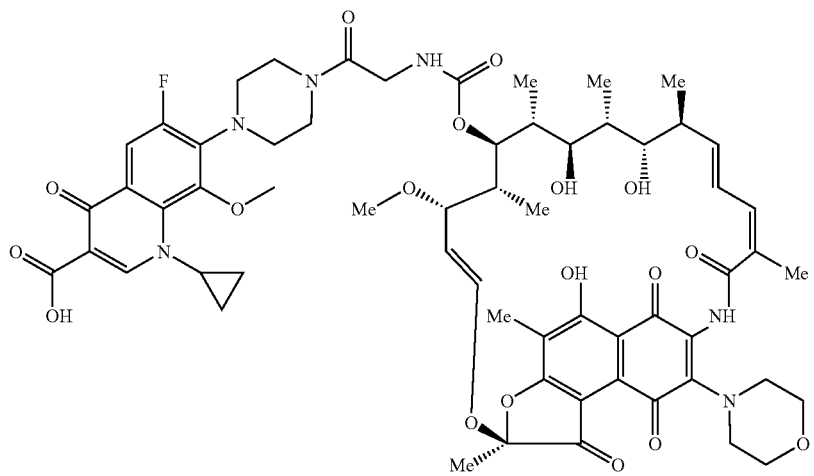

Synthesis: The title compound was prepared as described in Example 63 above, using 1-cyclopropyl-6-fluoro-8-methoxy-4-oxo-7-piperazin-1-yl-1,4-dihydro-quinoline-3-carboxylic acid in place of 7-(3-amino-pyrrolidin-1-yl)-8-chloro-1-cyclopropyl-6-fluoro-4-oxo-1,4-dihydro-quinoline-3-carboxylic acid. ESI MS m/z (M+H)$^+$ 1182, (M+H—OCH$^3$)$^+$ 1150.

EXAMPLE 65

25-O-Desacetyl-(carbonyl-N-(7-[4-(Azetidine-3-carbonyl)-3-methyl-piperazin-1-yl]-1-cyclopropyl-6-fluoro-8-methoxy-4-oxo-1,4-dihydro-quinoline-3-carboxylic acid) 3-morpholino rifamycin S Synthesis: The title compound was prepared as described in Example 63 above, using azetidine-1,3-dicarboxylic acid 1-tert-butyl ester 3-methyl ester in place of tert-butoxycarbonylamino-acetic acid methyl ester and using 1-cyclopropyl-6-fluoro-8-methoxy-7-(3-methyl-piperazin-1-yl)-4-oxo-1,4-dihydro-quinoline-3-carboxylic acid in place of 7-(3-amino-pyrrolidin-1-yl)-8-chloro-1-cyclopropyl-6-fluoro-4-oxo-1,4-dihydro-quinoline-3-carboxylic acid. ESI MS m/z (M+Na)$^+$ 1245, (M+H—OCH$_3$)$^+$ 1191.

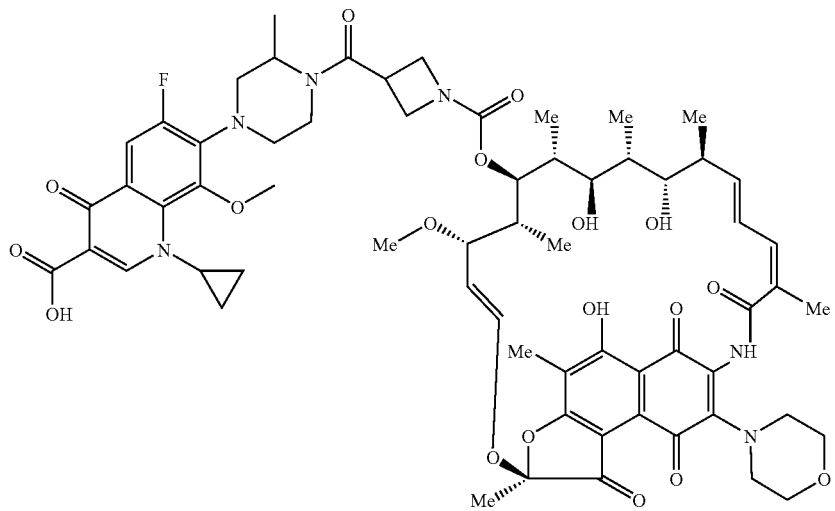

EXAMPLE 66

25-O-Desacetyl-(carbonyl-N-(7-[4-(azetidine-3-carbonyl)-piperazin-1-yl]-1-cyclopropyl-6-fluoro-8-methoxy-4-oxo-1,4-dihydro-quinoline-3-carboxylic acid) 3-morpholino rifamycin S

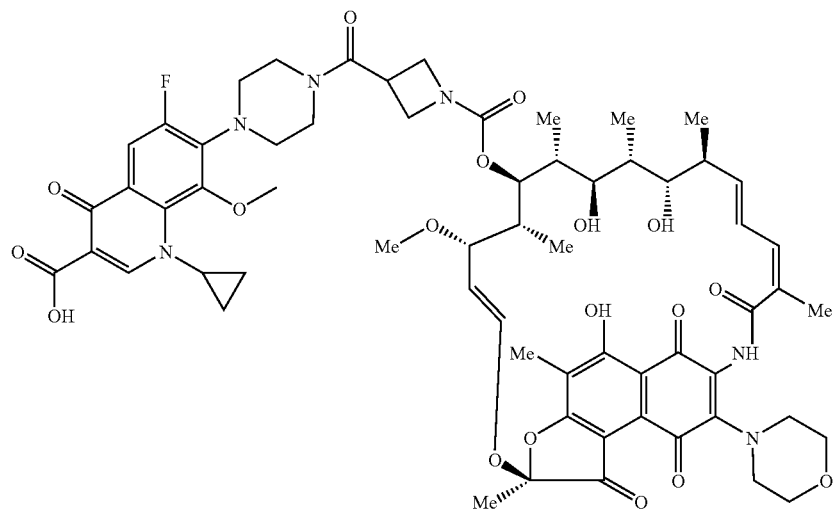

Synthesis: The title compound was prepared as described in example 63 above, using azetidine-1,3-dicarboxylic acid 1-tert-butyl ester 3-methyl ester in place of tert-butoxycarbonylamino-acetic acid methyl ester and using 1-cyclopropyl-6-fluoro-8-methoxy-4-oxo-7-piperazin-1-yl-1,4-dihydro-quinoline-3-carboxylic acid in place of 7-(3-amino-pyrrolidin-1-yl)-8-chloro-1-cyclopropyl-6-fluoro-4-oxo-1,4-dihydro-quinoline-3-carboxylic acid. ESI MS m/z (M+H)$^+$ 1209; (M+Na)$^+$ 1231, (M+H—OCH$_3$)$^+$ 1177.

EXAMPLE 67

25-O-Desacetyl-(carbonyl-N-7-(3-amino-pyrrolidin-1-yl)-8-chloro-1-cyclopropyl-6-fluoro-4-oxo-1,4-dihydro-quinoline-3-carboxylic acid) 3-morpholino rifamycin S Synthesis: The compound of Example 62 was prepared as described for Example 55 using 7-(3-amino-pyrrolidin-1-yl)-8-chloro-1-cyclopropyl-6-fluoro-4-oxo-1,4-dihydro-quinoline-3-carboxylic acid; ESI MS m/z (M+H)$^+$ 1130.2.

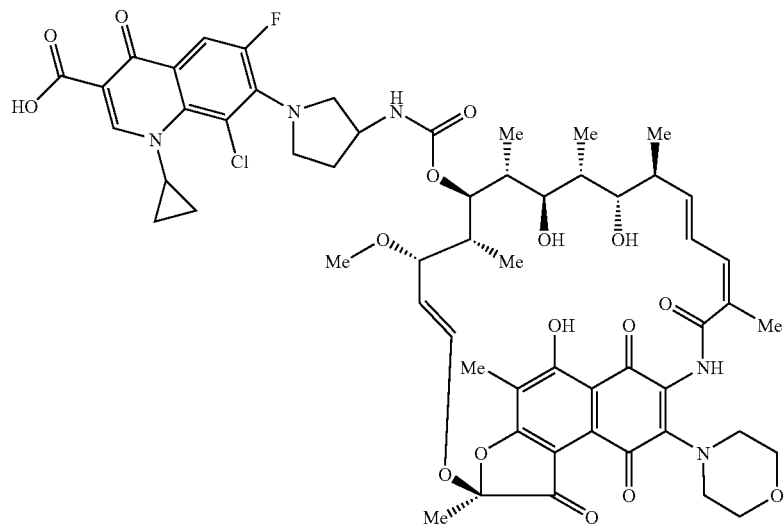

EXAMPLE 68

25-O-Desacetyl-(carbonyl-N-(8-chloro-1-cyclopropyl-6-fluoro-7-(3-formylamino-pyrrolidin-1-yl)-4-oxo-1,4-dihydro-quinoline-3-carboxylic acid)-3-morpholino-11-deoxy-11-hydroxyiminorifamycin S

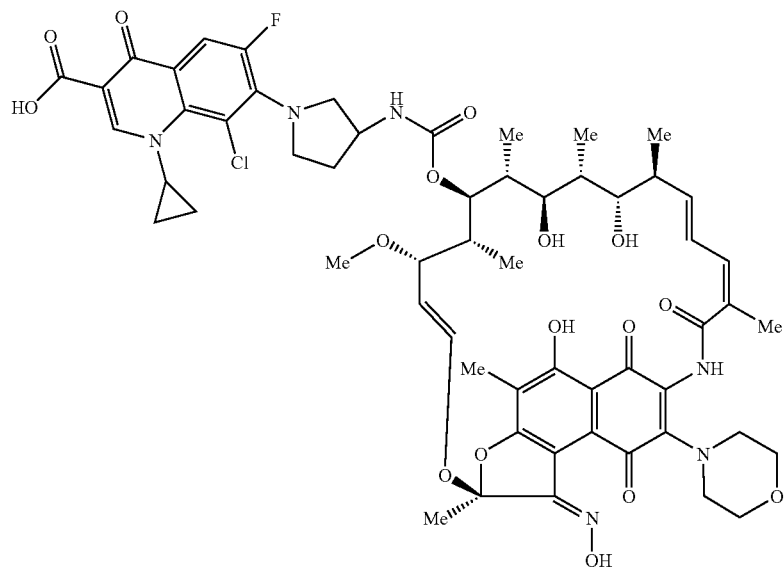

Synthesis: To a stirred solution of example 67 (1 eq) in MeOH and THF was added pyridine (13 eq) and hydroxylamine hydrochloride (13 eq). The reaction solution was allowed to stir 5 days at room temperature. The reaction mixture was purified by preparative thin layer chromatography (10% MeOH/DCM) to give the title compound as a purple-brown solid. ESI MS m/z 1145.63 $(M+H)^+$.

EXAMPLE 69

25-O-Desacetyl-(carbonyl-N-(2-dimethylaminoethyl)-3-morpholino-11-deoxy-11-hydroxyiminorifamycin S

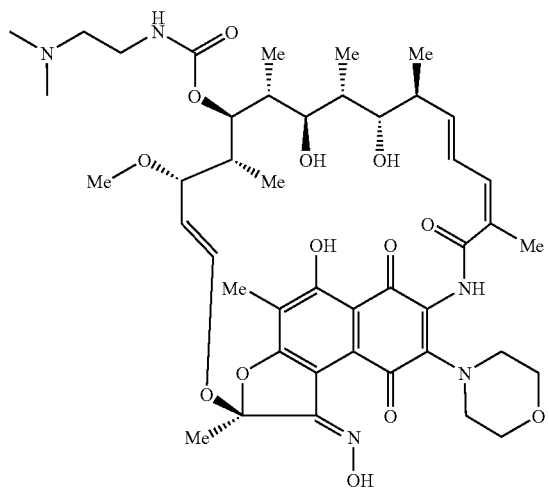

Synthesis: To a stirred solution of example 30 (1 eq) in MeOH and THF was added pyridine (13 eq) and hydroxylamine hydrochloride (13 eq). The reaction solution was allowed to stir 5 days at room temperature. The reaction mixture was purified by preparative thin layer chromatography (10% MeOH/DCM) to give the title compound as a purple-brown solid. ESI MS m/z 867.9 $(M+H)^+$.

REFERENCES CITED

The content of each of the following documents is hereby incorporated by reference.

U.S. Patent Documents

U.S. Pat. No. 4,188,321
U.S. Pat. No. 5,786,350

Other Patent Documents

International Patent Application Publication No. WO 01/051456 A2
International Patent Application Publication No. WO 03/045319 A2

Other Publications

Brufani, M., Cerrini, S., Fedeli, W., Vaciago, A. *J Mol. Biol.* 1974, vol. 87, pp. 409-35.
Farr, B. M. *Rifamycins*, in *Principles and Practice of Infectious Diseases*; Mandell, G. L., Bennett, J. E., Dolin, R., Eds.; Churchhill Livingstone: Philadelphia, pp. 348-361.
Greene, T. H. and Wuts, P. G. M., *Protective Groups in Organic Synthesis,* 2nd edition, John Wiley & Sons, New York, 1991.

Ince & Hooper, *Antimicrobial Agents and Chemotherapy*, 2000, vol. 44, pp. 3344-50.

Kim, Y. H., Jung, S. H., *Tet. Lett.*, vol. 22(25), pp. 2371-2, 1981.

Kocevar, M., et al., *Syn. Comm.*, vol. 18(12), pp. 1427-32, 1988.

Kump and Bickel, *Helv. Chim. Acta.*, 1973, vol. 56(7), pp. 2323-47.

National Committee for Clinical Laboratory Standards, 2000, Methods for dilution antimicrobial susceptibility tests for bacteria that grow aerobically, 5th ed. M7-A5, Wayne, Pa.

Wehrli, Zimmerman, et al. *Journal of Antibiotics*, 1987, vol. 40(12), pp. 1733-39.

Zamponi, G. W., et al. *J of Med. Chem.*, vol. 46(1), pp. 87-96, 2003.

What is claimed is:

1. A compound having a structural formula I:

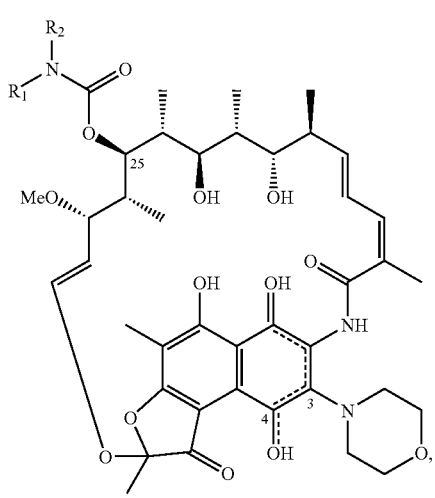

or its pharmaceutically acceptable salt thereof, wherein, $R_1$ and $R_2$ independently are hydrogen, $(C_1-C_6)$alkyl, $(C_1-C_6)$alkenyl, $(C_1-C_6)$alkynyl, or $R_1$ and $R_2$, together with the nitrogen atom to which they are attached, form a 4- to 8- membered heterocyclic ring containing zero or one additional nitrogen, oxygen, sulfur, or $S(=O)_2$, wherein the carbon or nitrogen atoms of the ring are substituted with zero or one $(C_1-C_6)$alkyl, $(C_1-C_6)$alkylamino, di$(C_1-C_6)$alkylamino, $(C_1-C_6)$alkoxy, or $R_1$ is H and $R_2$; is $L_{25}$-$Q_{25}$, wherein $L_{25}$ is one of the structural groups:

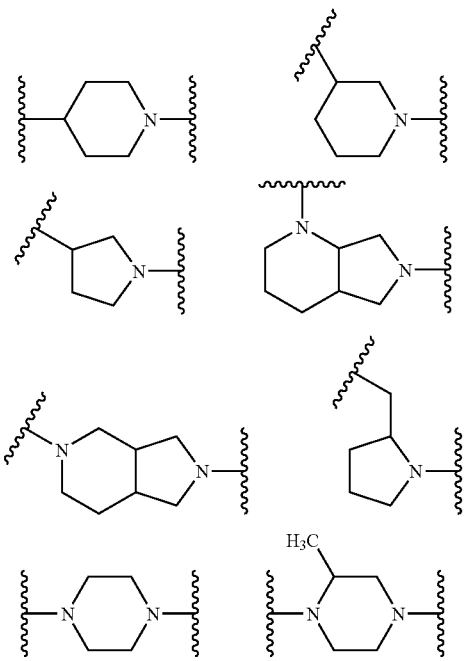

and wherein $Q_{25}$ is one of the structural groups:

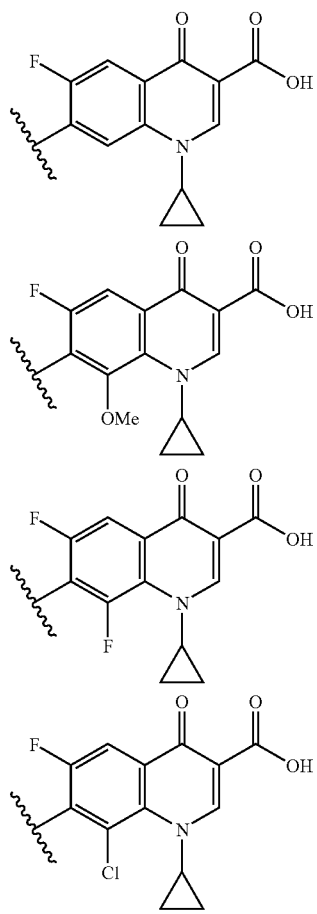

-continued
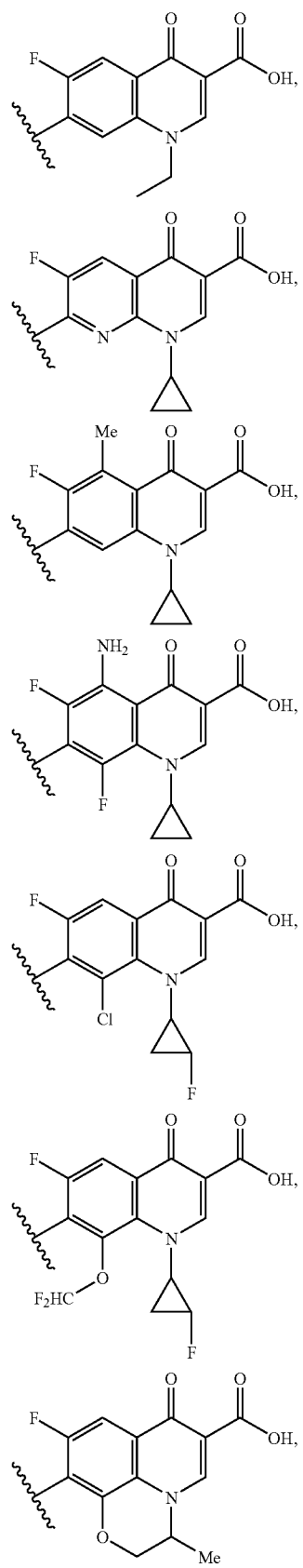
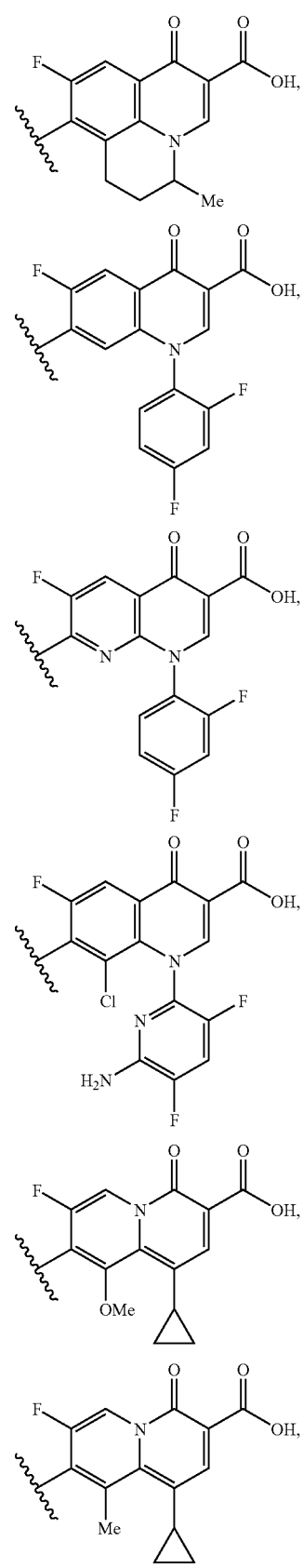

-continued

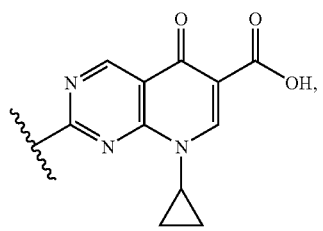

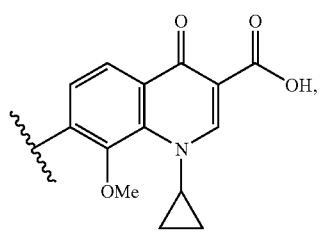

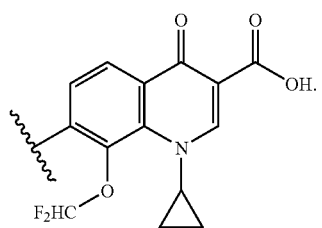

2. The compound of claim 1, wherein the structural formula is:

(a) 25-O-deacetyl-21,23-O-(1-methylethylidene)-3-(4-morpholinyl)-1,4-dioxo-25-O-[[3-(phenylmethyl)-1H-imidazolium-1-yl]carbonyl]-rifamycin S, bromide:

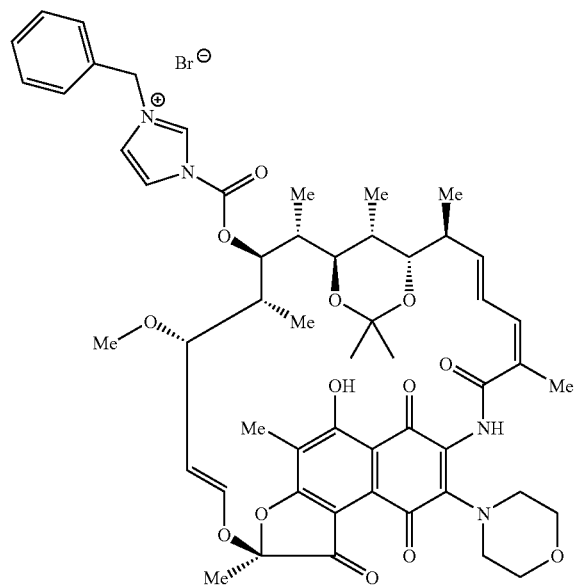

(b) 25-O-Desacetyl-N-(1-carbonyl-4-methyl-piperazine) 3-morpholino rifamycin S:

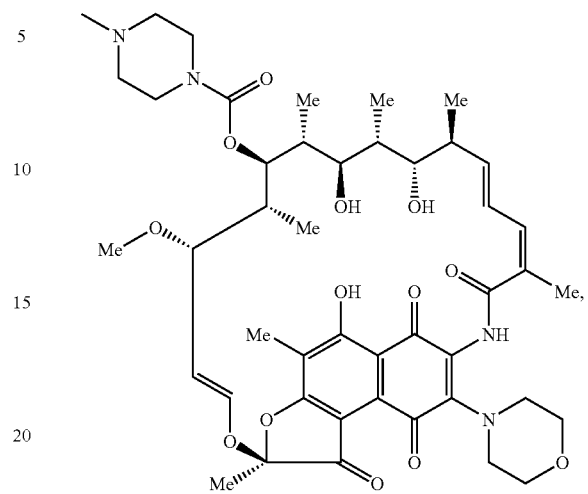

(c) 25-O-Desacetyl-(1-carbonyl-isobutylamino) 3-morpholino rifamycin S:

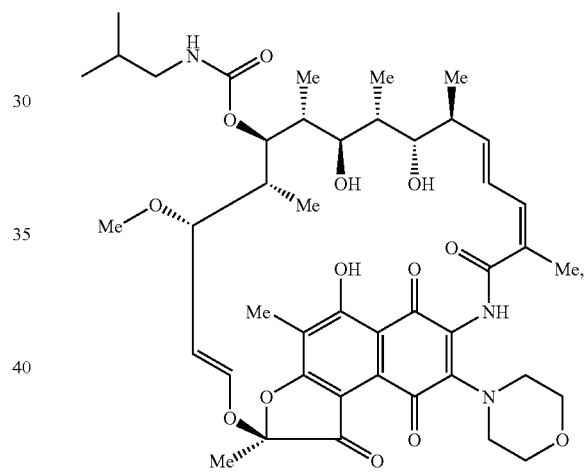

(d) 25-O-Desacetyl-(1-carbonyl-N-allylamino) 3-morpholino rifamycin S:

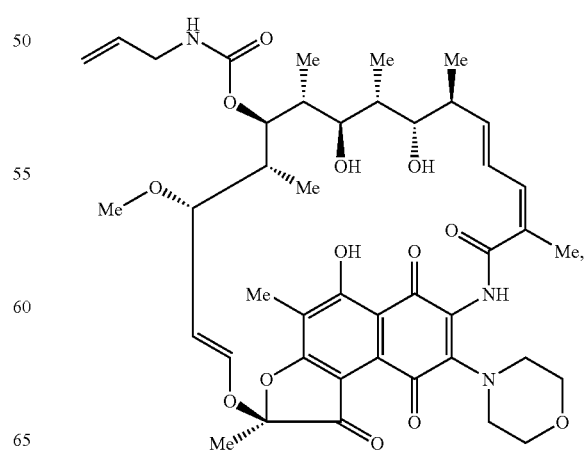

(e) 25-O-Desacetyl-1-carbonyl-N-[2-(4-methyl-piperazin-1-yl)-ethylamine] 3-morpholino rifamycin S:
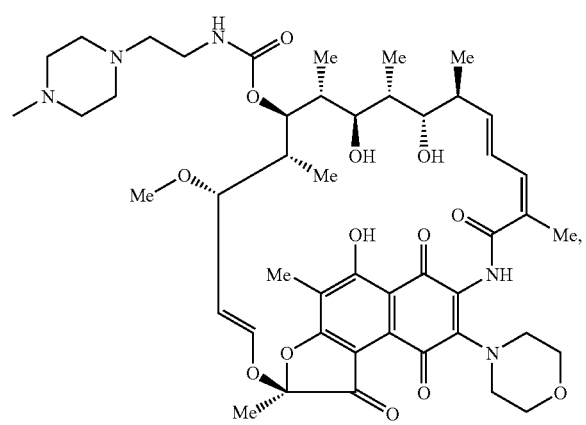
(f) 25-O-Desacetyl-1-carbonyl-N-diethylamine 3-morpholino rifamycin S:
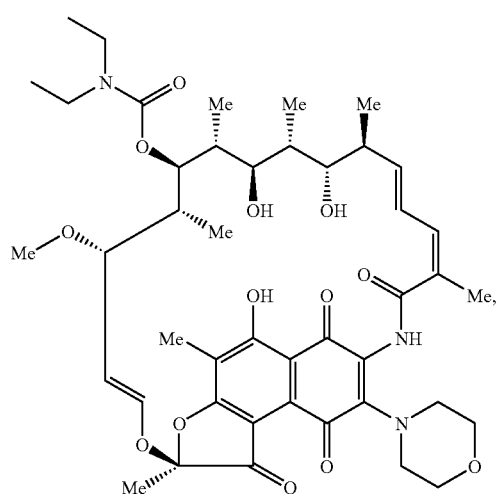
(g) 25-O-Desacetyl-1-carbonyl-N-[3-imidazol-1-yl-propylamine] 3-morpholino rifamycin S:
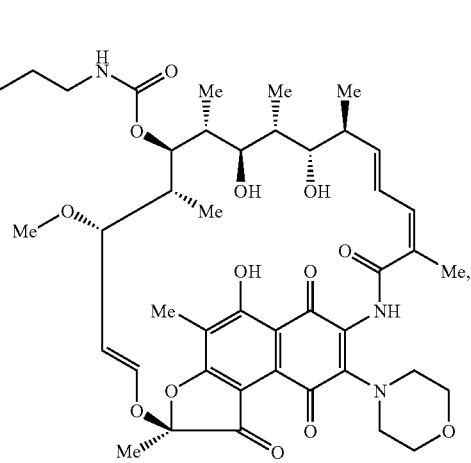
(h) 25-O-Desacetyl-1-carbonyl-N-[1-(4-fluorophenyl)-piperazine] 3-morpholino rifamycin S:
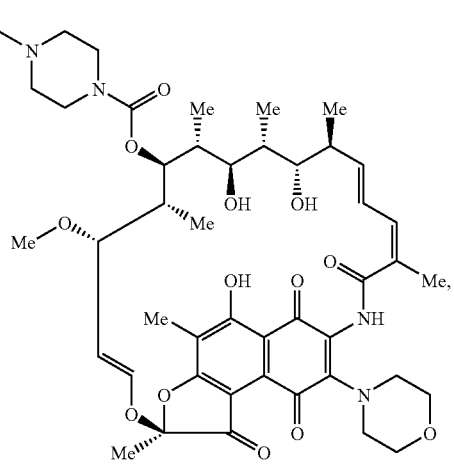

(i) 25-O-Desacetyl-1-[(3-trifluoromethylbenzylamino) carbonyl]-3-morpholino rifamycin S:
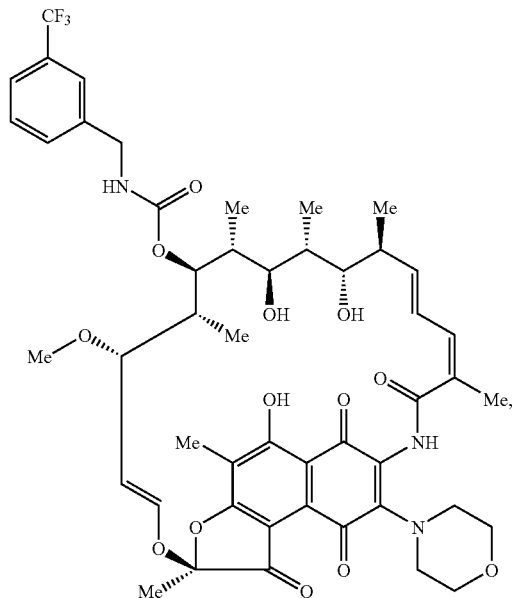
(k) 25-O-Desacetyl 1-carbonyl-N-benzyl 3-morpholino rifamycin S:
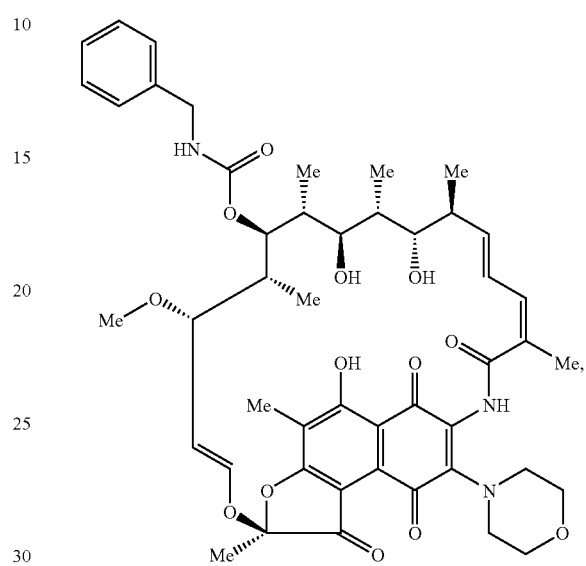
(j) 25-O-Desacetyl-(carbonyl-1-pyrrolidino) 3-morpholino rifamycin S:
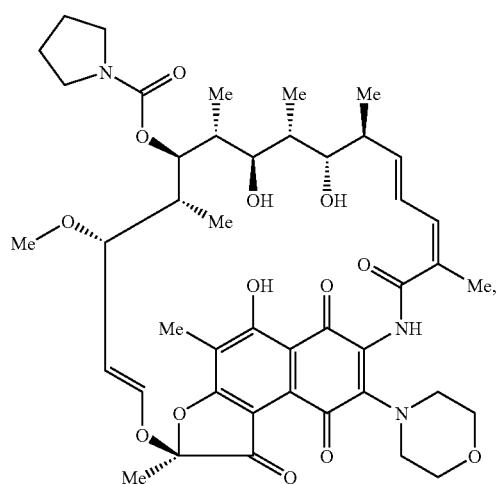
(l) 25-O-Desacetyl-4-carbonyl-N-[1-cyclopropyl-6-fluoro-4-oxo-7-piperazin-1-yl-1,4-dihydro-quinoline-3-carboxylic acid] 3-morpholino rifamycin S:
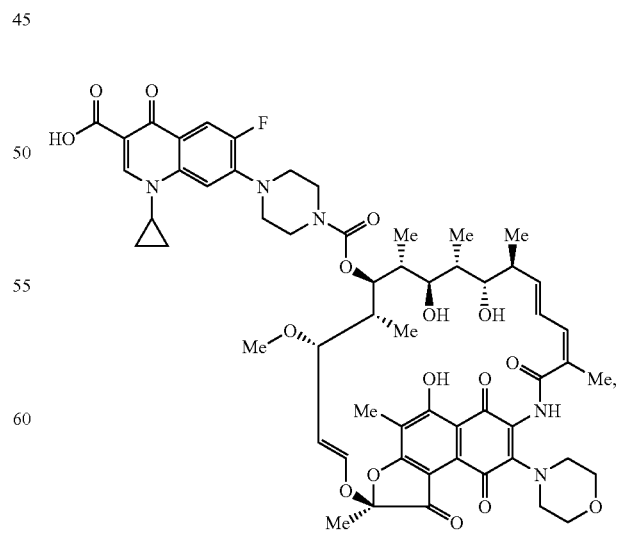

(m) 25-O-Desacetyl-1-carbonyl-N-[8-chloro-1-cyclopropyl-7-[4-(1-carbonyl)-piperazin-1-yl]-6-fluoro-4-oxo-1,4-dihydro-quinoline-3-carboxylic acid] 3-morpholino rifamycin S:

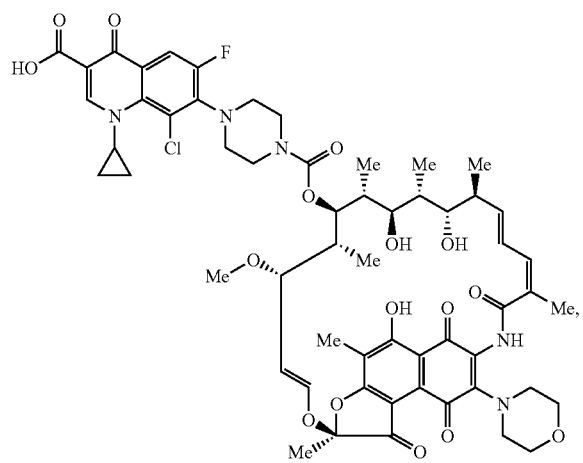

(n) 25-O-Desacetyl-1-carbonyl-N-[(2-pyridin-2-yl-ethylamine)] 3-morpholino rifamycin S:

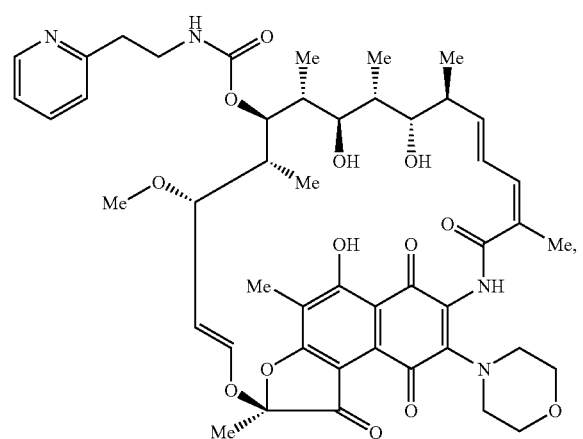

(o) 25-O-Desacetyl-1-carbonyl-N-[2-thiophen-2-yl-ethylamine] 3-morpholino rifamycin S:

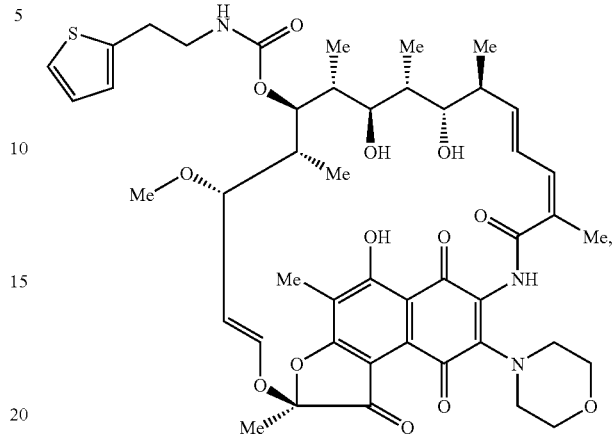

(p) 25-O-Desacetyl-1-carbonyl-N-[2-aminoethanol] 3-morpholino rifamycin S:

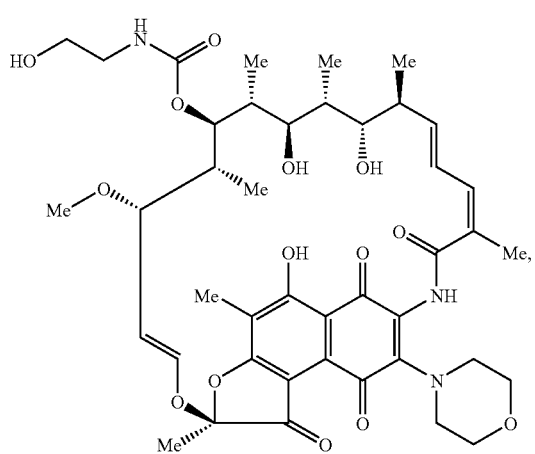

(q) 25-(O-Desacetyl-1-carbonyl-N-methyl) 3-morpholino rifamycin S:

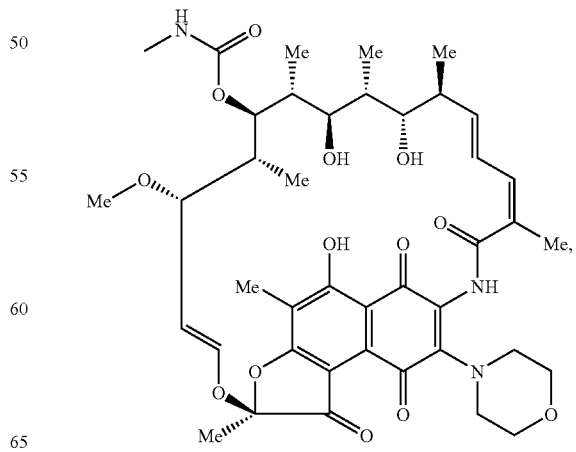

(r) 25-O-Desacetyl-1-carbonyl-N-[4-chlorobenzyl] 3-morpholino rifamycin S:
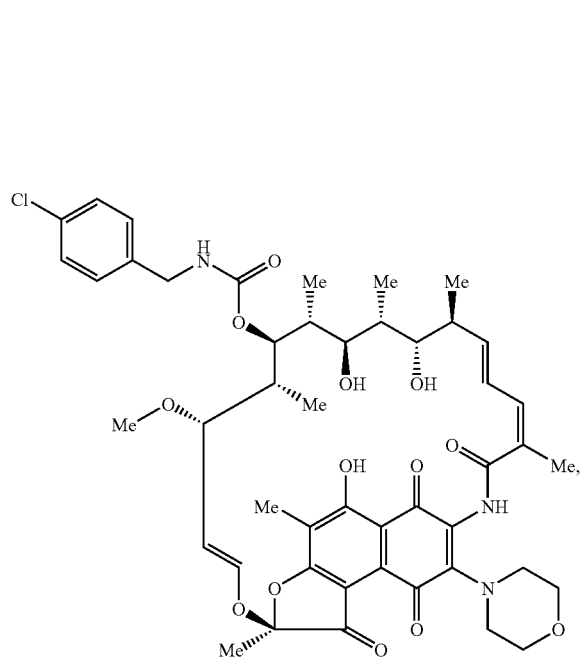
(s) 25-O-Desacetyl-1-carbonyl-N-[naphthalen-1-ylmethyl-amino] 3-morpholino rifamycin S:
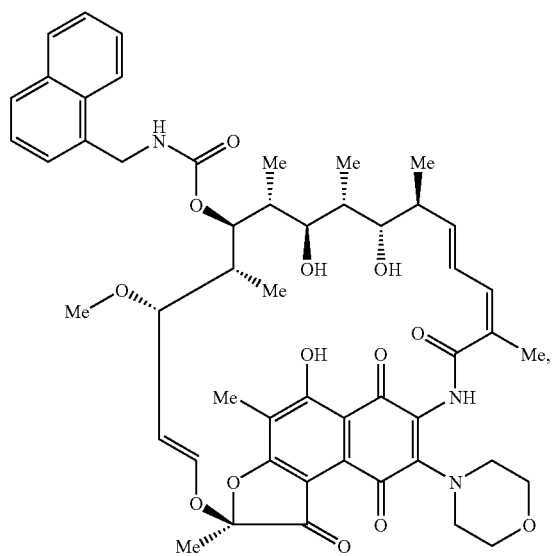
(t) 25-O-Desacetyl-1-carbonyl-N-[3-phenylpropylamino] 3-morpholino rifamycin S:
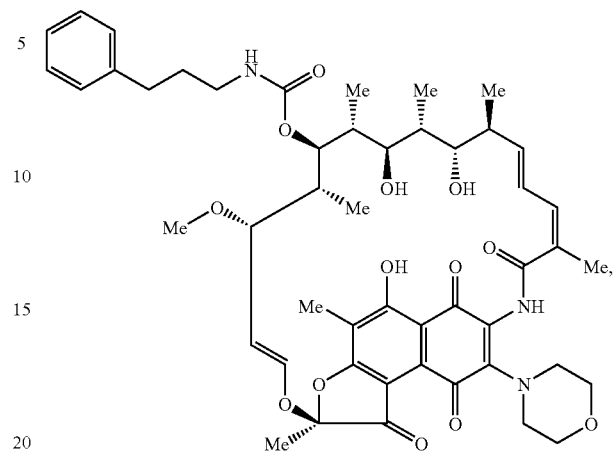
(u) 25-O-Desacetyl-1-carbonyl-N-[3-phenylethylamino] 3-morpholino rifamycin S:
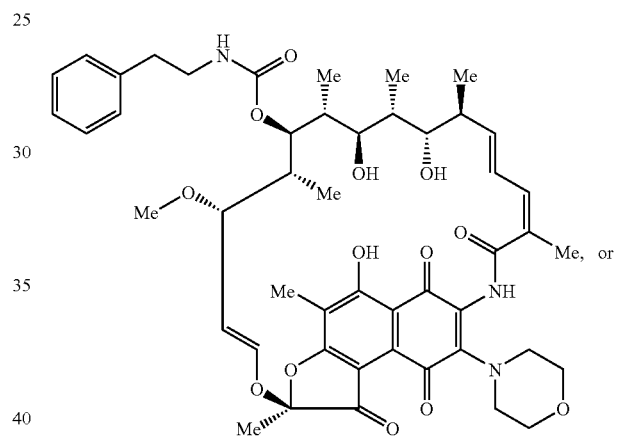
(v) 25-O-Desacetyl-1-carbonyl-N-[4-methoxybenzylamino] 3-morpholino rifamycin S:
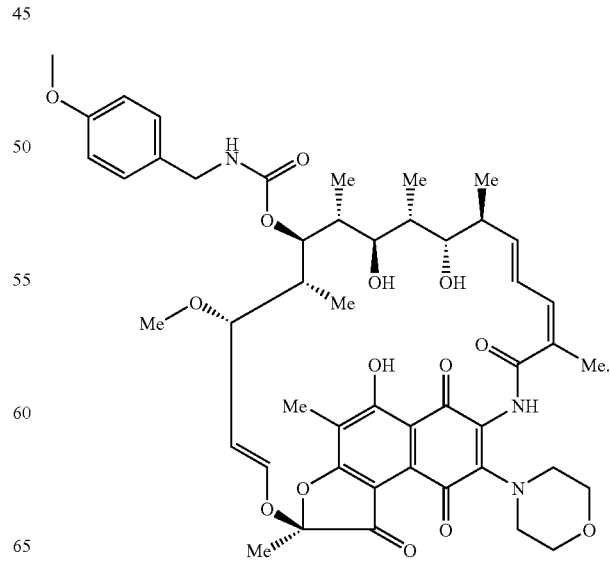

3. The compound of claim 1, wherein the structural formula is:

(a) 25-O-Desacetyl-1-carbonyl-N-[(2-amino-ethyl)-carbamic acid 6-[6-(4-dimethylamino-3-hydroxy-6-methyl-tetrahydro-pyran-2-yloxy)-14-ethyl-12,13-dihydroxy-7-methoxy-3,5,7,9,11,13-hexamethyl-2,10-dioxo-oxacyclotetradec-4-yloxy]-4-methoxy-2,4-dimethyl-tetrahydro-pyran-3-yl ester] 3-morpholino rifamycin S:

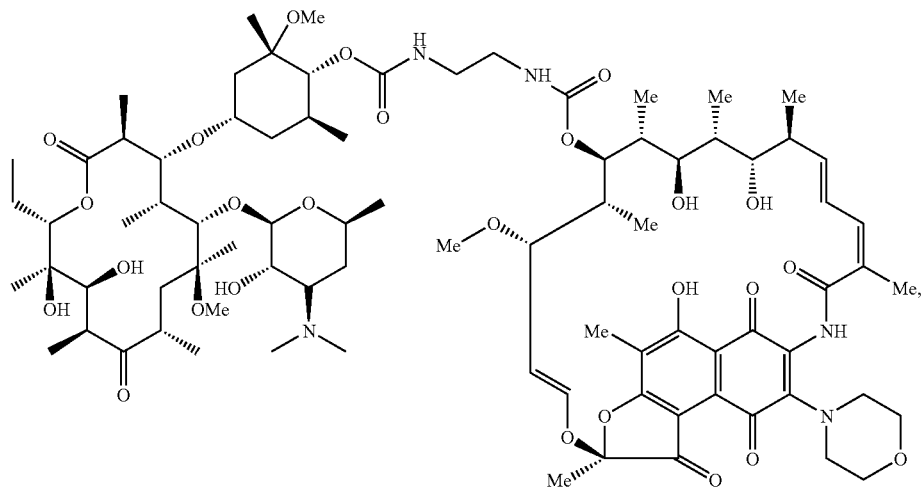

(b) 25-O-Desacetyl-1-carbonyl-N-[1-cyclopropyl-6-fluoro-8-methoxy-7-(3-methyl-piperazin-1-yl)-4-oxo-1,4-dihydro-quinoline-3-carboxylic acid] 3-morpholino rifamycin S:

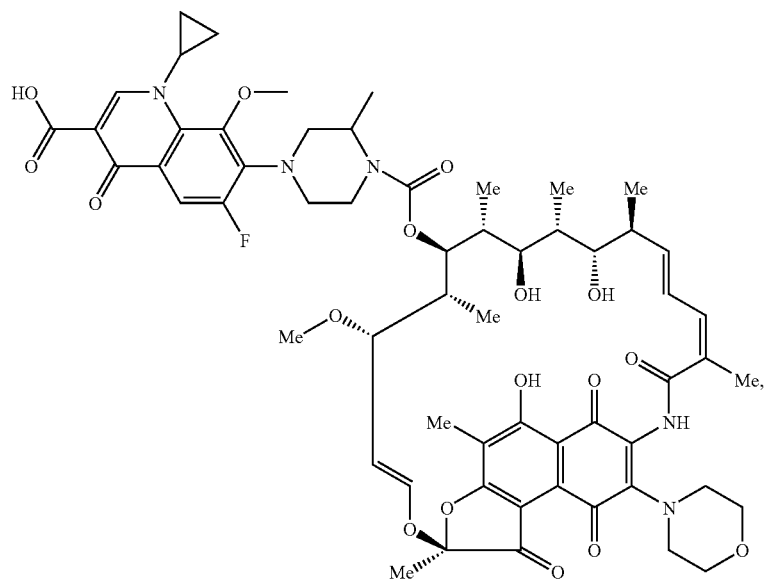

(c) 25-O-Desacetyl-1-carbonyl-N-[2-ethyl-octahydro-pyrrolo[3,4-c]pyrrole] 3-morpholino rifamycin S:

(e) 25-O-Desacetyl-1-carbonyl-N-[2-(1-methyl-pyrrolidin-2-yl)-ethylamine] 3-morpholino rifamycin S:

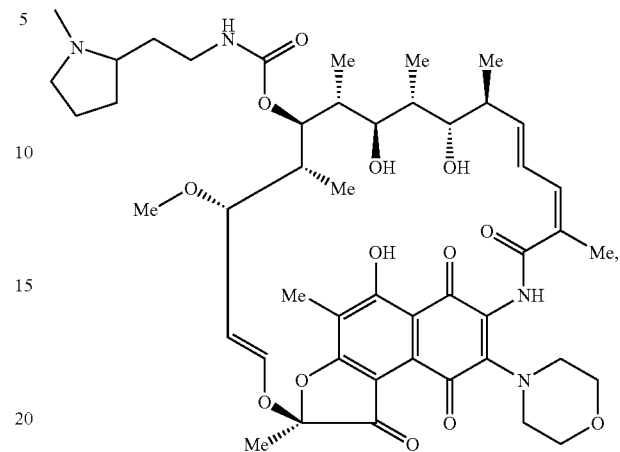

(f) 25-O-Desacetyl-(carbonyl-2-Pyrrolidin-1-yl-ethylamine) 3-morpholino rifamycin S:

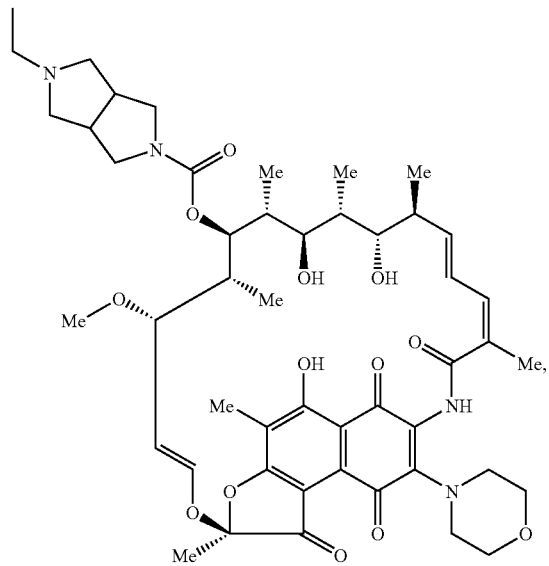

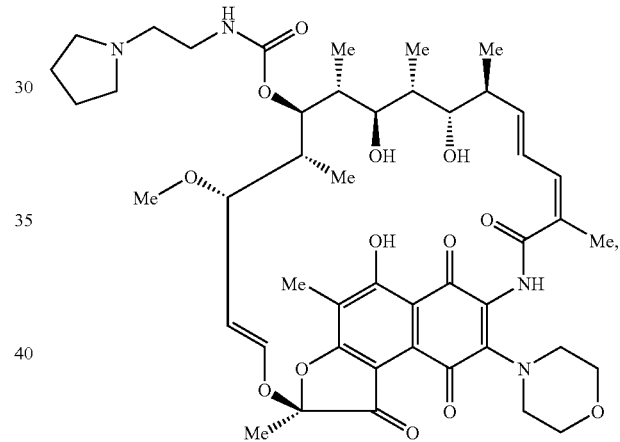

(d) 25-O-deacetyl-1,4-dideoxy-25-O-[[[2-(dimethylamino)ethyl]amino]carbonyl]-1,4-dihydro-3-(4-morpholinyl)-1,4-dioxo-rifamycin:

(g) 25-O-Desacetyl-1-carbonyl-N-[1-benzyl-piperidin-4-ylamine] 3-morpholino rifamycin S:

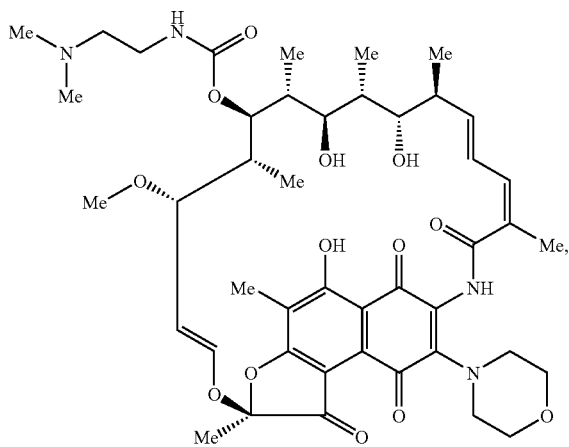

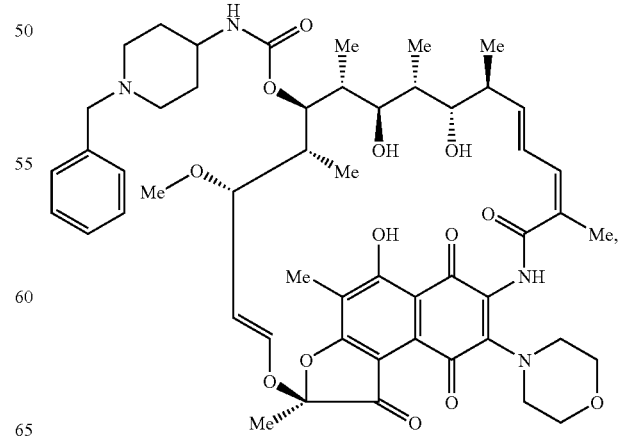

(h) 25-O-Desacetyl-1-carbonyl-N-[4-phenyl-butylamine] 3-morpholino rifamycin S:
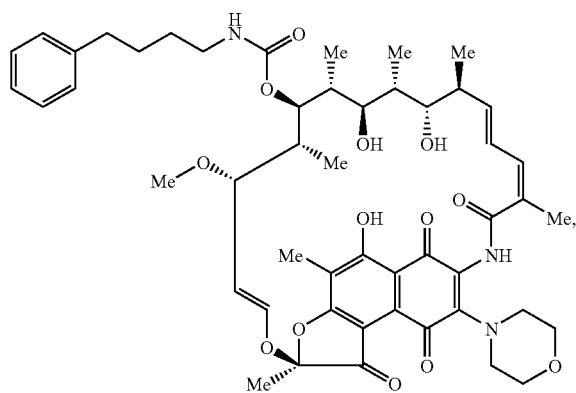
(i) 25-O-Desacetyl-1-carbonyl-N-([1,4']bipiperidinyl) 3-morpholino rifamycin S:
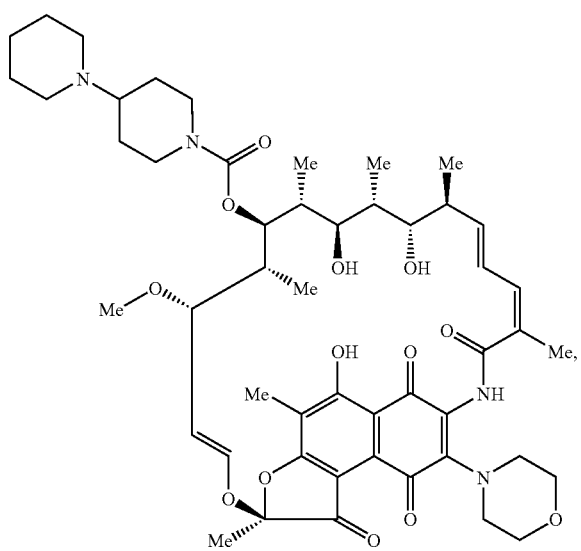
(j) 25-O-Desacetyl-1-carbonyl-N-[(4-aminomethyl-phenyl)-dimethyl-amine] 3-morpholino rifamycin S:
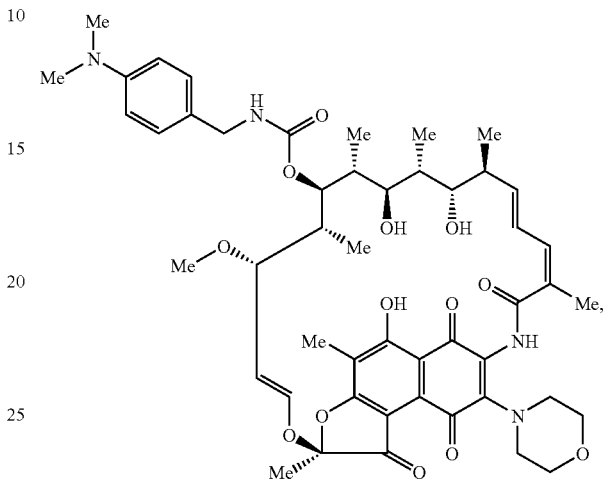
(k) 25-O-Desacetyl-1-carbonyl-N'-[benzyl-N,N-dimethyl-ethane-1,2-diamino) 3-morpholino rifamycin S:
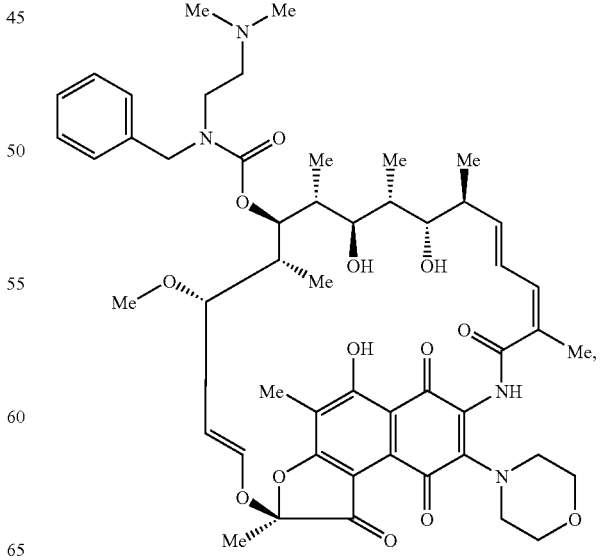

(l) 25-O-Desacetyl-1-carbonyl-N-[2-(4-chloro-phenyl)-ethylamine] 3-morpholino rifamycin S:

(n) 25-O-Desacetyl-1-[carbonyl-4-nitro-benzylamine] 3-morpholino rifamycin S:

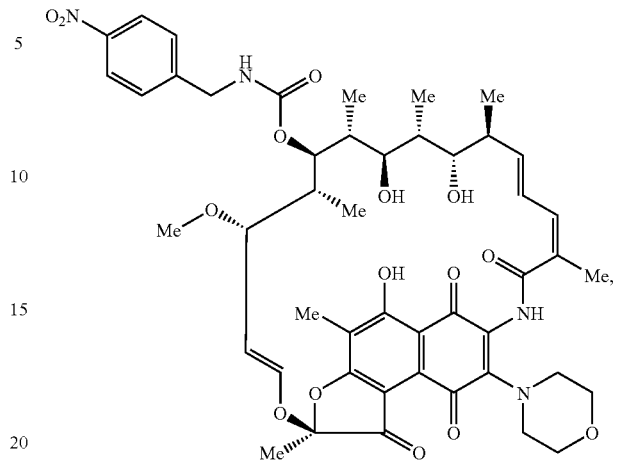

(o) 25-O-Desacetyl-1-carbonyl-N-[quinolin-3-yl-methylamino] 3-morpholino rifamycin S:

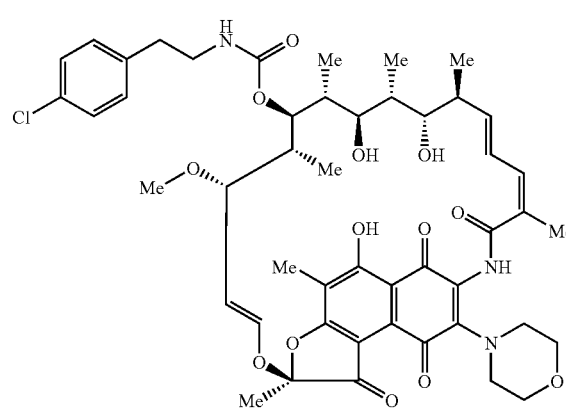

(m) 25-O-Desacetyl-1-carbonyl-N-[3-chloro-benzylamine] 3-morpholino rifamycin S:

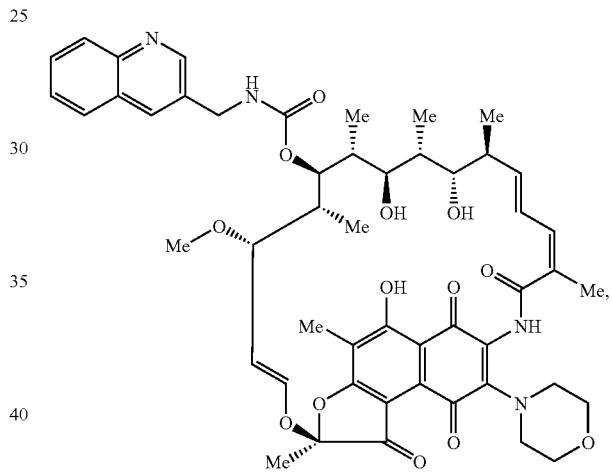

(p) 25-O-Desacetyl-1-carbonyl-N-[1-Cyclopropyl-6-fluoro-4-oxo-7-piperazin-1-yl-1,4-dihydro-quinoline-3-carboxylic acid]-3-morpholino rifamycin S:

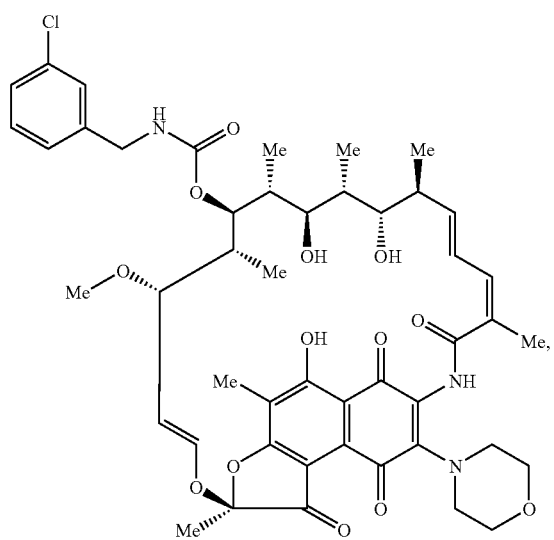

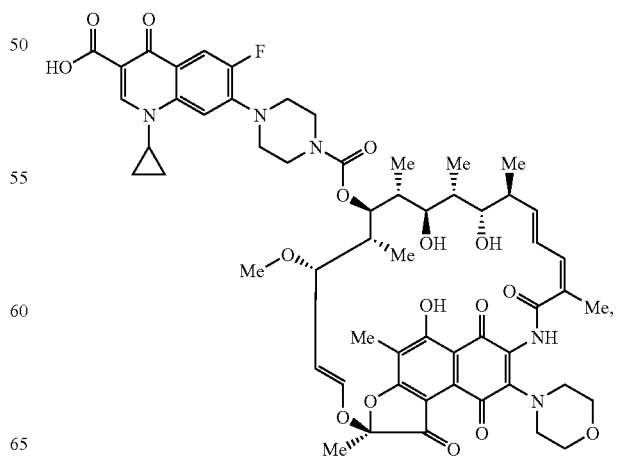

(q) 25-O-deacetyl-1,4-dideoxy-1,4-dihydro-3-(4-morpholinyl)-1,4-dioxo-25-O-[(2-propynylamino)carbonyl]-rifamycin S:

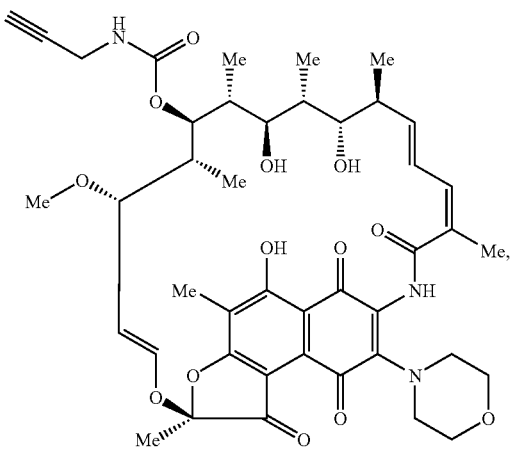

(r) 25-O-Desacetyl-1-carbonyl-N-[3-(3-amino-prop-1-ynyl)-phenyl]-methanol) 3-morpholino rifamycin S:

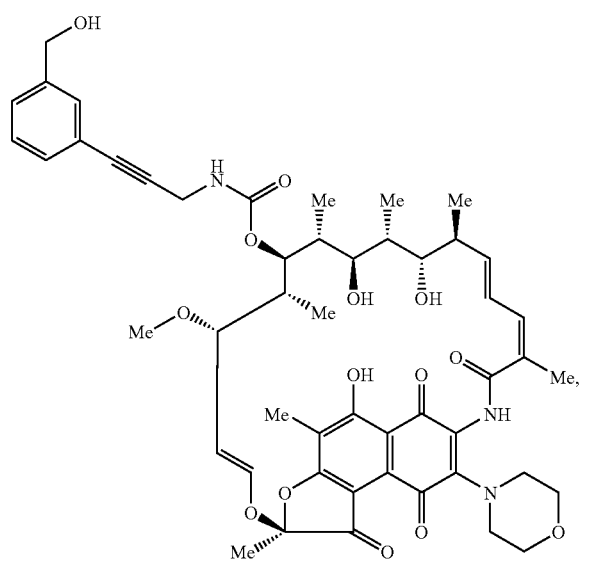

(s) 25-O-Desacetyl-1-carbonyl-N-[3-quinolin-3-yl-prop-2-ynylamine]-3-morpholino rifamycin S:

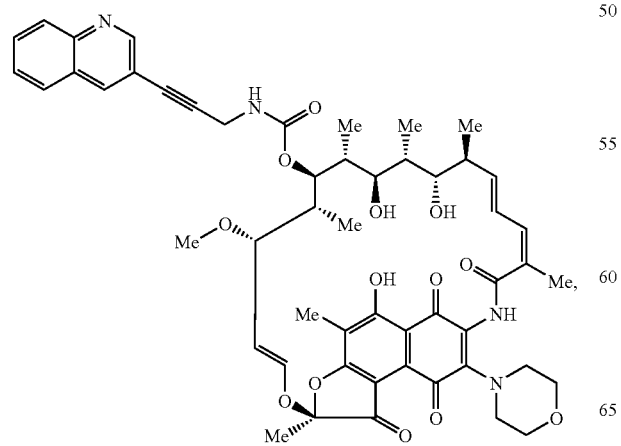

(t) 25-O-Desacetyl-1-carbonyl-N-[3-(2-methoxy-phenyl)-isoxazol-5-yl]-methylamino) 3-morpholino rifamycin S:

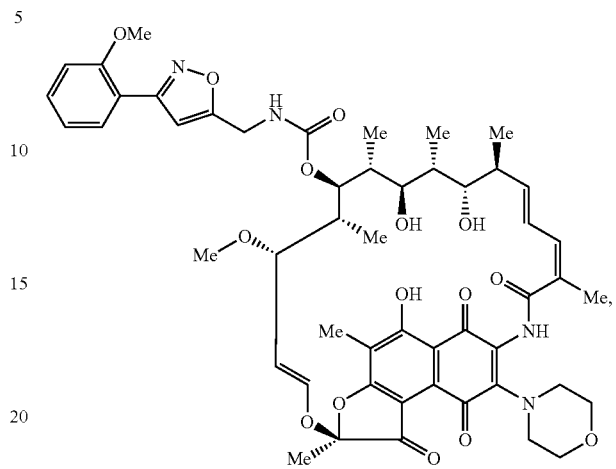

(u) 25-O-Desacetyl-1-carbonyl-N-[3-Pyridin-2-yl-isoxazol-5-yl)-methylamino]-3-morpholino rifamycin S:

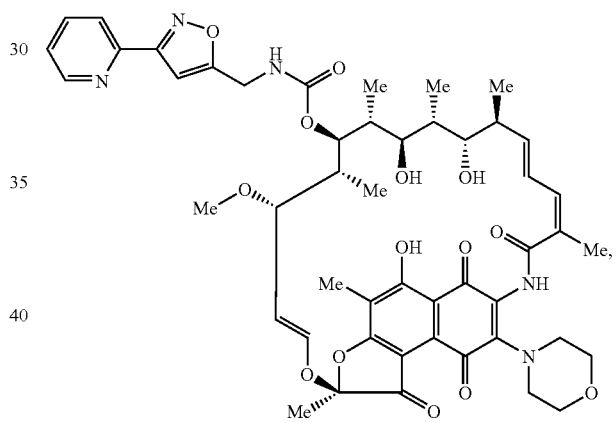

(v) 25-O-Desacetyl-1-carbonyl-N-[3-acetyl-isoxazol-5-ylmethylamino]-3-morpholino rifamycin S:

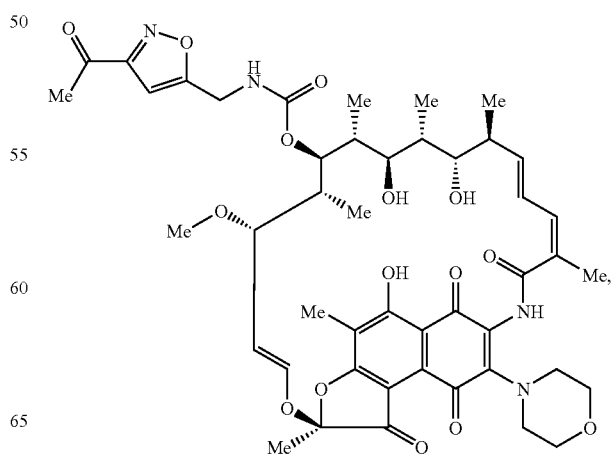

(w) 25-O-Desacetyl-(carbonyl-N-Hydroxy-N'-phenyl-4-(2-piperazin-1-yl-ethylamino)-3-trifluoromethyl-benzamidine) 3-morpholino rifamycin S:
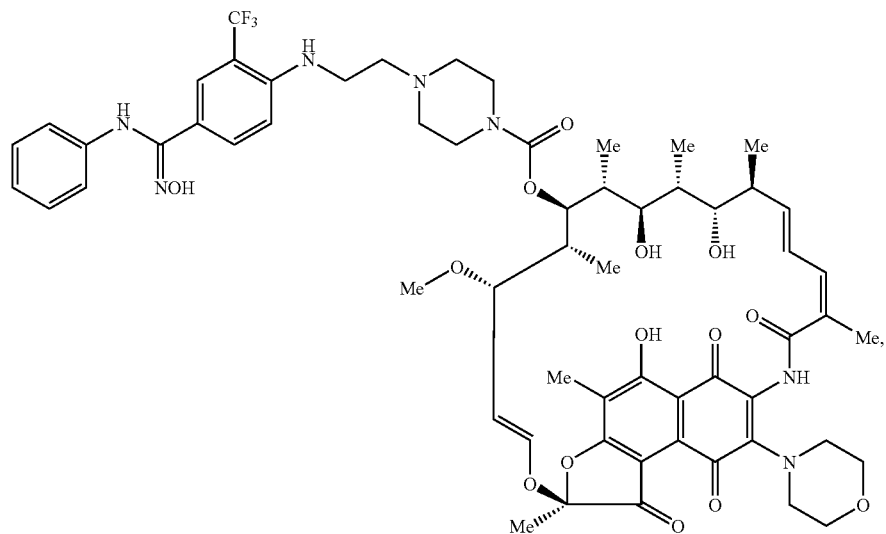
(x) 25-O-Desacetyl-(carbonyl-N-(2-Methyl-1H-indol-5-yl)-4-piperazin-1-yl-3-trifluoromethyl-benzamide) 3-morpholino rifamycin S:
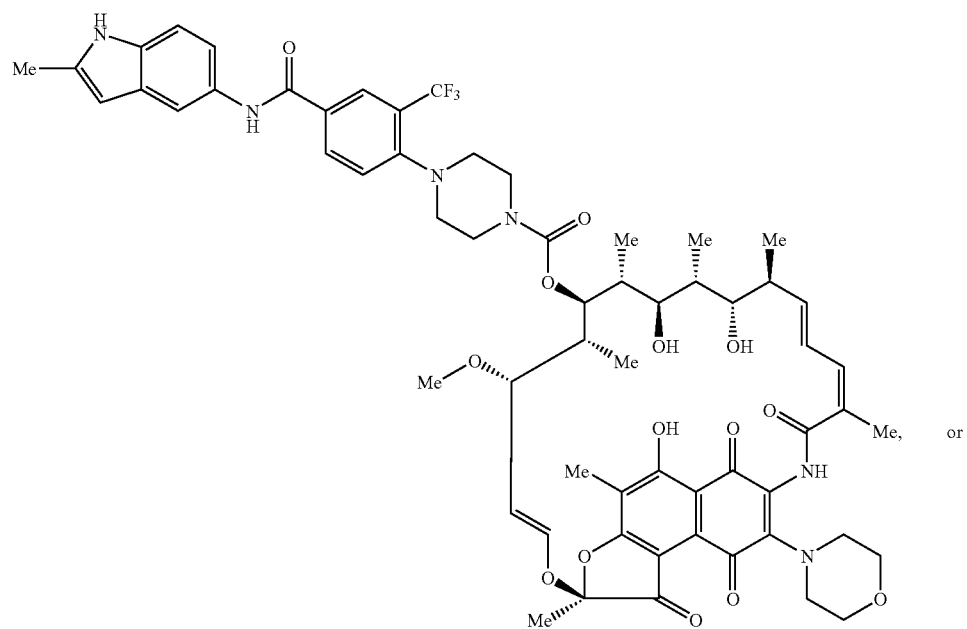

(y) 25-O-Desacetyl-(carbonyl-N-(5-methoxy-pyridin-3-yl)-4-piperazin-1-yl-3-trifluoromethyl-benzamide) 3-morpholino rifamycin S:
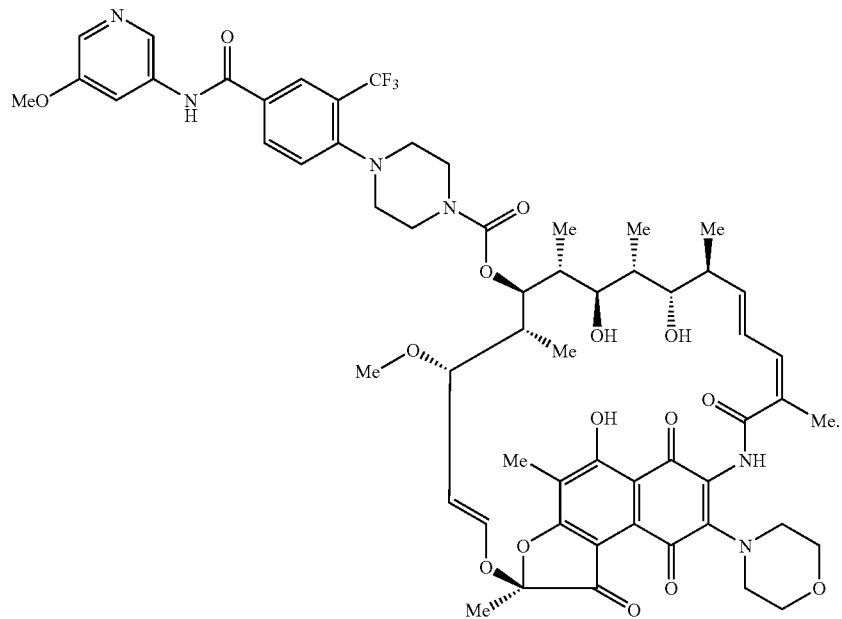
4. The compound of claim 1, wherein the structural formula is:
(a) 25-O-desacetyl-1-carbonyl-N-[1-cyclopropyl-6-fluoro-8-methoxy-7-(octahydro-pyrrolo[3,4-b]pyridin-6-yl)-4-oxo-1,4-dihydro-quinoline-3-carboxylic acid]-3-morpholino rifamycin S:
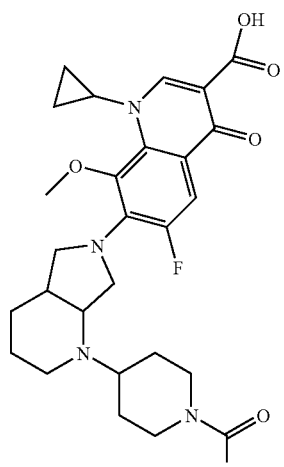
-continued
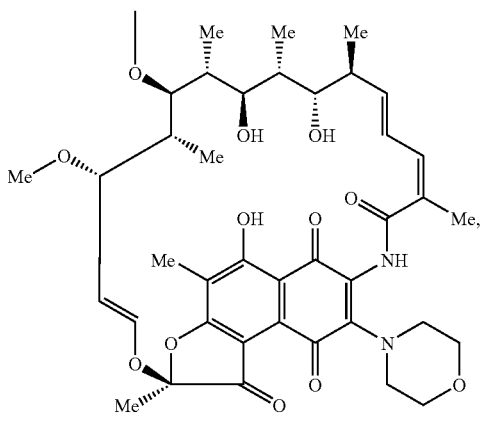

(b) 25-O-Desacetyl-1-carbonyl-N-[1-Cyclopropyl-6-fluoro-8-methoxy-7-[3-(piperidin-4-ylamino)-pyrrolidin-1-yl]-4-oxo-1,4-dihydro-quinoline-3-carboxylic acid7-(3-amino-piperidin-1-yl)-1-cyclopropyl-6-fluoro-8-methoxy-4-oxo-1,4-dihydro-quinoline-3-carboxylic acid]-3-morpholino rifamycin S:

-continued

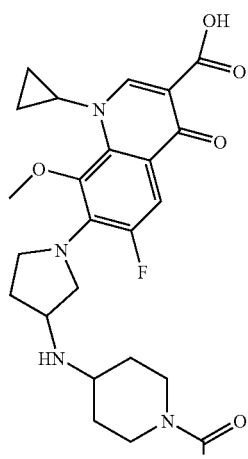

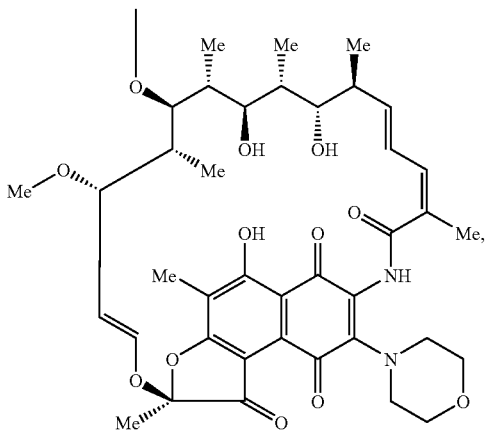

(c) 25-O-Desacetyl-1-carbonyl-N-[1-cyclopropyl-6-fluoro-8-methoxy-4-oxo-7-piperazin-1yl-1,4-dihydro-quinoline-3-carboxylic acid]-3-morpholino rifamycin S:

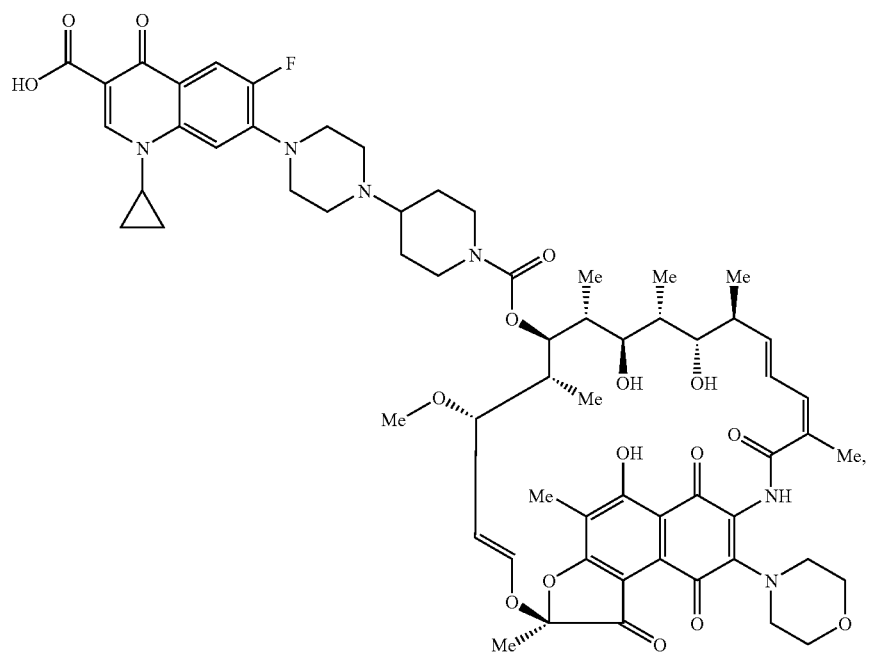

(d) A compound having the formula: 25-O-Desacetyl-1-carbonyl-N-[1-cyclopropyl-6-fluoro-8-methoxy-7-[4-(piperidin-4-ylamino)-piperidin-1-yl]-4-oxo-1,4-dihydro-quinoline-3-carboxylic acid]-3-morpholine-rifamycin S:
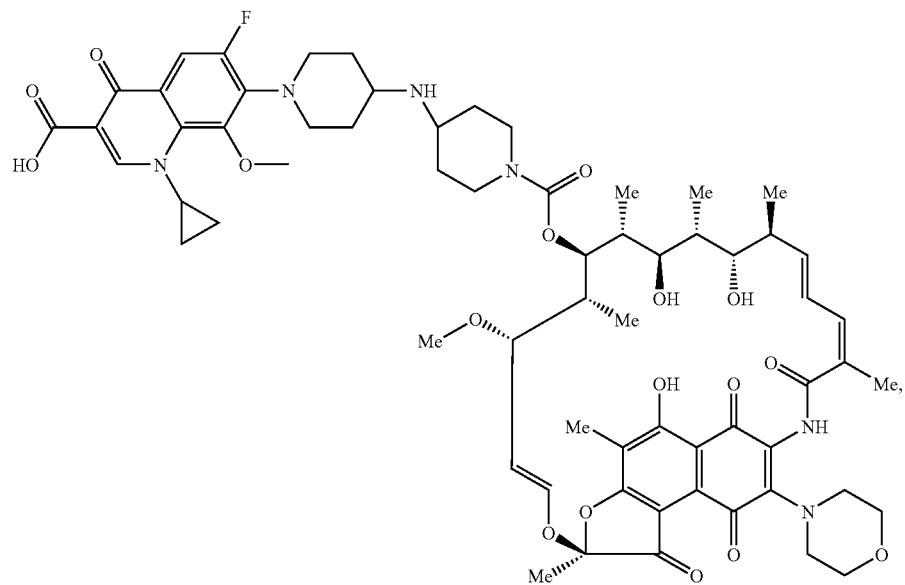
(e) 25-O-Desacetyl-(carbonyl-N-(1-Cyclopropyl-6-fluoro-8-methoxy-7-[3-piperidin-4-ylamino)-piperidin-1-yl]-4-oxo-1,4-dihydro-quinoline-3-carboxylic acid) 3-morpholine rifamycin S:
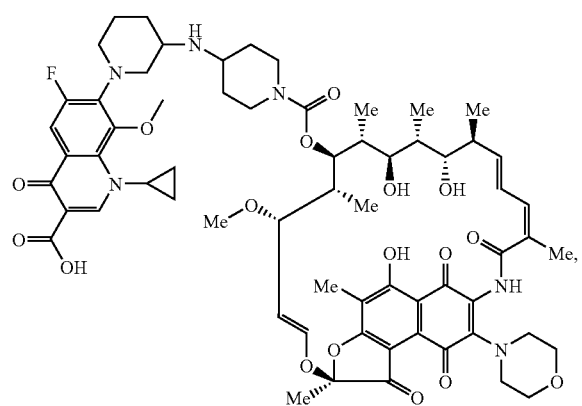

(f) 25-O-Desacetyl-(carbonyl-N-[1-cyclopropyl-6-fluoro-8-methoxy-7-[4-(1-methoxycarbonyl-piperidin-4-yl)-piperazin-1-yl]-4-oxo-1,4-dihydro-quinoline-3-carboxylic acid]-3-morpholino rifamycin S:
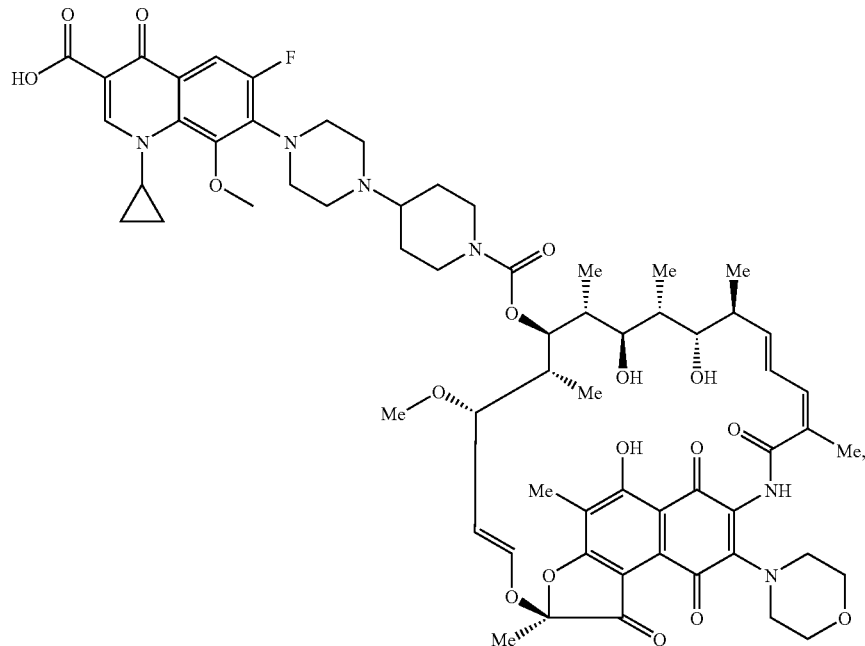
(g) 25-O-Desacetyl-(carbonyl-N-(1-cyclopropyl-6-fluoro-8-methoxy-4-oxo-7-(4-pyrrolidin-3-yl-piperazin-1-yl)-1,4-dihydro-quinoline-3-carboxylic acid 3-morpholino rifamycin S:
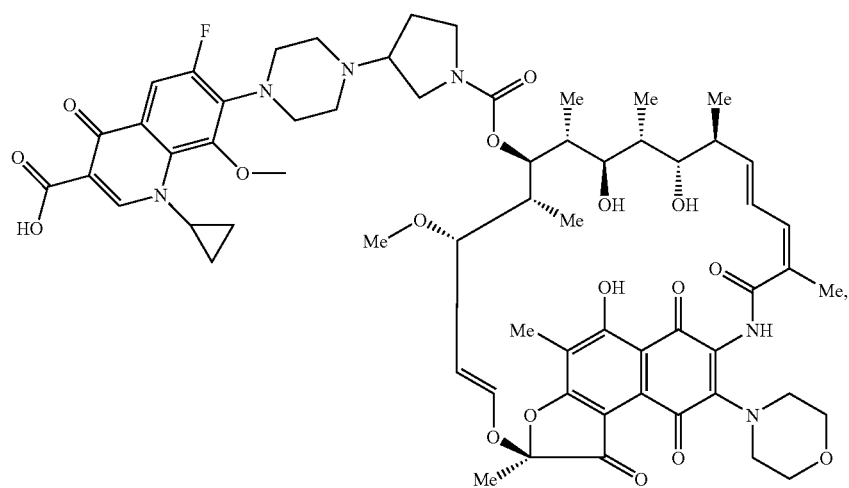

(h) 25-O-Desacetyl-(carbonyl-N-(7-[3-(2-amino-acetylamino)-pyrrolidin-1-yl]-8-chloro-1-cyclopropyl-6-fluoro-4-oxo-1,4-dihydro-quinoline-3-carboxylic acid 3-morpholino rifamycin S:
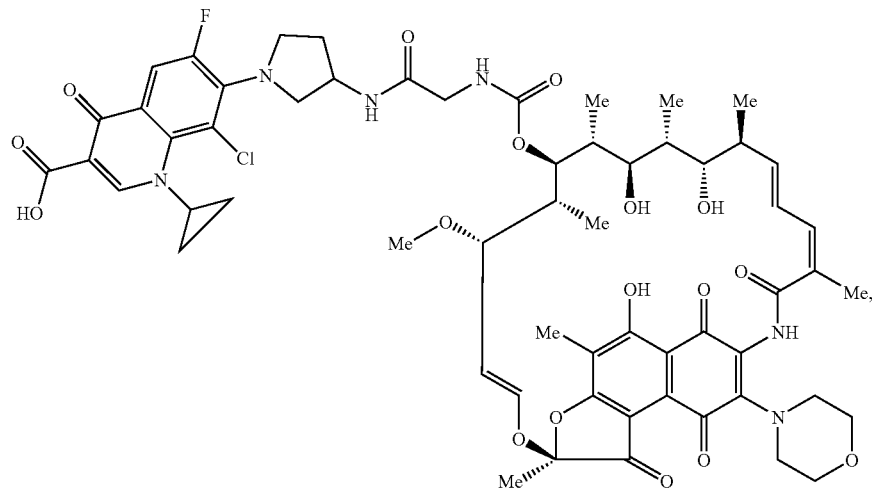
(i) 25-O-Desacetyl-(carbonyl-N-(7-[4-(2-amino-acetyl)-piperazin-1-yl]-1-cyclopropyl-6-fluoro-8-methoxy-4-oxo-1,4-dihydro-quinoline-3-carboxylic acid 3-morpholino rifamycin S:
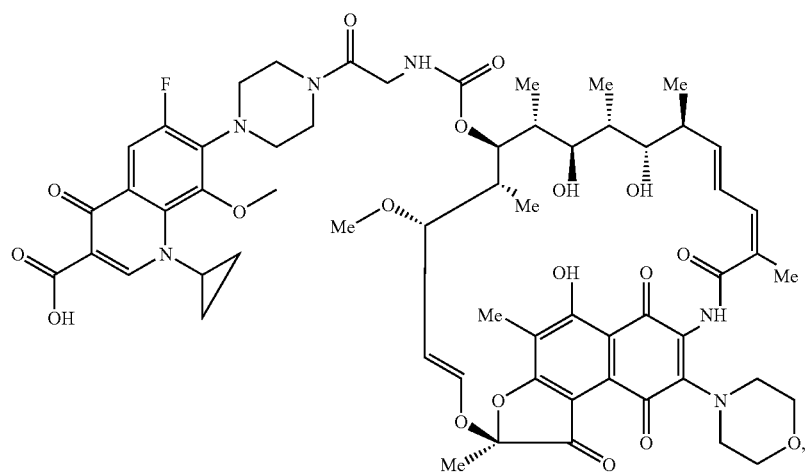

(j) 25-O-Desacetyl-(carbonyl-N-(7-[4-(azetidine-3-carbonyl)-piperazin-1-yl]-1-cyclopropyl-6-fluoro-8-methoxy-4-oxo-1,4-dihydro-quinoline-3-carboxylic acid) 3-morpholino rifamycin S:
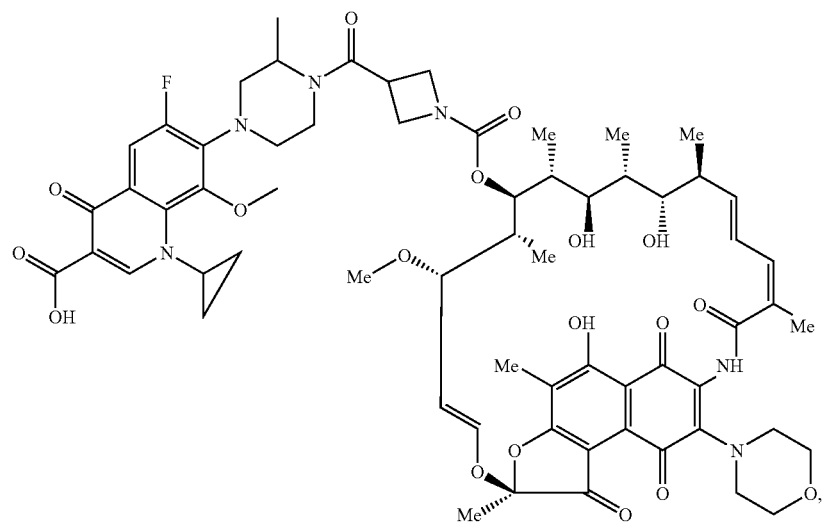
(k) 25-O-Desacetyl-(carbonyl-N-(7-[4-(azetidine-3-carbonyl)-piperazin-1-yl]-1-cyclopropyl-6-fluoro-8-methoxy-4-oxo-1,4-dihydro-quinoline-3-carboxylic acid) 3-morpholino rifamycin S:
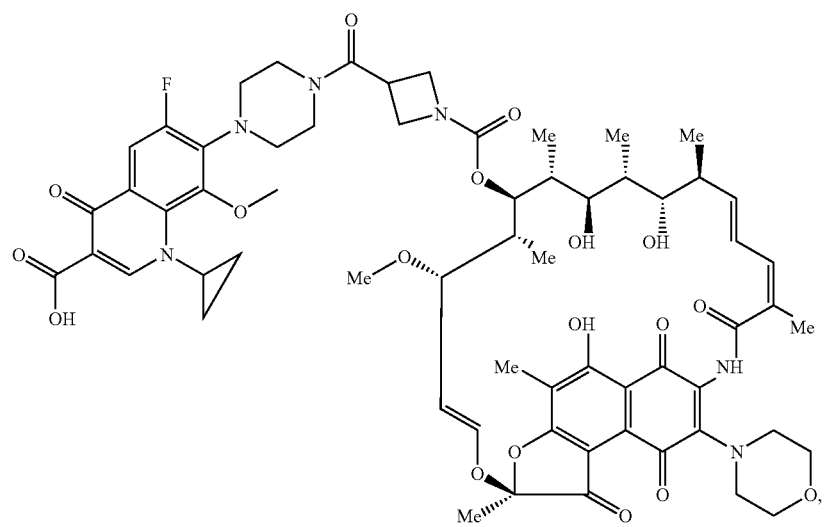

(l) 25-O-Desacetyl-N-[8-chloro-1-cyclopropyl-6-fluoro-7-(3-carbonylamino-pyrrolidin-1-yl)-4-oxo-1,4-dihydro-quinoline-3-carboxylic acid]-3-morpholino-rifamycin S:

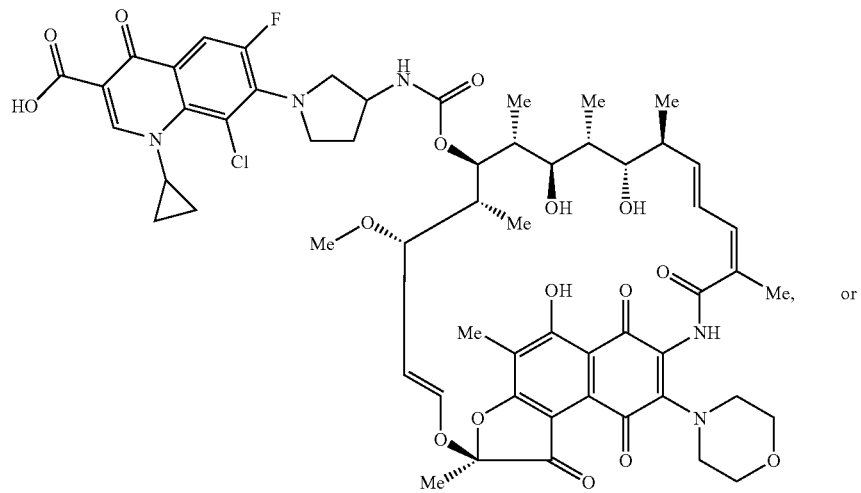

(m) 25-O-Desacetyl-N-[8-Chloro-1-cyclopropyl-6-fluoro-7-(3-carbonylamino-pyrrolidin-1-yl)-4-oxo-1,4-dihydro-quinoline-3-carboxylic acid]-3-morpholino-11-deoxy-11-hydroxyiminorifamycin S:

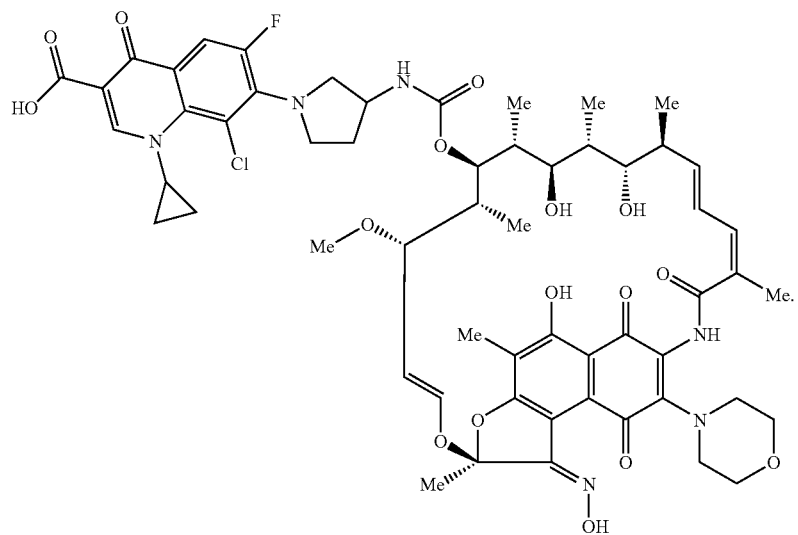

5. A method of treating a bacterial infection in a subject comprising: administering to the subject an effective amount of the compound of claim 1.

6. The method of claim 5, wherein the composition is administered to the subject in a total daily dose that is in the range of about 0.1 to about 100 mg/kg body weight of the subject.

7. The method of claim 5, wherein the bacterial infection is caused by a drug-resistant bacterium.

8. An antibiotic composition for the treatment or prevention of bacterial infections in a subject comprising a therapeutically effective amount of a compound of claim 1 in combination with a pharmaceutically acceptable carrier.

9. The antibiotic composition of claim 8, wherein the pharmaceutical acceptable carrier is an injectable solution, suspension, or emulsion.

10. The antibiotic composition of claim 8, wherein the pharmaceutical acceptable carrier is a non-irritating excipient.

11. The antibiotic composition of claim 8, wherein the pharmaceutical acceptable carrier is a liquid emulsion, microemulsion, solution, suspension, syrum or elixir suitable for oral administration to a subject.

12. The antibiotic composition of claim 8, wherein the pharmaceutically acceptable carrier is a filler, binder, humectant, disintegrating agent, solution retarding agent, absorption accelerator, wetting agent, or lubricant that is suitable for oral administration to a subject.

13. The antibiotic composition of claim 8, wherein the therapeutically effective amount is between about 0.1 and about 100 mg/kg body weight of the subject.

14. A compound having a formula:

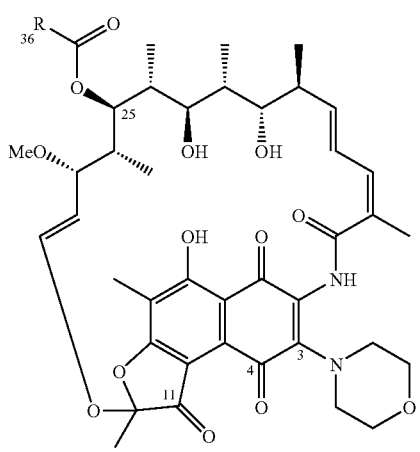

or its pharmaceutically acceptable salt thereof wherein,
R is $CH_3NH-$, $(CH_3)_2CH_2NH-$, $HOCH_2CH_2NH-$, $Me_2NCH_2CH_2NH-$, $CH_2=CHCH_2NH-$, $HCCCH_2NH-$, $Et_2N-$, $PhCH_2NH-$, $PhCH_2CH_2NH-$, $PhCH_2CH_2CH_2NH-$, $PhCH_2CH_2CH_2CH_2NH-$, 1-napthyl-$CH_2-NH-$ or one of the structural groups listed below:

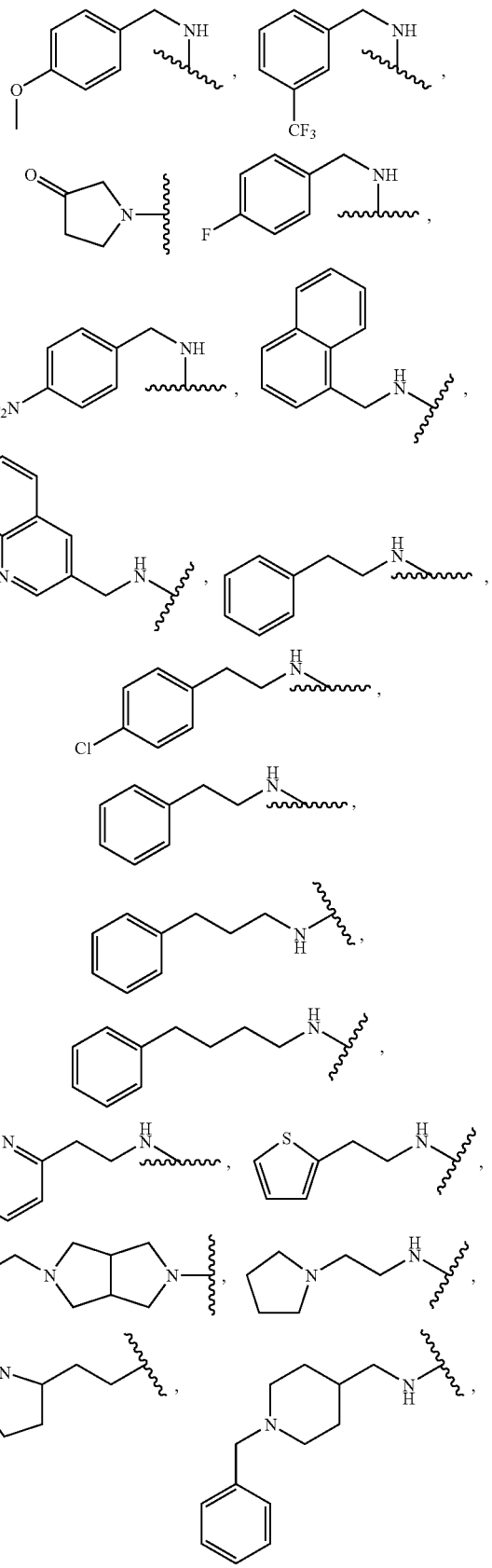

123
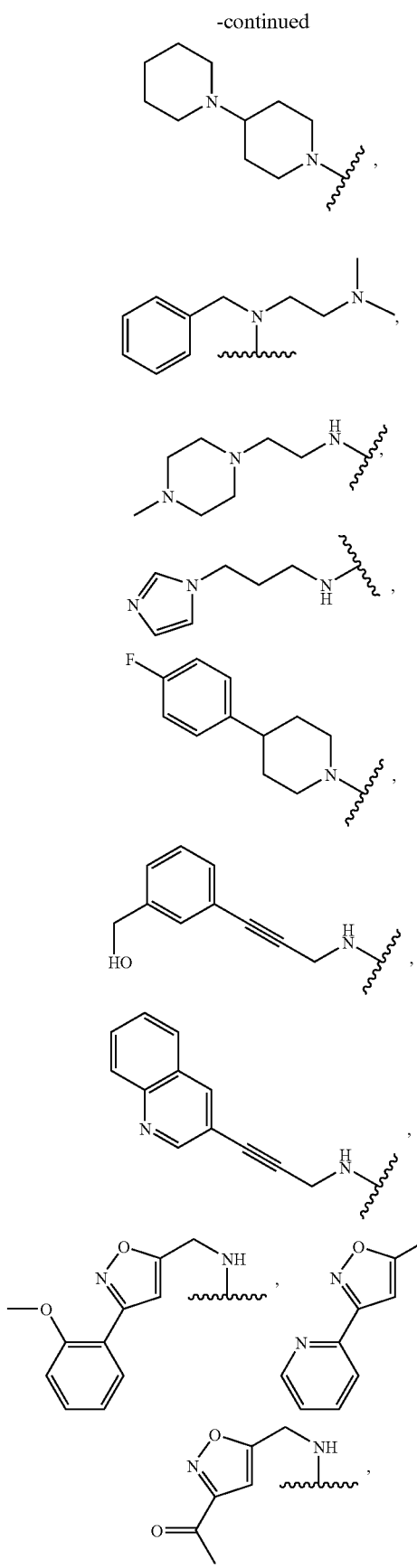
124
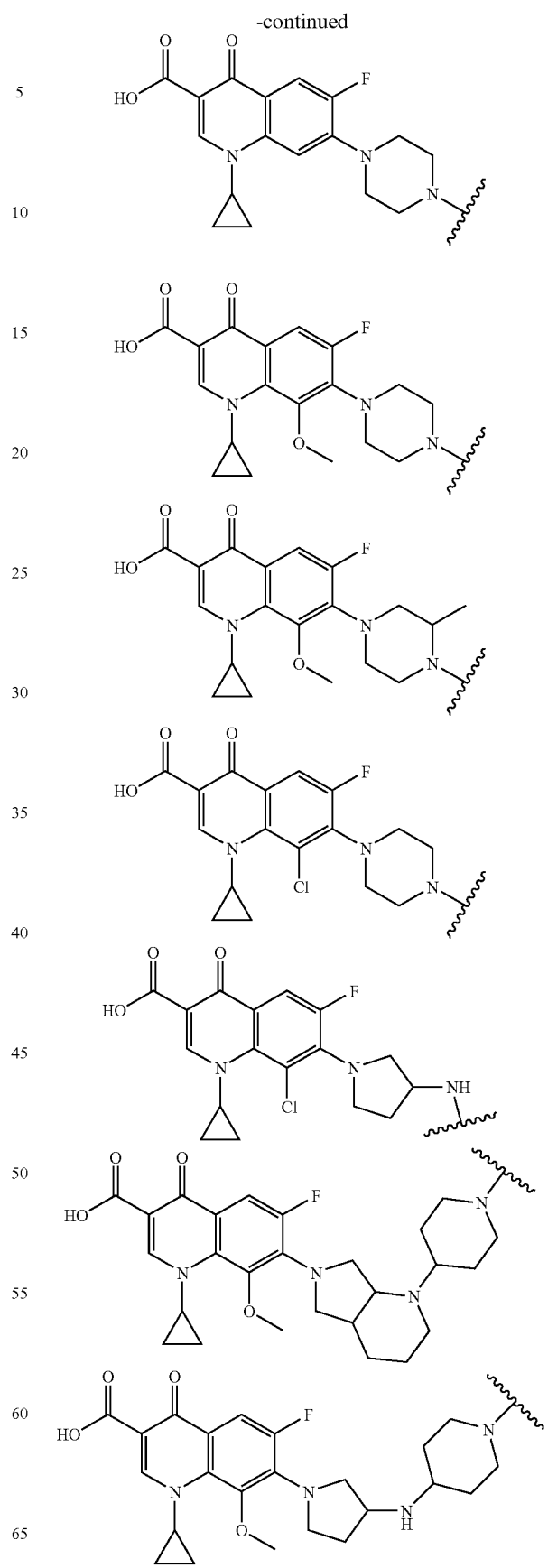

-continued

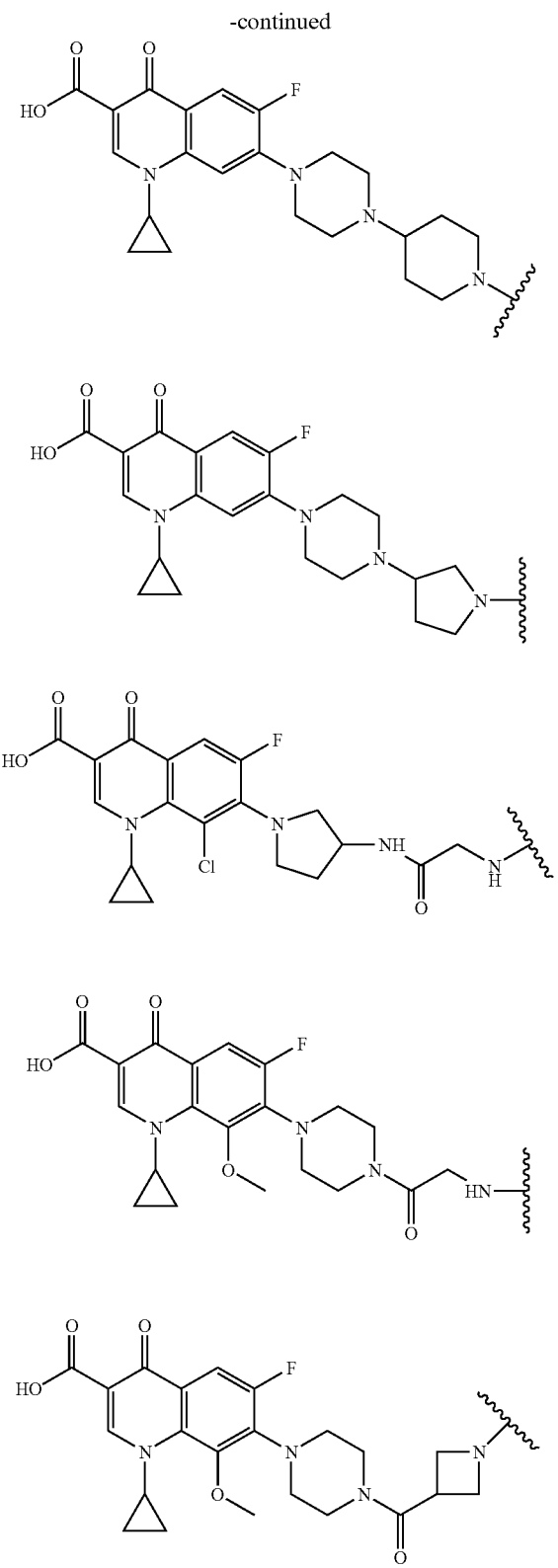

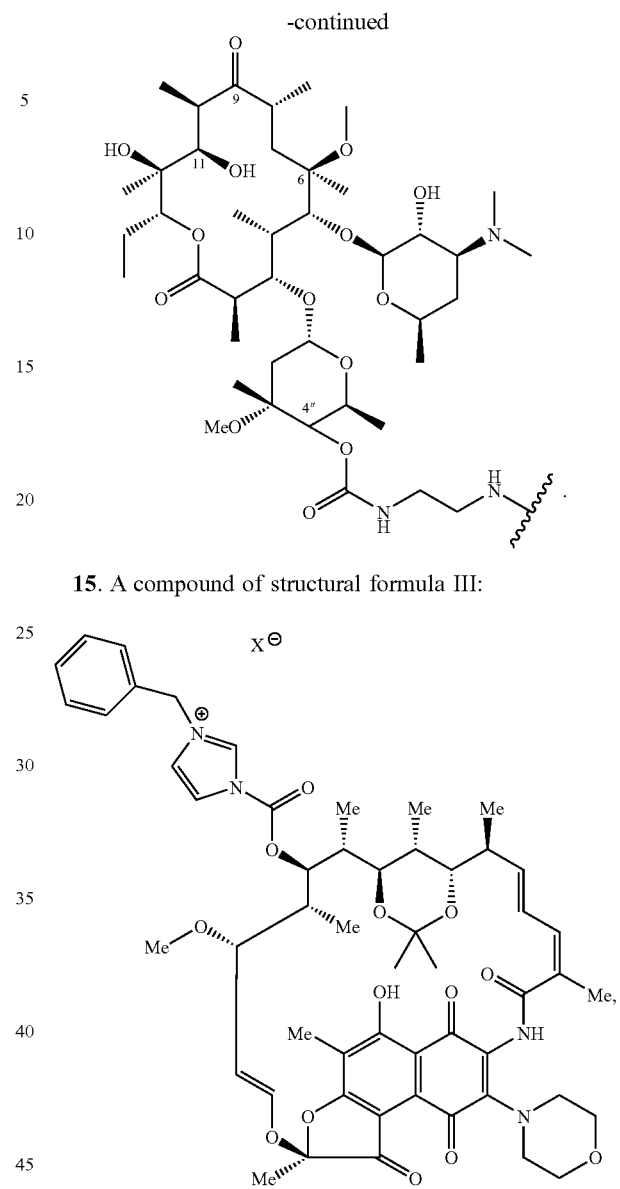

15. A compound of structural formula III:

wherein X⁻ is chloride, bromide, iodide, methanesulfonate or para-toluenesulfonate.

16. An antibiotic composition for the treatment or prevention of bacterial infections in a subject comprising a therapeutically effective amount of a compound of claim 2 in combination with a pharmaceutically acceptable carrier.

17. An antibiotic composition for the treatment or prevention of bacterial infections in a subject comprising a therapeutically effective amount of a compound of claim 3 in combination with a pharmaceutically acceptable carrier.

18. An antibiotic composition for the treatment or prevention of bacterial infections in a subject comprising a therapeutically effective amount of a compound of claim 4 in combination with a pharmaceutically acceptable carrier.

* * * * *